(12) United States Patent
Pass

(10) Patent No.: US 7,893,063 B2
(45) Date of Patent: Feb. 22, 2011

(54) 2,4,6-TRISUBSTITUTED PYRIMIDINES AS PHOSPHOTIDYLINOSITOL (PI) 3-KINASE INHIBITORS AND THEIR USE IN THE TREATMENT OF CANCER

(75) Inventor: Martin Pass, Macclesfield (GB)

(73) Assignee: AstraZeneca AB, Södertälje (SE)

( * ) Notice: Subject to any disclaimer, the term of this patent is extended or adjusted under 35 U.S.C. 154(b) by 910 days.

(21) Appl. No.: 11/630,881

(22) PCT Filed: Jul. 7, 2005

(86) PCT No.: PCT/GB2005/002665

§ 371 (c)(1),
(2), (4) Date: Dec. 27, 2006

(87) PCT Pub. No.: WO2006/005915

PCT Pub. Date: Jan. 19, 2006

(65) Prior Publication Data

US 2009/0143384 A1    Jun. 4, 2009

(30) Foreign Application Priority Data

Jul. 9, 2004    (GB) .................................. 0415364.9

(51) Int. Cl.
*C07D 413/14*    (2006.01)
*A61K 31/5377*    (2006.01)
(52) U.S. Cl. .................. 514/235.8; 514/234.5; 544/122
(58) Field of Classification Search .................. 544/122
See application file for complete search history.

(56) References Cited

U.S. PATENT DOCUMENTS

| 7,566,712 | B2 * | 7/2009 | Bakthavatchalam et al. . | 514/245 |
| 2007/0027155 | A1 * | 2/2007 | Bakthavatchalam et al. . | 514/241 |

FOREIGN PATENT DOCUMENTS

| EP | 1 277 738 | 1/2003 |
| WO | WO 94/07867 | 4/1994 |
| WO | WO 04/000820 | 12/2003 |
| WO | WO 2004/048365 | 6/2004 |
| WO | WO 2005/003099 | 1/2005 |
| WO | WO 2005/007648 | 1/2005 |
| WO | WO 2005/042519 | 5/2005 |
| WO | WO 2006/005914 | 1/2006 |
| WO | WO 2006/005918 | 1/2006 |
| WO | WO 2007/042806 | 4/2007 |
| WO | WO 2007/042810 | 4/2007 |

OTHER PUBLICATIONS

Rautio et al. Nature Reviews Drug Discovery 2008, 7, pp. 255-270.*
Wang et al. Drug Delivery: Principles and Applications, 2005 John Wiley & Sons, Inc. Publication, Section 8.3, pp. 136-137.*
Smith, D. A. Current Opinion in Drug Discovery & Development 2007, 10, 550-559.*
Testa, B. Current Opinion in Chemical Biology 2009, 13, pp. 338-344.*
Katiyar, S. et al. "Syntheses of 2,4,6-trisubstituted pyrimidine derivatives as a new class of antifilarial topoisomerase II inhibitors" Bioorg. Med. Chem. Lett. 15(1):47-50 (2005).

* cited by examiner

*Primary Examiner*—Rebecca L Anderson
*Assistant Examiner*—Matthew P Coughlin

(57)    ABSTRACT

The invention concerns pyrimidine derivatives of Formula (I) wherein each of $Q^a$, $G^1$, $G^2$, q, $R^3$, r, $R^4$, $X^1$ and $Q^b$ have any of the meanings defined in the description; processes for their preparation, pharmaceutical compositions containing them and their use in the manufacture of a medicament for use in the production of an anti-proliferative effect in a warm-blooded animal such as man.

10 Claims, No Drawings

2,4,6-TRISUBSTITUTED PYRIMIDINES AS PHOSPHOTIDYLINOSITOL (PI) 3-KINASE INHIBITORS AND THEIR USE IN THE TREATMENT OF CANCER

The invention concerns certain novel pyrimidine derivatives, or pharmaceutically-acceptable salts, solvates or prodrugs thereof, which possess anti-tumour activity and are accordingly useful in methods of treatment of the human or animal body. The invention also concerns processes for the manufacture of said pyrimidine derivatives, to pharmaceutical compositions containing them and to their use in therapeutic methods, for example in the manufacture of medicaments for use in production of an anti-proliferative effect in a warm-blooded animal such as man.

Many of the current treatment regimes for cell proliferation diseases such as cancer and psoriasis utilise compounds which inhibit DNA synthesis. Such compounds are toxic to cells generally but their toxic effect on rapidly dividing cells such as tumour cells can be beneficial. Alternative approaches to anti-tumour agents which act by mechanisms other than the inhibition of DNA synthesis have the potential to display enhanced selectivity of action.

In recent years it has been discovered that a cell may become cancerous by virtue of the transformation of a portion of its DNA into an oncogene, that is a gene which, on activation, leads to the formation of malignant tumour cells (Bradshaw, *Mutagenesis*, 1986, 1, 91). Several such oncogenes give rise to the production of peptides which are receptors for growth factors. Activation of the growth factor receptor complex subsequently leads to an increase in cell proliferation. It is known, for example, that several oncogenes encode tyrosine kinase enzymes and that certain growth factor receptors are also tyrosine kinase enzymes (Yarden et al., *Ann. Rev. Biochem.*, 1988, 57, 443; Larsen et al., *Ann. Reports in Med. Chem.*, 1989, Chpt. 13). The first group of tyrosine kinases to be identified arose from such viral oncogenes, for example $pp60^{v-Src}$ tyrosine kinase (otherwise known as v-Src), and the corresponding tyrosine kinases in normal cells, for example $pp60^{c-Src}$ tyrosine kinase (otherwise known as c-Src).

Receptor tyrosine kinases are important in the transmission of biochemical signals which initiate cell replication. They are large enzymes which span the cell membrane and possess an extracellular binding domain for growth factors such as epidermal growth factor (EGF) and an intracellular portion which functions as a kinase to phosphorylate tyrosine amino acids in proteins and hence to influence cell proliferation. Various classes of receptor tyrosine kinases are known (Wilks, *Advances in Cancer Research*, 1993, 60, 43-73) based on families of growth factors which bind to different receptor tyrosine kinases. The classification includes Class I receptor tyrosine kinases comprising the EGF family of receptor tyrosine kinases such as the EGF, TGFα, Neu and erbB receptors.

It is also known that certain tyrosine kinases belong to the class of non-receptor tyrosine kinases which are located intracellularly and are involved in the transmission of biochemical signals such as those that influence tumour cell motility, dissemination and invasiveness and subsequently metastatic tumour growth. Various classes of non-receptor tyrosine kinases are known including the Src family such as the Src, Lyn, Fyn and Yes tyrosine kinases.

It is also known that certain kinases belong to the class of serine/threonine kinases which are located intracellularly and downstream of tyrosine kinase activation and are involved in the transmission of biochemical signals such as those that influence tumour cell growth. Such serine/threonine signalling pathways include the Raf-MEK-ERK cascade and those downstream of PI3K such as PDK-1, AKT and mTOR (Blume-Jensen and Hunter, *Nature*, 2001, 411, 355).

It is also known that certain other kinases belong to the class of lipid kinases which are located intracellularly and are also involved in the transmission of biochemical signals such as those that influence tumour cell growth and invasiveness. Various classes of lipid kinases are known including the phosphoinositide 3-kinase (abbreviated hereinafter to PI3K) family that is alternatively known as the phosphatidylinositol-3-kinase family.

It is now well understood that deregulation of oncogenes and tumour-suppressor genes contributes to the formation of malignant tumours, for example by way of increased cell proliferation or increased cell survival. It is also now known that signalling pathways mediated by the PI3K family have a central role in a number of cell processes including proliferation and survival, and deregulation of these pathways is a causative factor a wide spectrum of human cancers and other diseases (Katso et al., *Annual Rev. Cell Dev. Biol.*, 2001, 17: 615-617 and Foster et al., *J. Cell Science*, 2003, 116: 3037-3040).

The PI3K family of lipid kinases is a group of enzymes that phosphorylate the 3-position of the inositol ring of phosphatidylinositol (abbreviated hereinafter to PI). Three major groups of PI3K enzymes are known which are classified according to their physiological substrate specificity (Vanhaesebroeck et al., *Trends in Biol. Sci.*, 1997, 22, 267). Class III PI3K enzymes phosphorylate PI alone. In contrast, Class II PI3K enzymes phosphorylate both PI and PI 4-phosphate [abbreviated hereinafter to PI(4)P]. Class I PI3K enzymes phosphorylate PI, PI(4)P and PI 4,5-bisphosphate [abbreviated hereinafter to PI(4,5)P2], although only PI(4,5)P2 is believed to be the physiological cellular substrate. Phosphorylation of PI(4,5)P2 produces the lipid second messenger PI 3,4,5-triphosphate [abbreviated hereinafter to PI(3,4,5)P3]. More distantly related members of this superfamily are Class IV kinases such as mTOR and DNA-dependent kinase that phosphorylate serine/threonine residues within protein substrates. The most studied and understood of these lipid kinases are the Class I PI3K enzymes.

Class I PI3K is a heterodimer consisting of a p110 catalytic subunit and a regulatory subunit, and the family is further divided into Class Ia and Class Ib enzymes on the basis of regulatory partners and mechanism of regulation. Class Ia enzymes consist of three distinct catalytic subunits (p110α, p110β and p110δ) that dimerise with five distinct regulatory subunits (p85α, p55α, p50α, p85β and p55γ), with all catalytic subunits being able to interact with all regulatory subunits to form a variety of heterodimers. Class Ia PI3K are generally activated in response to growth factor-stimulation of receptor tyrosine kinases, via interaction of the regulatory subunit SH2 domains with specific phospho-tyrosine residues of the activated receptor or adaptor proteins such as IRS-1. Both p110α and p110β are constitutively expressed in all cell types, whereas p110δ expression is more restricted to leukocyte populations and some epithelial cells. In contrast, the single Class Ib enzyme consists of a p110γ catalytic subunit that interacts with a p101 regulatory subunit. Furthermore, the Class Ib enzyme is activated in response to G-protein coupled receptor (GPCR) systems and its expression appears to be limited to leukocytes.

There is now considerable evidence indicating that Class Ia PI3K enzymes contribute to tumorigenesis in a wide variety of human cancers, either directly or indirectly (Vivanco and Sawyers, *Nature Reviews Cancer*, 2002, 2, 489-501). For example, the p110α subunit is amplified in some tumours such as those of the ovary (Shayesteh et al., *Nature Genetics*, 1999, 21: 99-102) and cervix (Ma et al., *Oncogene*, 2000, 19: 2739-2744). More recently, activating mutations within the catalytic site of p110α have been associated with various other tumours such as those of the colorectal region and of the breast and lung (Samuels et al., *Science*, 2004, 304, 554). Tumour-related mutations in p85α have also been identified in cancers such as those of the ovary and colon (Philp et al., *Cancer Research*, 2001, 61, 7426-7429). In addition to direct effects, it is believed that activation of Class Ia PI3K contributes to tumorigenic events that occur upstream in signalling pathways, for example by way of ligand-dependent or ligand-independent activation of receptor tyrosine kinases, GPCR systems or integrins (Vara et al., *Cancer Treatment Reviews*, 2004, 30, 193-204). Examples of such upstream signalling pathways include over-expression of the receptor tyrosine kinase Erb2 in a variety of tumours leading to activation of PI3K-mediated pathways (Harari et al., *Oncogene*, 2000, 19, 6102-6114) and over-expression of the oncogene Ras (Kauffmann-Zeh et al., *Nature*, 1997, 385, 544-548). In addition, Class Ia PI3Ks may contribute indirectly to tumorigenesis caused by various downstream signalling events. For example, loss of the effect of the PTEN tumour-suppressor phosphatase that catalyses conversion of PI(3,4,5)P3 back to PI(4,5)P2 is associated with a very broad range of tumours via deregulation of PI3K-mediated production of PI(3,4,5)P3 (Simpson and Parsons, *Exp. Cell Res.*, 2001, 264, 29-41). Furthermore, augmentation of the effects of other PI3K-mediated signalling events is believed to contribute to a variety of cancers, for example by activation of Akt (Nicholson and Anderson, *Cellular Signalling*, 2002, 14, 381-395).

In addition to a role in mediating proliferative and survival signalling in tumour cells, there is also good evidence that Class Ia PI3K enzymes will also contribute to tumorigenesis via its function in tumour-associated stromal cells. For example, PI3K signalling is known to play an important role in mediating angiogenic events in endothelial cells in response to pro-angiogenic factors such as VEGF (Abid et al., *Arterioscler. Thromb. Vasc. Biol.*, 2004, 24, 294-300). As Class I PI3K enzymes are also involved in motility and migration (Sawyer, *Expert Opinion Investig. Drugs*, 2004, 13, 1-19), PI3K inhibitors should provide therapeutic benefit via inhibition of tumour cell invasion and metastasis.

In addition, Class I PI3K enzymes play an important role in the regulation of immune cells with PI3K activity contributing to pro-tumorigenic effects of inflammatory cells (Coussens and Werb, *Nature*, 2002, 420, 860-867).

These findings suggest that pharmacological inhibitors of Class I PI3K enzymes should be of therapeutic value for treatment of the various forms of the disease of cancer comprising solid tumours such as carcinomas and sarcomas and the leukaemias and lymphoid malignancies. In particular, inhibitors of Class I PI3K enzymes should be of therapeutic value for treatment of, for example, cancer of the breast, colorectum, lung (including small cell lung cancer, non-small cell lung cancer and bronchioalveolar cancer) and prostate, and of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

Generally, investigators have explored the physiological and pathological roles of the PI3K enzyme family using the PI3K inhibitors LY294002 and wortmanin. Although use of those compounds may suggest a role for PI3K in a cellular event, they are not sufficiently selective within the PI3K family to allow dissection of the individual roles of the family members. For this reason, more potent and selective pharmaceutical PI3K inhibitors would be useful to allow a more complete understanding of PI3K function and to provide useful therapeutic agents.

In addition to tumorigenesis, there is evidence that Class I PI3K enzymes play a role in other diseases (Wymann et al., *Trends in Pharmaceutical Science*, 2003, 24, 366-376). Both Class Ia PI3K enzymes and the single Class Ib enzyme have important roles in cells of the immune system (Koyasu, *Nature Immunology*, 2003, 4, 313-319) and thus they are therapeutic targets for inflammatory and allergic indications. Inhibition of PI3K is also useful to treat cardiovascular disease via anti-inflammatory effects or directly by affecting cardiac myocytes (Prasad et al., *Trends in Cardiovascular Medicine*, 2003, 13, 206-212). Thus inhibitors of Class I PI3K enzymes are expected to be of value in the prevention and treatment of a wide variety of diseases in addition to cancer.

It is disclosed in International Patent Application WO 2004/048365 that certain pyrimidine derivatives possess PI3K enzyme inhibitory activity and are useful in the treatment of cancer. The disclosure focuses on arylamino- and heteroarylamino-substituted pyrimidines. The scope of disclosure does not embrace 2-aryl substituted pyrimidines.

It is disclosed in European Patent Application 1 277 738 that a variety of structures possess PI3K enzyme inhibitory activity and are useful in the treatment of cancer. The disclosure includes mention of 4-morpholino-substituted bicyclic heteroaryl compounds such as quinazoline and pyrido[3,2-d]pyrimidine derivatives and 4-morpholino-substituted tricyclic heteroaryl compounds such as compounds described as pyrido[3',2':4,5]furo[3,2-d]pyrimidine derivatives. The scope of disclosure does not embrace monocyclic pyrimidine derivatives.

We have now found that surprisingly certain pyrimidine derivatives possess potent anti-tumour activity, being useful in inhibiting the uncontrolled cellular proliferation which arises from malignant disease. Without wishing to imply that the compounds disclosed in the present invention possess pharmacological activity only by virtue of an effect on a single biological process, it is believed that the compounds provide an anti-tumour effect by way of inhibition of Class I PI3K enzymes, particularly by way of inhibition of the Class Ia PI3K enzymes and/or the Class Ib PI3K enzyme, more particularly by way of inhibition of the Class Ia PI3K enzymes.

The compounds of the present invention are also useful in inhibiting the uncontrolled cellular proliferation which arises from various non-malignant diseases such as inflammatory diseases (for example rheumatoid arthritis and inflammatory bowel disease), fibrotic diseases (for example hepatic cirrhosis and lung fibrosis), glomerulonephritis, multiple sclerosis, psoriasis, benign prostatic hypertrophy (BPH), hypersensitivity reactions of the skin, blood vessel diseases (for example atherosclerosis and restenosis), allergic asthma, insulin-dependent diabetes, diabetic retinopathy and diabetic nephropathy.

Generally, the compounds of the present invention possess potent inhibitory activity against Class I PI3K enzymes, particularly against Class Ia PI3K enzymes, whilst possessing less potent inhibitory activity against tyrosine kinase enzymes such as the receptor tyrosine kinases, for example EGF receptor tyrosine kinase and/or VEGF receptor tyrosine kinase, or against non-receptor tyrosine kinases such as Src. Furthermore, certain compounds of the present invention, possess substantially better potency against Class I PI3K enzymes, particularly against Class Ia PI3K enzymes, than against EGF receptor tyrosine kinase or VEGF receptor tyrosine kinase or Src non-receptor tyrosine kinase. Such compounds possess sufficient potency against Class I PI3K enzymes that they may be used in an amount sufficient to inhibit Class I PI3K enzymes, particularly to inhibit Class Ia PI3K enzymes, whilst demonstrating little activity against EGF receptor tyrosine kinase or VEGF receptor tyrosine kinase or Src non-receptor tyrosine kinase.

According to one aspect of the invention there is provided a pyrimidine derivative of the Formula I

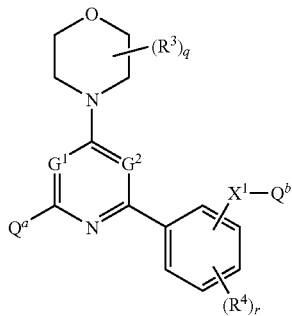

I wherein:—

$Q^a$ is a heteroaryl group that optionally bears 1, 2, 3 or 4 substituents, which may be the same or different, selected from halogeno, trifluoromethyl, cyano, isocyano, nitro, hydroxy, mercapto, amino, formyl, carboxy, carbamoyl, ureido, (1-8C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N'-(1-6C)alkylureido, N',N'-di-[(1-6C)alkyl]ureido, N-(1-6C)alkylureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$Q^2$-$X^2$— wherein $X^2$ is a direct bond or is selected from O, S, SO, $SO_2$, $N(R^5)$, CO, $CH(OR^5)$, $CON(R^5)$, $N(R^5)CO$, $N(R^5)CON(R^5)$, $SO_2N(R^5)$, $N(R^5)SO_2$, $OC(R^5)_2$, $SC(R^5)_2$ and $N(R^5)C(R^5)_2$, wherein $R^5$ is hydrogen or (1-8C)alkyl, and $Q^2$ is aryl, aryl-(1-6C)alkyl, (3-8C)cycloalkyl, (3-8C)cycloalkyl-(1-6C)alkyl, (3-8C)cycloalkenyl, (3-8C)cycloalkenyl-(1-6C)alkyl, heteroaryl, heteroaryl-(1-6C)alkyl, heterocyclyl or heterocyclyl-(1-6C)alkyl, or $Q^a$ bears a (1-3C)alkylenedioxy substituent, and wherein any CH, $CH_2$ or $CH_3$ group within a substituent on $Q^a$ optionally bears on each said CH, $CH_2$ or $CH_3$ group one or more halogeno or (1-8C)alkyl substituents and/or a substituent selected from hydroxy, mercapto, amino, cyano, carboxy, carbamoyl, ureido, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylureido, N'-(1-6C)alkylureido, N',N'-di-[(1-6C)alkyl]ureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—$X^3$-$Q^3$ wherein $X^3$ is a direct bond or is selected from O, S, SO, $SO_2$, $N(R^6)$, CO, $CH(OR^6)$, $CON(R^6)$, $N(R^6)CO$, $N(R^6)CON(R^6)$, $SO_2N(R^6)$, $N(R^6)SO_2$, $C(R^6)_2O$, $C(R^6)_2S$ and $C(R^6)_2N(R^6)$, wherein $R^6$ is hydrogen or (1-6C)alkyl, and $Q^3$ is aryl, aryl-(1-6C)alkyl, (3-8C)cycloalkyl, (3-8C)cycloalkyl-(1-6C)alkyl, (3-8C)cycloalkenyl, (3-8C)cycloalkenyl-(1-6C)alkyl, heteroaryl, heteroaryl-(1-6C)alkyl, heterocyclyl or heterocyclyl-(1-6C)alkyl, and wherein any aryl, (3-8C)cycloalkyl, (3-8C)cycloalkenyl, heteroaryl or heterocyclyl group within a substituent on $Q^a$ optionally bears 1, 2 or 3 substituents, which may be the same or different, selected from halogeno, trifluoromethyl, cyano, nitro, hydroxy, amino, carboxy, carbamoyl, ureido, (1-8C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (2-6C)alkanoylamino, N-(1-6C)alkyl-(2-6C)alkanoylamino, N-(1-6C)alkylureido, N'-(1-6C)alkylureido, N',N'-di-[(1-6C)alkyl]ureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—$X^4$—$R^7$ wherein $X^4$ is a direct bond or is selected from O and $N(R^8)$, wherein $R^8$ is hydrogen or (1-8C)alkyl, and $R^7$ is halogeno-(1-6C)alkyl, hydroxy-(1-6C)alkyl, mercapto-(1-6C)alkyl, (1-6C)alkoxy-(1-6C)alkyl, (1-6C)alkylthio-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, (1-6C)alkoxycarbonylamino-(1-6C)alkyl, N-(1-6C)alkylureido-(1-6C)alkyl, N'-(1-6C)alkylureido-(1-6C)alkyl, N',N'-di-[(1-6C)alkyl]ureido-(1-6C)alkyl, N,N'-di-[(1-6C)alkyl]ureido-(1-6C)alkyl or N,N',N'-tri-[(1-6C)alkyl]ureido-(1-6C)alkyl, or from a group of the formula:

—$X^1$-$Q^4$ wherein $X^5$ is a direct bond or is selected from O, CO and $N(R^9)$, wherein $R^9$ is hydrogen or (1-8C)alkyl, and $Q^4$ is aryl, aryl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, hydroxy, (1-8C)alkyl and (1-6C)alkoxy, and wherein any heterocyclyl group within a substituent on $Q^a$ optionally bears 1 or 2 oxo or thioxo substituents, and wherein adjacent carbon atoms in any (2-6C)alkylene chain within a substituent on $Q^a$ are optionally separated by the insertion into the chain of a group selected from O, S, SO, $SO_2$, $N(R^{10})$, CO, $CH(OR^{10})$, $CON(R^{10})$, $N(R^{10})CO$, $N(R^{10})CON(R^{10})$, $SO_2N(R^{10})$, $N(R^{10})SO_2$, CH=CH and C≡C wherein $R^{10}$ is hydrogen or (1-8C)alkyl;

$G^1$ is N or $C(R^1)$ wherein $R^1$ is hydrogen or (1-8C)alkyl, and $G^2$ is N or $C(R^2)$ wherein $R^2$ is hydrogen or (1-8C)alkyl, provided that one of $G^1$ and $G^2$ is N, and if $G^1$ is N then $G^2$ is $C(R^2)$, or if $G^2$ is N then $G^1$ is $C(R^1)$;

q is 0, 1, 2, 3 or 4;

each $R^3$ group, which may be the same or different, is (1-8C)alkyl or a group of the formula:

$X^6$—$R^{11}$ wherein $X^6$ is a direct bond or is selected from O and $N(R^{12})$, wherein $R^{12}$ is hydrogen or (1-8C)alkyl, and $R^{11}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl or (2-6C)alkanoylamino-(1-6C)alkyl;

r is 0, 1 or 2;

each $R^4$ group, which may be the same or different, is selected from halogeno, trifluoromethyl, cyano, nitro, hydroxy, mercapto, amino, carboxy, carbamoyl, ureido, (1-8C)alkyl, (2-8C)alkenyl, (2-8C)alkynyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N'-(1-6C)alkylureido, N',N'-di-[(1-6C)alkyl]ureido, N-(1-6C)alkylureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino;

$X^1$ is selected from CO, $N(R^{13})CO$, $CON(R^{13})$, $N(R^{13})CON(R^{13})$, $N(R^{13})COC(R^{13})_2O$, $N(R^{13})COC(R^{13})_2S$, $N(R^{13})COC(R^{13})_2N(R^{13})$ and $N(R^{13})COC(R^{13})_2N(R^{13})CO$, wherein $R^{13}$ is hydrogen or (1-8C)alkyl; and $Q^b$ is (1-8C)alkyl, (2-8C)alkenyl, (2-8C)alkynyl, halogeno-(1-6C)alkyl, hydroxy-(1-6C)alkyl, mercapto-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (1-6C)alkylthio-(1-6C)alkyl, (1-6C)alkylsulphinyl-(1-6C)alkyl, (1-6C)alkylsulphonyl-(1-6C)alkyl, (2-6C)alkanoylamino-(1-6C)alkyl, N-(1-6C)alkyl-(2-6C)alkanoylamino-(1-6C)alkyl, (1-6C)alkoxycarbonylamino-(1-6C)alkyl, N-(1-6C)alkylureido-(1-6C)alkyl, N'-(1-6C)alkylureido-(1-6C)alkyl, N',N'-di-[(1-6C)alkyl]ureido-(1-6C)alkyl, N,N'-di-[(1-6C)alkyl]ureido-(1-6C)alkyl, N,N',N'-tri-[(1-6C)alkyl]ureido-(1-6C)alkyl, (1-6C)alkanesulphonylamino-(1-6C)alkyl or N-(1-6C)alkyl-(1-6C)alkanesulphonylamino-(1-6C)alkyl, or $Q^b$ is aryl, aryl-(1-6C)alkyl, (3-8C)cycloalkyl, (3-8C)cycloalkyl-(1-6C)alkyl, (3-8C)cycloalkenyl, (3-8C)cycloalkenyl-(1-6C)alkyl, heteroaryl, heteroaryl-(1-6C)alkyl, heterocyclyl or heterocyclyl-(1-6C)alkyl, and wherein any CH, $CH_2$ or $CH_3$ group within the $Q^b$ group optionally bears on each said CH, $CH_2$ or $CH_3$ group one or more halogeno or (1-8C)alkyl substituents and/or a substituent selected from hydroxy, mercapto, amino, cyano, carboxy, carbamoyl, ureido, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N'-(1-6C)alkylureido, N',N'-di-[(1-6C)alkyl]ureido, N-(1-6C)alkylureido, N,N'-di-[(1-6C)alkyl]ureido, N,N',N'-tri-[(1-6C)alkyl]ureido, N-(1-6C)alkylsulphamoyl, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, and wherein any aryl, (3-8C)cycloalkyl, (3-8C)cycloalkenyl, heteroaryl or heterocyclyl group within the $Q^b$ group optionally bears 1, 2 or 3 substituents, which may be the same or different, selected from halogeno, trifluoromethyl, cyano, nitro, hydroxy, amino, carboxy, carbamoyl, ureido, (1-8C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (2-6C)alkanoylamino, N-(1-6C)alkyl-(2-6C)alkanoylamino, N'-(1-6C)alkylureido, N',N'-di-[(1-6C)alkyl]ureido, N-(1-6C)alkylureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—$X^7$—$R^{14}$ wherein $X^7$ is a direct bond or is selected from O and $N(R^5)$, wherein $R^{15}$ is hydrogen or (1-8C)alkyl, and $R^{14}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl, or from a group of the formula:

—$X^8$-$Q^5$ wherein $X^8$ is a direct bond or is selected from O, CO and $N(R^{17})$, wherein $R^{17}$ is hydrogen or (1-8C)alkyl, and $Q^5$ is aryl, aryl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, hydroxy, (1-8C)alkyl and (1-6C)alkoxy, and wherein any heterocyclyl group within the $Q^b$ group optionally bears 1 or 2 oxo or thioxo substituents, and wherein adjacent carbon atoms in any (2-6C)alkylene chain within the $Q^b$ group are optionally separated by the insertion into the chain of a group selected from O, S, SO, $SO_2$, $N(R^{16})$, $N(R^{16})CO$, $CON(R^{16})$, $N(R^{16})CON(R^{16})$, CO, $CH(OR^{16})$, $N(R^{16})SO_2$, $SO_2N(R^{16})$, CH=CH and C≡C wherein $R^{16}$ is hydrogen or (1-8C)alkyl;

or a pharmaceutically-acceptable salt, solvate or pro-drug thereof.

In this specification the generic term "(1-8C)alkyl" includes both straight-chain and branched-chain alkyl groups such as propyl, isopropyl and tert-butyl, and also (3-8C)cycloalkyl groups such as cyclopropyl, cyclobutyl, cyclopentyl, cyclohexyl and cycloheptyl, and also (3-6C)cycloalkyl-(1-2C)alkyl groups such as cyclopropylmethyl, 2-cyclopropylethyl, cyclobutylmethyl, 2-cyclobutylethyl, cyclopentylmethyl, 2-cyclopentylethyl, cyclohexylmethyl and 2-cyclohexylethyl. However references to individual alkyl groups such as "propyl" are specific for the straight-chain version only, references to individual branched-chain alkyl groups such as "isopropyl" are specific for the branched-chain version only and references to individual cycloalkyl groups such as "cyclopentyl" are specific for that 5-membered ring only. An analogous convention applies to other generic terms, for example (1-6C)alkoxy includes (3-6C)cycloalkyloxy groups and (3-5C)cycloalkyl-(1-2C)alkoxy groups, for example methoxy, ethoxy, propoxy, isopropoxy, cyclopropyloxy, cyclobutyloxy, cyclopentyloxy, cyclohexyloxy, cyclopropylmethoxy, 2-cyclopropylethoxy, cyclobutylmethoxy, 2-cyclobutylethoxy and cyclopentylmethoxy; (1-6C)alkylamino includes (3-6C)cycloalkylamino groups and (3-5C)cycloalkyl-(1-2C)alkylamino groups, for example methylamino, ethylamino, propylamino, cyclopropylamino, cyclobutylamino, cyclohexylamino, cyclopropylmethylamino, 2-cyclopropylethylamino, cyclobutylmethylamino, 2-cyclobutylethylamino and cyclopentylmethylamino; and di-[(1-6Calkyl]amino includes di-[(3-6C)cycloalkyl]amino groups and di-[(3-5C)cycloalkyl-(1-2C)alkyl]amino groups, for example dimethylamino, diethylamino, dipropylamino, N-cyclopropyl-N-methylamino, N-cyclobutyl-N-methylamino, N-cyclohexyl-N-ethylamino, N-cyclopropylmethyl-N-methylamino, N-(2-cyclopropylethyl)-N-methylamino and N-cyclopentylmethyl-N-methylamino.

It is to be understood that, insofar as certain of the compounds of Formula I defined above may exist in optically active or racemic forms by virtue of one or more asymmetric carbon atoms, the invention includes in its definition any such optically active or racemic form which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

It is to be understood that certain compounds of Formula I defined above may exhibit the phenomenon of tautomerism. In particular, tautomerism may affect heterocyclic groups within the $Q^a$ and $Q^b$ groups that bear 1 or 2 oxo or thioxo substituents. It is to be understood that the present invention includes in its definition any such tautomeric form, or a mixture thereof, which possesses the above-mentioned activity and is not to be limited merely to any one tautomeric form utilised within the formulae drawings or named in the Examples.

It is to be understood that the —$X^1$-$Q^b$ group may be located at any available position on the phenyl group that, when $G^2$ is N, is located at the 2-position on the pyrimidine ring. Conveniently, the —$X^1$-$Q^b$ group is located at the 3- or 4-position on said phenyl group. More conveniently, the —$X^1$-$Q^b$ group is located at the 3-position on said phenyl group.

It is further to be understood that any substituent that is present on the $Q^a$ group may be located at any available position on said $Q^a$ group. When multiple substituents on the $Q^a$ group are present, said substituents may be the same or different. Conveniently, there is a single substituent on the $Q^a$ group.

It is further to be understood that any $R^3$ group that may be present on the morpholinyl group that is located at the 6-position on the pyrimidine ring may be located at any available position on said morpholinyl group. Conveniently, there is a single $R^3$ group. More conveniently, no $R^3$ group is present (q=0).

It is further to be understood that any $R^4$ group that may be present on the phenyl group that, when $G^2$ is N, is located at the 2-position on the pyrimidine ring may be located at any available position on said phenyl group. Conveniently, there is a single $R^4$ group. More conveniently, no $R^4$ group is present (r=0).

Suitable values for the generic radicals referred to above include those set out below.

A suitable value for any one of the 'Q' groups ($Q^2$ to $Q^5$ and $Q^b$) when it is aryl or for the aryl group within a 'Q' group is, for example, phenyl or naphthyl, preferably phenyl.

A suitable value for any one of the 'Q' groups ($Q^2$, $Q^3$ and $Q^b$) when it is (3-8C)cycloalkyl or for the (3-8C)cycloalkyl group within a 'Q' group is, for example, cyclopropyl, cyclobutyl, cyclopentyl, cyclohexyl, cycloheptyl, bicyclo [2.2.1]heptyl or cyclooctyl and a suitable value for any one of the 'Q' groups ($Q^2$, $Q^3$ and $Q^b$) when it is (3-8C)cycloalkenyl or for the (3-8C)cycloalkenyl group within a 'Q' group is, for example, cyclobutenyl, cyclopentenyl, cyclohexenyl, cycloheptenyl or cyclooctenyl.

A suitable value for any one of the 'Q' groups ($Q^a$, $Q^2$ to $Q^5$ and $Q^b$) when it is heteroaryl or for the heteroaryl group within a 'Q' group is, for example, an aromatic 5- or 6-membered monocyclic ring or a 9- or 10-membered bicyclic ring with up to five ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl or naphthyridinyl.

A suitable value for any one of the 'Q' groups ($Q^2$ to $Q^5$ and $Q^b$) when it is heterocyclyl or for the heterocyclyl group within a 'Q' group is, for example, a non-aromatic saturated or partially saturated 3 to 10 membered monocyclic or bicyclic ring with up to five heteroatoms selected from oxygen, nitrogen and sulphur, for example oxiranyl, oxetanyl, tetrahydrofuranyl, tetrahydropyranyl, oxepanyl, tetrahydrothienyl, 1,1-dioxotetrahydrothienyl, tetrahydrothiopyranyl, 1,1-dioxotetrahydrothiopyranyl, azetidinyl, pyrrolinyl, pyrrolidinyl, imidazolinyl, imidazolidinyl, pyrazolinyl, pyrazolidinyl, morpholinyl, tetrahydro-1,4-thiazinyl, 1,1-dioxotetrahydro-1,4-thiazinyl, piperidinyl, homopiperidinyl, piperazinyl, homopiperazinyl, 2-azabicyclo[2.2.1]heptyl, quinuclidinyl, chromanyl, isochromanyl, indolinyl, isoindolinyl, dihydropyridinyl, tetrahydropyridinyl, dihydropyrimidinyl or tetrahydropyrimidinyl, preferably tetrahydrofuranyl, tetrahydropyranyl, tetrahydrothiopyranyl, pyrrolinyl, pyrrolidinyl, morpholinyl, piperidinyl, piperazinyl, indolinyl or isoindolinyl. A suitable value for such a group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 4-oxo-1,4-dihydropyridinyl, 2,5-dioxopyrrolidinyl, 2,5-dioxoimidazolidinyl or 2,6-dioxopiperidinyl.

A suitable value for a 'Q' group when it is heteroaryl-(1-6C)alkyl is, for example, heteroarylmethyl, 2-heteroarylethyl and 3-heteroarylpropyl. The invention comprises corresponding suitable values for 'Q' groups when, for example, rather than a heteroaryl-(1-6C)alkyl group, an aryl-(1-6C)alkyl, (3-8C)cycloalkyl-(1-6C)alkyl, (3-8C)cycloalkenyl-(1-6C)alkyl or heterocyclyl-(1-6C)alkyl group is present.

Suitable values for any of the 'R' groups ($R^1$ to $R^{17}$), or for various groups within a $Q^a$ substituent or within an $R^3$ or $R^4$ substituent, or for $Q^b$, or for various groups within $Q^b$ include:—

| | |
|---|---|
| for halogeno | fluoro, chloro, bromo and iodo; |
| for (1-8C)alkyl: | methyl, ethyl, propyl, isopropyl, tert-butyl, cyclobutyl, cyclohexyl, cyclohexylmethyl and 2-cyclopropylethyl; |
| for (2-8C)alkenyl: | vinyl, isopropenyl, allyl and but-2-enyl; |
| for (2-8C)alkynyl: | ethynyl, 2-propynyl and but-2-ynyl; |
| for (1-6C)alkoxy: | methoxy, ethoxy, propoxy, isopropoxy and butoxy; |

| | |
|---|---|
| for (2-6C)alkenyloxy: | vinyloxy and allyloxy; |
| for (2-6C)alkynyloxy: | ethynyloxy and 2-propynyloxy; |
| for (1-6C)alkylthio: | methylthio, ethylthio and propylthio; |
| for (1-6C)alkylsulphinyl: | methylsulphinyl and ethylsulphinyl; |
| for (1-6C)alkylsulphonyl: | methylsulphonyl and ethylsulphonyl; |
| for (1-6C)alkylamino: | methylamino, ethylamino, propylamino, isopropylamino and butylamino; |
| for di-[(1-6C)alkyl]amino: | dimethylamino, diethylamino, N-ethyl-N-methylamino and diisopropylamino; |
| for (1-6C)alkoxycarbonyl: | methoxycarbonyl, ethoxycarbonyl, propoxycarbonyl and tert-butoxycarbonyl; |
| for N-(1-6C)alkylcarbamoyl: | N-methylcarbamoyl, N-ethylcarbamoyl and N-propylcarbamoyl; |
| for N,N-di-[(1-6C)alkyl]carbamoyl: | N,N-dimethylcarbamoyl, N-ethyl-N-methylcarbamoyl and N,N-diethylcarbamoyl; |
| for (2-6C)alkanoyl: | acetyl, propionyl and isobutyryl; |
| for (2-6C)alkanoyloxy: | acetoxy and propionyloxy; |
| for (2-6C)alkanoylamino: | acetamido and propionamido; |
| for N-(1-6C)alkyl-(2-6C)alkanoylamino: | N-methylacetamido and N-methylpropionamido; |
| for (3-6C)alkenoylamino: | acrylamido, methacrylamido and crotonamido; |
| for N-(1-6C)alkyl-(3-6C)alkenoylamino: | N-methylacrylamido and N-methylcrotonamido; |
| for (3-6C)alkynoylamino: | propiolamido; |
| for N-(1-6C)alkyl-(3-6C)alkynoylamino: | N-methylpropiolamido; |
| for N'-(1-6C)alkylureido: | N'-methylureido and N'-ethylureido; |
| for N',N'-di-[(1-6C)alkyl]ureido: | N',N'-dimethylureido and N'-methyl-N'-ethylureido; |
| for N-(1-6C)alkylureido: | N-methylureido and N-ethylureido; |
| for N,N'-di-[(1-6C)alkyl]ureido: | N,N'-dimethylureido, N-methyl-N'-ethylureido and N-ethyl-N'-methylureido; |
| for N,N',N'-di-[(1-6C)alkyl]ureido: | N,N',N'-trimethylureido, N-ethyl-N',N'-dimethylureido and N-methyl-N',N'-diethylureido; |
| for N-(1-6C)alkylsulphamoyl: | N-methylsulphamoyl and N-ethylsulphamoyl; |
| for N,N-di-[(1-6C)alkyl]sulphamoyl: | N,N-dimethylsulphamoyl; |
| for (1-6C)alkanesulphonylamino: | methanesulphonylamino and ethanesulphonylamino; |
| for N-(1-6C)alkyl-(1-6C)alkanesulphonylamino: | N-methylmethanesulphonylamino and N-methylethanesulphonylamino; |
| for halogeno-(1-6C)alkyl: | chloromethyl, 2-fluoroethyl, 2-chloroethyl, 1-chloroethyl, 2,2-difluoroethyl, 2,2,2-trifluoroethyl, 3-fluoropropyl, 3-chloropropyl, 3,3-difluoropropyl and 3,3,3-trifluoropropyl; |
| for hydroxy-(1-6C)alkyl: | hydroxymethyl, 2-hydroxyethyl, 1-hydroxyethyl and 3-hydroxypropyl; |
| for mercapto-(1-6C)alkyl: | mercaptomethyl, 2-mercaptoethyl, 1-mercaptoethyl and 3-mercaptopropyl; |
| for (1-6C)alkoxy-(1-6C)alkyl: | methoxymethyl, ethoxymethyl, 1-methoxyethyl, 2-methoxyethyl, 2-ethoxyethyl and 3-methoxypropyl; |
| for (1-6C)alkylthio-(1-6C)alkyl: | methylthiomethyl, ethylthiomethyl, 2-methylthioethyl, 1-methylthioethyl and 3-methylthiopropyl; |
| for (1-6C)alkylsulphinyl-(1-6C)alkyl: | methylsulphinylmethyl, ethylsulphinylmethyl, 2-methylsulphinylethyl, 1-methylsulphinylethyl and 3-methylsulphinylpropyl; |
| for (1-6C)alkylsulphonyl-(1-6C)alkyl: | methylsulphonylmethyl, ethylsulphonylmethyl, 2-methylsulphonylethyl, 1-methylsulphonylethyl and 3-methylsulphonylpropyl; |
| for cyano-(1-6C)alkyl: | cyanomethyl, 2-cyanoethyl, 1-cyanoethyl and 3-cyanopropyl; |
| for amino-(1-6C)alkyl: | aminomethyl, 2-aminoethyl, 1-aminoethyl, 3-aminopropyl, 1-aminopropyl and 5-aminopropyl; |
| for (1-6C)alkylamino-(1-6C)alkyl: | methylaminomethyl, ethylaminomethyl, 1-methylaminoethyl, 2-methylaminoethyl, 2-ethylaminoethyl and 3-methylaminopropyl; |
| for di-[(1-6C)alkyl]amino-(1-6C)alkyl: | dimethylaminomethyl, diethylaminomethyl, 1-dimethylaminoethyl, 2-dimethylaminoethyl and 3-dimethylaminopropyl; |
| for (2-6C)alkanoylamino-(1-6C)alkyl: | acetamidomethyl, propionamidomethyl, 2-acetamidoethyl and 1-acetamidoethyl; |
| for N-(1-6C)alkyl-(2-6C)alkanoylamino-(1-6C)alkyl: | N-methylacetamidomethyl, N-methylpropionamidomethyl, 2-(N-methylacetamido)ethyl and 1-(N-methylacetamido)ethyl; |
| for (1-6C)alkoxycarbonylamino-(1-6C)alkyl: | methoxycarbonylaminomethyl, ethoxycarbonylaminomethyl, tert-butoxycarbonylaminomethyl and 2-methoxycarbonylaminoethyl; |
| for N'-(1-6C)alkylureido-(1-6C)alkyl: | N'-methylureidomethyl, 2-(N'-methylureido)ethyl and 1-(N'-methylureido)ethyl; |

-continued

| | |
|---|---|
| for N',N'-di-[(1-6C)alkyl]ureido-(1-6C)alkyl: | N',N'-dimethylureidomethyl, 2-(N',N'-dimethylureido)ethyl and 1-(N',N'-dimethylureido)ethyl; |
| for N-(1-6C)alkylureido-(1-6C)alkyl: | N-methylureidomethyl, 2-(N-methylureido)ethyl and 1-(N-methylureido)ethyl; |
| for N,N'-di-[(1-6C)alkyl]ureido-(1-6C)alkyl: | N,N'-dimethylureidomethyl, 2-(N,N'-dimethylureido)ethyl and 1-(N,N'-dimethylureido)ethyl; |
| for N,N',N'-di-[(1-6C)alkyl]ureido-(1-6C)alkyl: | N',N',N'-trimethylureidomethyl, 2-(N,N',N'-trimethylureido)ethyl and 1-(N,N',N'-trimethylureido)ethyl; |
| for (1-6C)alkanesulphonylamino-(1-6C)alkyl: | methanesulphonylaminomethyl, 2-(methanesulphonylamino)ethyl and 1-(methanesulphonylamino)ethyl; and |
| for N-(1-6C)alkyl-(1-6C)alkanesulphonylamino-(1-6C)alkyl: | N-methylmethanesulphonylaminomethyl, 2-(N-methylmethanesulphonylamino)ethyl and 1-(N-methylmethanesulphonylamino)ethyl. |

A suitable value for a (1-3C)alkylenedioxy substituent on $Q^a$ is, for example, methylenedioxy, ethylidenedioxy, isopropylidenedioxy or ethylenedioxy and the oxygen atoms thereof occupy adjacent ring positions.

When, as defined hereinbefore, a $Q^a$ substituent forms a group of the formula $Q^2$-$X^2$— and, for example, $X^2$ is a $OC(R^5)_2$ linking group, it is the carbon atom, not the oxygen atom, of the $OC(R^5)_2$ linking group which is attached to the $Q^a$ ring and the oxygen atom is attached to the $Q^2$ group. Similarly, when, for example a $CH_3$ group within a $Q^a$ substituent bears a group of the formula —$X^3$-$Q^3$ and, for example, $X^3$ is a $C(R^6)_2O$ linking group, it is the carbon atom, not the oxygen atom, of the $C(R^6)_2O$ linking group which is attached to the $CH_3$ group and the oxygen atom is linked to the $Q^3$ group.

As defined hereinbefore, adjacent carbon atoms in any (2-6C)alkylene chain within a $Q^a$ substituent may be optionally separated by the insertion into the chain of a group such as O, $CON(R^{10})$ or C≡C. For example, insertion of an O atom into the alkylene chain within a 4-methoxybutoxy group gives rise to, for example, a 2-(2-methoxyethoxy)ethoxy group, for example, insertion of a C≡C group into the ethylene chain within a 2-hydroxyethoxy group gives rise to a 4-hydroxybut-2-ynyloxy group and, for example, insertion of a CONH group into the ethylene chain within a 3-methoxypropoxy group gives rise to, for example, a 2-(2-methoxyacetamido)ethoxy group.

When, as defined hereinbefore, any CH, $CH_2$ or $CH_3$ group within a $Q^a$ substituent optionally bears on each said CH, $CH_2$ or $CH_3$ group one or more halogeno or (1-8C)alkyl substituents, there is suitably 1 halogeno or (1-8C)alkyl substituent present on each said CH group, there are suitably 1 or 2 such substituents present on each said $CH_2$ group and there are suitably 1, 2 or 3 such substituents present on each said $CH_3$ group.

When, as defined hereinbefore, any CH, $CH_2$ or $CH_3$ group within a $Q^a$ substituent optionally bears on each said CH, $CH_2$ or $CH_3$ group a substituent as defined hereinbefore, suitable $Q^a$ substituents so formed include, for example, hydroxy-substituted (1-8C)alkyl groups such as hydroxymethyl, 1-hydroxyethyl and 2-hydroxyethyl, hydroxy-substituted (1-6C) alkoxy groups such as 2-hydroxypropoxy and 3-hydroxypropoxy, (1-6C)alkoxy-substituted (1-6C)alkoxy groups such as 2-methoxyethoxy and 3-ethoxypropoxy, hydroxy-substituted amino-(2-6C)alkoxy groups such as 3-amino-2-hydroxypropoxy, hydroxy-substituted (1-6C) alkylamino-(2-6C)alkoxy groups such as 2-hydroxy-3-methylaminopropoxy, hydroxy-substituted di-[(1-6C)alkyl] amino-(2-6C)alkoxy groups such as 3-dimethylamino-2-hydroxypropoxy, hydroxy-substituted amino-(2-6C) alkylamino groups such as 3-amino-2-hydroxypropylamino, hydroxy-substituted (1-6C)alkylamino-(2-6C)alkylamino groups such as 2-hydroxy-3-methylaminopropylamino and hydroxy-substituted di-[(1-6C)alkyl]amino-(2-6C)alkylamino groups such as 3-dimethylamino-2-hydroxypropylamino.

It is further to be understood that when, as defined hereinbefore, any CH, $CH_2$ or $CH_3$ group within a $Q^a$ substituent optionally bears on each said CH, $CH_2$ or $CH_3$ group a substituent as defined hereinbefore, such an optional substituent may be present on a CH, $CH_2$ or $CH_3$ group within the hereinbefore defined substituents that may be present on an aryl, heteroaryl or heterocyclyl group within a $Q^a$ substituent. For example, if a $Q^a$ substituent includes an aryl or heteroaryl group that is substituted by a (1-8C)alkyl group, the (1-8C) alkyl group may be optionally substituted on a CH, $CH_2$ or $CH_3$ group therein by one of the hereinbefore defined substituents therefor. For example, if the $Q^a$ substituent includes a heteroaryl group that is substituted by, for example, a (1-6C) alkylamino-(1-6C)alkyl group, the terminal $CH_3$ group of the (1-6C)alkylamino group may be further substituted by, for example, a (1-6C)alkylsulphonyl group or a (2-6C)alkanoyl group. For example, the $Q^a$ substituent may be a heteroaryl group such as a thienyl group that is substituted by a N-(2-methylsulphonylethyl)aminomethyl group such that the $Q^a$ substituent is, for example, a 5-[N-(2-methylsulphonylethyl) aminomethyl]thien-2-yl group. Further, for example, if a $Q^a$ substituent includes a heterocyclyl group such as a piperidinyl or piperazinyl group that is substituted on a nitrogen atom thereof by, for example, a (2-6C)alkanoyl group, the terminal $CH_3$ group of the (2-6C)alkanoyl group may be further substituted by, for example, a di-[(1-6C)alkyl]amino group. For example, the $Q^a$ substituent may be a N-(2-dimethylaminoacetyl)piperidin-4-yl group or a 4-(2-dimethylaminoacetyl)piperazin-1-yl group.

Similar considerations apply to the attachments and substitutions within the —$X^1$-$Q^b$ group. For example, when, as defined hereinbefore, any CH, $CH_2$ or $CH_3$ group within a $Q^b$ group optionally bears on each said CH, $CH_2$ or $CH_3$ group a substituent as defined hereinbefore, suitable $Q^b$ groups so formed include, for example, hydroxy-substituted amino-(1-6C)alkyl groups such as 1-amino-2-hydroxyethyl or 1-amino-2-hydroxypropyl, an (1-6C)alkoxy-substituted amino-(1-6C)alkyl groups such as 1-amino-2-methoxyethyl, a (1-6C)alkylamino-(1-6C)alkyl-substituted heteroaryl group such as a 5-[N-(2-methylsulphonylethyl)aminomethyl]thien-2-yl group, and a (2-6C)alkanoyl-substituted heterocyclic group such as a N-(2-dimethylaminoacetyl)piperidin-4-yl group or a 4-(2-dimethylaminoacetyl)piperazin-1-yl group.

A suitable pharmaceutically-acceptable salt of a compound of the Formula I is, for example, an acid-addition salt of a compound of the Formula I, for example an acid-addition salt with an inorganic or organic acid such as hydrochloric, hydrobromic, sulphuric, trifluoroacetic, citric or maleic acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine. A further suitable pharmaceutically-acceptable salt of a compound of the Formula I is, for example, a salt formed within the human or animal body after administration of a compound of the Formula I.

A suitable pharmaceutically-acceptable solvate of a compound of the Formula I is, for example, a hydrate such as a hemi-hydrate, a mono-hydrate, a di-hydrate or a tri-hydrate or an alternative quantity thereof.

The compounds of the invention may be administered in the form of a pro-drug, that is a compound that is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the Formula I and in vivo cleavable amide derivatives that may be formed at a carboxy group or an amino group in a compound of the Formula I.

Accordingly, the present invention includes those compounds of the Formula I as defined hereinbefore when made available by organic synthesis and when made available within the human or animal body by way of cleavage of a pro-drug thereof. Accordingly, the present invention includes those compounds of the Formula I that are produced by organic synthetic means and also such compounds that are produced in the human or animal body by way of metabolism of a precursor compound, that is a compound of the Formula I may be a synthetically-produced compound or a metabolically-produced compound.

A suitable pharmaceutically-acceptable pro-drug of a compound of the Formula I is one that is based on reasonable medical judgement as being suitable for administration to the human or animal body without undesirable pharmacological activities and without undue toxicity.

Various forms of pro-drug have been described, for example in the following documents:— a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically-acceptable pro-drug of a compound of the Formula I that possesses a carboxy group is, for example, an in vivo cleavable ester thereof. An in vivo cleavable ester of a compound of the Formula I containing a carboxy group is, for example, a pharmaceutically-acceptable ester which is cleaved in the human or animal body to produce the parent acid. Suitable pharmaceutically-acceptable esters for carboxy include (1-6C)alkyl esters such as methyl, ethyl and tert-butyl, (1-6C)alkoxymethyl esters such as methoxymethyl esters, (1-6C)alkanoyloxymethyl esters such as pivaloyloxymethyl esters, 3-phthalidyl esters, (3-8C)cycloalkylcarbonyloxy-(1-6C)alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and (1-6C)alkoxycarbonyloxy-(1-6C)alkyl esters such as methoxycarbonyloxymethyl and 1-methoxycarbonyloxyethyl esters.

A suitable pharmaceutically-acceptable pro-drug of a compound of the Formula I that possesses a hydroxy group is, for example, an in vivo cleavable ester or ether thereof. An in vivo cleavable ester or ether of a compound of the Formula I containing a hydroxy group is, for example, a pharmaceutically-acceptable ester or ether which is cleaved in the human or animal body to produce the parent hydroxy compound. Suitable pharmaceutically-acceptable ester forming groups for a hydroxy group include inorganic esters such as phosphate esters (including phosphoramidic cyclic esters). Further suitable pharmaceutically-acceptable ester forming groups for a hydroxy group include (1-10C)alkanoyl groups such as acetyl, benzoyl, phenylacetyl and substituted benzoyl and phenylacetyl groups, (1-10C)alkoxycarbonyl groups such as ethoxycarbonyl, N,N-[di-(1-4C)alkyl]carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(1-4C)alkylpiperazin-1-ylmethyl. Suitable pharmaceutically-acceptable ether forming groups for a hydroxy group include α-acyloxyalkyl groups such as acetoxymethyl and pivaloyloxymethyl groups.

A suitable pharmaceutically-acceptable pro-drug of a compound of the Formula I that possesses a carboxy group is, for example, an in vivo cleavable amide thereof, for example an amide formed with an amine such as ammonia, a (1-4C)alkylamine such as methylamine, a di-(1-4C)alkylamine such as dimethylamine, N-ethyl-N-methylamine or diethylamine, a (1-4C)alkoxy-(2-4C)alkylamine such as 2-methoxyethylamine, a phenyl-(1-4C)alkylamine such as benzylamine and amino acids such as glycine or an ester thereof.

A suitable pharmaceutically-acceptable pro-drug of a compound of the Formula I that possesses an amino group is, for example, an in vivo cleavable amide derivative thereof. Suitable pharmaceutically-acceptable amides from an amino group include, for example an amide formed with (1-10C)alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(1-4C)alkylpiperazin-1-ylmethyl.

The in vivo effects of a compound of the Formula I may be exerted in part by one or more metabolites that are formed within the human or animal body after administration of a compound of the Formula I. As stated hereinbefore, the in vivo effects of a compound of the Formula I may also be exerted by way of metabolism of a precursor compound (a pro-drug).

According to a further aspect of the invention there is provided a pyrimidine derivative of the Formula I as defined hereinbefore wherein:—

$Q^a$ is a heteroaryl group that optionally bears 1, 2, 3 or 4 substituents, which may be the same or different, selected from halogeno, trifluoromethyl, cyano, isocyano, nitro, hydroxy, mercapto, amino, formyl, carboxy, carbamoyl, ureido, (1-8C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N'-(1-6C)alkylureido, N',N'-di-[(1-6C)alkyl]ureido, N-(1-6C)alkylureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$Q^2$-$X^2$— wherein $X^2$ is a direct bond or is selected from O, S, SO, $SO_2$, $N(R^5)$, CO, $CH(OR^5)$, $CON(R^5)$, $N(R^5)CO$, $N(R^5)CON(R^5)$, $SO_2N(R^5)$, $N(R^5)SO_2$, $OC(R^5)_2$, $SC(R^5)_2$ and $N(R^5)C(R^5)_2$, wherein $R^5$ is hydrogen or (1-8C)alkyl, and $Q^2$ is aryl, aryl-(1-6C)alkyl, (3-8C)cycloalkyl, (3-8C)cycloalkyl-(1-6C)alkyl, (3-8C)cycloalkenyl, (3-8C)cycloalkenyl-(1-6C)alkyl, heteroaryl, heteroaryl-(1-6C)alkyl, heterocyclyl or heterocyclyl-(1-6C)alkyl, or $Q^a$ bears a (1-3C)alkylenedioxy substituent, and wherein any CH, $CH_2$ or $CH_3$ group within a substituent on $Q^a$ optionally bears on each said CH, $CH_2$ or $CH_3$ group one or more halogeno or (1-8C)alkyl substituents and/or a substituent selected from hydroxy, mercapto, amino, cyano, carboxy, carbamoyl, ureido, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylureido, N'-(1-6C)alkylureido, N',N'-di-[(1-6C)alkyl]ureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—$X^3$-$Q^3$ wherein $X^3$ is a direct bond or is selected from O, S, SO, $SO_2$, $N(R^6)$, CO, $CH(OR^6)$, $CON(R^6)$, $N(R^6)CO$, $N(R^6)CON(R^6)$, $SO_2N(R^6)$, $N(R^6)SO_2$, $C(R^6)_2O$, $C(R^6)_2S$ and $C(R^6)_2N(R^6)$, wherein $R^6$ is hydrogen or (1-8C)alkyl, and $Q^3$ is aryl, aryl-(1-6C)alkyl, (3-8C)cycloalkyl, (3-8C)cycloalkyl-(1-6C)alkyl, (3-8C)cycloalkenyl, (3-8C)cycloalkenyl-(1-6C)alkyl, heteroaryl, heteroaryl-(1-6C)alkyl, heterocyclyl or heterocyclyl-(1-6C)alkyl, and wherein any aryl, (3-8C)cycloalkyl, (3-8C)cycloalkenyl, heteroaryl or heterocyclyl group within a substituent on $Q^a$ optionally bears 1, 2 or 3 substituents, which may be the same or different, selected from halogeno, trifluoromethyl, cyano, nitro, hydroxy, amino, carboxy, carbamoyl, ureido, (1-8C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (2-6C)alkanoylamino, N-(1-6C)alkyl-(2-6C)alkanoylamino, N-(1-6C)alkylureido, N'-(1-6C)alkylureido, N',N'-di-[(1-6C)alkyl]ureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—$X^4$—$R^7$ wherein $X^4$ is a direct bond or is selected from O and $N(R^8)$, wherein $R^8$ is hydrogen or (1-8C)alkyl, and $R^7$ is halogeno-(1-6C)alkyl, hydroxy-(1-6C)alkyl, mercapto-(1-6C)alkyl, (1-6C)alkoxy-(1-6C)alkyl, (1-6C)alkylthio-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, (1-6C)alkoxycarbonylamino-(1-6C)alkyl, N-(1-6C)alkylureido-(1-6C)alkyl, N'-(1-6C)alkylureido-(1-6C)alkyl, N',N'-di-[(1-6C)alkyl]ureido-(1-6C)alkyl, N,N'-di-[(1-6C)alkyl]ureido-(1-6C)alkyl or N,N',N'-tri-[(1-6C)alkyl]ureido-(1-6C)alkyl, or from a group of the formula:

—$X^5$-$Q^4$ wherein $X^5$ is a direct bond or is selected from O, CO and $N(R^9)$, wherein $R^9$ is hydrogen or (1-8C)alkyl, and $Q^4$ is aryl, aryl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, hydroxy, (1-8C)alkyl and (1-6C)alkoxy, and wherein any heterocyclyl group within a substituent on $Q^a$ optionally bears 1 or 2 oxo or thioxo substituents, and wherein adjacent carbon atoms in any (2-6C)alkylene chain within a substituent on $Q^a$ are optionally separated by the insertion into the chain of a group selected from O, S, SO, $SO_2$, $N(R^{10})$, CO, $CH(OR^{10})$, $CON(R^{10})$, $N(R^{10})CO$, $N(R^{10})CON(R^{10})$, $SO_2N(R^{11})$, $N(R^{10})SO_2$, CH=CH and C≡C wherein $R^{10}$ is hydrogen or (1-8C)alkyl;

$G^1$ is N or $C(R^1)$ wherein $R^1$ is hydrogen or (1-8C)alkyl, and $G^2$ is N or $C(R^2)$ wherein $R^2$ is hydrogen or (1-8C)alkyl, provided that one of $G^1$ and $G^2$ is N, and if $G^1$ is N then $G^2$ is $C(R^2)$, or if $G^2$ is N then $G^1$ is $C(R^1)$;

q is 0, 1, 2, 3 or 4;

each $R^3$ group, which may be the same or different, is (1-8C)alkyl or a group of the formula:

—$X^6$—$R^{11}$ wherein $X^6$ is a direct bond or is selected from O and $N(R^{12})$, wherein $R^{12}$ is hydrogen or (1-8C)alkyl, and $R^{11}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl or (2-6C)alkanoylamino-(1-6C)alkyl;

r is 0, 1 or 2;

each $R^4$ group, which may be the same or different, is selected from halogeno, trifluoromethyl, cyano, nitro, hydroxy, mercapto, amino, carboxy, carbamoyl, ureido, (1-8C)alkyl, (2-8C)alkenyl, (2-8C)alkynyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N'-(1-6C)alkylureido, N',N'-di-[(1-6C)alkyl]ureido, N-(1-6C)alkylureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino;

$X^1$ is selected from $N(R^{13})CO$, $CON(R^{13})$, $N(R^{13})CON(R^{13})$, $N(R^{13})COC(R^{13})_2O$, $N(R^{13})COC(R^{13})_2S$, $N(R^{13})COC(R^{13})_2N(R^{13})$ and $N(R^{13})COC(R^{13})_2N(R^{13})CO$, wherein $R^{13}$ is hydrogen or (1-8C)alkyl; and $Q^b$ is (1-8C)alkyl, (2-8C)alkenyl, (2-8C)alkynyl, halogeno-(1-6C)alkyl, hydroxy-(1-6C)alkyl, mercapto-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (1-6C)alkylthio-(1-6C)alkyl, (1-6C)alkylsulphinyl-(1-6C)alkyl, (1-6C)alkylsulphonyl-(1-6C)alkyl, (2-6C)alkanoylamino-(1-6C)alkyl, N-(1-6C)alkyl-(2-6C)alkanoylamino-(1-6C)alkyl, (1-6C)alkoxycarbonylamino-(1-6C)alkyl, N-(1-6C)alkylureido-(1-6C)alkyl, N'-(1-6C)alkylureido-(1-6C)alkyl, N',N'-di-[(1-6C)alkyl]ureido-(1-6C)alkyl, N,N'-di-[(1-6C)alkyl]ureido-(1-6C)alkyl, N,N',N'-tri-[(1-6C)alkyl]ureido-(1-6C)alkyl, (1-6C)alkanesulphonylamino-(1-6C)alkyl or N-(1-6C)alkyl-(1-6C)alkanesulphonylamino-(1-6C)alkyl, or $Q^b$ is aryl, aryl-(1-6C)alkyl, (3-8C)cycloalkyl, (3-8C)cycloalkyl-(1-6C)alkyl, (3-8C)cycloalkenyl, (3-8C)cycloalkenyl-(1-6C)alkyl, heteroaryl, heteroaryl-(1-6C)alkyl, heterocyclyl or heterocyclyl-(1-6C)alkyl, and wherein any CH, $CH_2$ or $CH_3$ group within the $Q^b$ group optionally bears on each said CH, $CH_2$ or $CH_3$ group one or more halogeno or (1-8C)alkyl substituents and/or a substituent selected from hydroxy, mercapto, amino, cyano, carboxy, carbamoyl, ureido, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N'-(1-6C)alkylureido, N',N'-di-[(1-6C)alkyl]ureido, N-(1-6C)alkylureido, N,N'-di-[(1-6C)alkyl]ureido, N,N',N'-tri-[(1-6C)alkyl]ureido, N-(1-6C)alkylsulphamoyl, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, and wherein any aryl, (3-8C)cycloalkyl, (3-8C)cycloalkenyl, heteroaryl or heterocyclyl group within the $Q^b$ group optionally bears 1, 2 or 3 substituents, which may be the same or different, selected from halogeno, trifluoromethyl, cyano, nitro, hydroxy, amino, carboxy, carbamoyl, ureido, (1-8C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (2-6C)alkanoylamino, N-(1-6C)alkyl-(2-6C)alkanoylamino, N'-(1-6C)alkylureido, N',N'-di-[(1-6C)alkyl]ureido, N-(1-6C)alkylureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—$X^7$—$R^{14}$ wherein $X^7$ is a direct bond or is selected from O and $N(R^{15})$, wherein $R^{15}$ is hydrogen or (1-8C)alkyl, and $R^{14}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl, and wherein any heterocyclyl group within the $Q^b$ group optionally bears 1 or 2 oxo or thioxo substituents, and wherein adjacent carbon atoms in any (2-6C)alkylene chain within the $Q^b$ group are optionally separated by the insertion into the chain of a group selected from O, S, SO, $SO_2$, $N(R^{16})$, $N(R^{16})CO$, $CON(R^{16})$, $N(R^{16})CON(R^{16})$, CO, $CH(OR^{16})$, $N(R^{16})SO_2$, $SO_2N(R^{16})$, CH=CH and C≡C wherein $R^{16}$ is hydrogen or (1-8C)alkyl;

or a pharmaceutically-acceptable salt, solvate or pro-drug thereof.

Particular novel compounds of the invention include, for example, pyrimidine derivatives of the Formula I, or pharmaceutically-acceptable salts, solvates or pro-drugs thereof, wherein, unless otherwise stated, each of $Q^a$, $G^1$, $G^2$, q, $R^3$, r, $R^4$, $X^1$ and $Q^b$ has any of the meanings defined hereinbefore or in paragraphs (a) to (ww) hereinafter:—

(a) $Q^a$ is a heteroaryl group that optionally bears 1, 2 or 3 substituents and $Q^a$ is an aromatic 5- or 6-membered monocyclic ring or a 9- or 10-membered bicyclic ring with up to five ring heteroatoms selected from oxygen, nitrogen and sulphur;

(b) $Q^a$ is a heteroaryl group that optionally bears 1, 2 or 3 substituents and $Q^a$ is an aromatic 5- or 6-membered monocyclic ring with up to five ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, pyridyl, pyridazinyl, pyrimidinyl or pyrazinyl;

(c) $Q^a$ is a heteroaryl group that optionally bears 1, 2 or 3 substituents and $Q^a$ is an aromatic 9- or 10-membered bicyclic ring with up to five ring heteroatoms selected from oxygen, nitrogen and sulphur, for example benzofuranyl, indolyl, benzothienyl, benzoxazolyl, benzimidazolyl, benzothiazolyl, indazolyl, quinolyl, isoquinolyl, quinazolinyl or quinoxalinyl;

(d) $Q^a$ is a heteroaryl group that optionally bears 1 or 2 substituents and $Q^a$ is furyl, pyrrolyl, thienyl, oxazolyl, isoxazolyl, imidazolyl, pyrazolyl, thiazolyl, isothiazolyl, oxadiazolyl, thiadiazolyl, triazolyl, pyridyl, pyridazinyl, pyrimidinyl or pyrazinyl;

(e) $Q^a$ is a heteroaryl group that optionally bears 1 or 2 substituents, which may be the same or different, selected from halogeno, trifluoromethyl, cyano, hydroxy, mercapto, amino, carboxy, carbamoyl, ureido, (1-8C)alkyl, (2-8C)alkenyl, (2-8C)alkynyl, (1-6C)alkoxy, (2-6C)alkenyloxy, (2-6C)alkynyloxy, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$Q^2$-$X^2$— wherein $X^2$ is a direct bond or is selected from O, S, $N(R^5)$, CO, wherein $R^5$ is hydrogen or (1-8C)alkyl, and $Q^2$ is aryl, aryl-(1-6C)alkyl, (3-8C)cycloalkyl, (3-8C)cycloalkyl-(1-6C)alkyl, heteroaryl, heteroaryl-(1-6C)alkyl, heterocyclyl or heterocyclyl-(1-6C)alkyl, or $(R^1)_p$ is (1-3C)alkylenedioxy, and wherein any CH, $CH_2$ or $CH_3$ group within a $Q^a$ substituent optionally bears on each said CH, $CH_2$ or $CH_3$ group one or more halogeno or (1-8C)alkyl substituents and/or a substituent selected from hydroxy, mercapto, amino, cyano, carboxy, carbamoyl, ureido, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, and wherein any aryl, (3-8C)cycloalkyl, heteroaryl or heterocyclyl group within a substituent on $Q^a$ optionally bears 1, 2 or 3 substituents, which may be the same or different, selected from halogeno, trifluoromethyl, cyano, hydroxy, amino, (1-8C)alkyl, (2-8C)alkenyl, (2-8C)alkynyl, (1-6C)alkoxy, (1-6C)alkylamino and di-[(1-6C)alkyl]amino, and wherein any heterocyclyl group within a substituent on $Q^a$ optionally bears 1 or 2 oxo or thioxo substituents;

(f) $Q^a$ is a heteroaryl group that optionally bears 1 or 2 substituents, which may be the same or different, selected from halogeno, trifluoromethyl, cyano, hydroxy, amino, carboxy, carbamoyl, ureido, (1-8C)alkyl, (2-8C)alkenyl, (2-8C)alkynyl, (1-6C)alkoxy, (1-6C)alkylamino, di-[(1-6C)alkyl]amino, (1-6C)alkoxycarbonyl, (2-6C)alkanoylamino and N-(1-6C)alkyl-(2-6C)alkanoylamino, and wherein any CH, $CH_2$ or $CH_3$ group within a $Q^a$ substituent optionally bears on each said CH, $CH_2$ or $CH_3$ group 1, 2 or 3 halogeno or (1-8C)alkyl substituents and/or a substituent selected from hydroxy, amino, cyano, carboxy, carbamoyl, ureido, (1-6C)alkoxy, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoylamino and N-(1-6C)alkyl-(2-6C)alkanoylamino;

(g) $Q^a$ is a heteroaryl group that optionally bears 1 or 2 substituents, which may be the same or different, selected from fluoro, chloro, trifluoromethyl, cyano, hydroxy, amino, carboxy, carbamoyl, ureido, methyl, ethyl, propyl, vinyl, allyl, ethynyl, 2-propynyl, methoxy, ethoxy, propoxy, isopropoxy, methylamino, ethylamino, propylamino, dimethylamino, diethylamino, methoxycarbonyl, ethoxycarbonyl, acetamido, propionamido, N-methylacetamido, N-methylpropionamido, hydroxymethyl, 1-hydroxyethyl, 1-hydroxy-1-methylethyl, 2-hydroxyethyl, 2-hydroxy-1-methylethyl, 2-hydroxypropyl, 1,1-dimethyl-2-hydroxyethyl, 2-hydroxy-2-methylpropyl, aminomethyl, 1-aminoethyl, 1-amino-1-methylethyl, 2-aminoethyl, 2-amino-1-methylethyl, 2-aminopropyl, 2-amino-1,1-dimethylethyl, 2-amino-2-methylpropyl, methylaminomethyl, 1-methylaminoethyl, 1-methylamino-1-methylethyl, 2-methylaminoethyl, 2-methylamino-1-methylethyl, 2-methylaminopropyl, 2-methylamino-1,1-dimethylethyl, 2-methylamino-2-methylpropyl, acetamidomethyl, 1-acetamidoethyl, 1-acetamido-1-methylethyl, 2-acetamidoethyl, 2-acetamido-1-methylethyl, 2-acetamidopropyl, 2-acetamido-1,1-dimethylethyl and 2-acetamido-2-methylpropyl;

(h) $Q^a$ is a heteroaryl group that optionally bears 1 or 2 substituents comprising a first substituent selected from hydroxy, amino, carboxy, carbamoyl, methoxy, ethoxy, methylamino, ethylamino, dimethylamino, diethylamino, methoxycarbonyl, ethoxycarbonyl, acetamido, propionamido, N-methylacetamido, N-methylpropionamido, hydroxymethyl, 1-hydroxyethyl, 1-hydroxy-1-methylethyl, aminomethyl, 1-aminoethyl, 1-amino-1-methylethyl, methylaminomethyl, 1-methylaminoethyl, 1-methylamino-1-methylethyl, acetamidomethyl, 1-acetamidoethyl and 1-acetamido-1-methylethyl, and a second substituent selected from fluoro, chloro, trifluoromethyl, cyano, hydroxy, methyl, ethyl, propyl, vinyl, allyl, ethynyl, 2-propynyl, methoxy, ethoxy, propoxy and isopropoxy;

(i) $Q^a$ is a heteroaryl group that bears 1 or 2 substituents comprising a first substituent selected from hydroxy, carbamoyl, methoxy, ethoxy, acetamido, propionamido, N-methylacetamido, N-methylpropionamido, hydroxymethyl, 1-hydroxyethyl and 1-hydroxy-1-methylethyl, and an optional second substituent selected from fluoro, chloro, trifluoromethyl, cyano, hydroxy, methyl, ethyl, methoxy and ethoxy;

(j) $Q^a$ is a heteroaryl group that bears a single substituent selected from hydroxy, carbamoyl, acetamido, hydroxymethyl, 1-hydroxyethyl and 1-hydroxy-1-methylethyl;

(k) $Q^a$ is a heteroaryl group that bears a single substituent selected from hydroxy and hydroxymethyl;

(l) $G^1$ is $C(R^1)$ wherein $R^1$ is hydrogen or (1-8C)alkyl, and $G^2$ is N;

(m) $G^1$ is CH and $G^2$ is N;

(n) $G^1$ is N and $G^2$ is $C(R^2)$ wherein $R^2$ is hydrogen or (1-8C)alkyl;

(o) $G^1$ is N and $G^2$ is CH;

(p) q is 0;

(q) q is 1, 2 or 3 and each $R^3$ group, which may be the same or different, is methyl, ethyl or propyl;

(r) q is 1 and the $R^3$ group is methyl;

(s) r is 0;

(t) r is 1 or 2 and each $R^4$ group, which may be the same or different, is selected from halogeno, trifluoromethyl, cyano, hydroxy, amino, (1-8C)alkyl, (2-8C)alkenyl, (2-8C)alkynyl, (1-6C)alkoxy, (1-6C)alkylamino, di-[(1-6C)alkyl]amino, (2-6C)alkanoylamino and N-(1-6C)alkyl-(2-6C)alkanoylamino;

(u) r is 0 or r is 1 or 2 and each $R^4$ group, which may be the same or different, is selected from fluoro, chloro, trifluoromethyl, cyano, hydroxy, amino, methyl, methoxy, methylamino and dimethylamino;

(v) r is 0 or r is 1 and the $R^4$ group is selected from fluoro, chloro, trifluoromethyl, hydroxy, amino, methyl, methoxy, methylamino and dimethylamino;

(w) r is 0 or r is 1 and the $R^4$ group is selected from fluoro, chloro and methyl;

(x) the $X^1$-$Q^b$ group is located at the 3- or 4-position;

(y) the $X^1$-$Q^b$ group is located at the 3-position;

(z) the $X^1$-$Q^b$ group is located at the 4-position;

(aa) $X^1$ is selected from $N(R^{13})CO$, $CON(R^{13})$, $N(R^{13})CON(R^{13})$, $N(R^{13})COC(R^{13})_2O$, $N(R^{13})COC(R^{13})_2N(R^{13})$ and $N(R^{13})COC(R^{13})_2N(R^{13})CO$, wherein $R^{13}$ is hydrogen or (1-8C)alkyl;

(bb) $X^1$ is selected from CO, $N(R^{13})CO$, $CON(R^{13})$, $N(R^{13})CON(R^{13})$, $N(R^{13})COC(R^{13})_2O$, $N(R^{13})COC(R^{13})_2N(R^{13})$ and $N(R^{13})COC(R^{13})_2N(R^{13})CO$, wherein $R^{13}$ is hydrogen or (1-8C)alkyl;

(cc) $X^1$ is selected from NHCO, NHCONH, $NHCOCH_2O$, $NHCOCH_2NH$ and $NHCOCH_2NHCO$;

(dd) $X^1$ is selected from CO, NHCO, N(Me)CO, CONH, CON(Me), NHCONH, NHCOCH$_2$O, NHCOCH$_2$NH and NHCOCH$_2$NHCO;

(ee) $X^1$ is selected from NHCO, NHCONH and NHCOCH$_2$O;

(ff) $X^1$ is selected from NHCO, N(Me)CO, CONH, CON(Me), NHCONH and NHCOCH$_2$O;

(gg) $X^1$ is NHCO;

(hh) $X^1$ is NHCO or N(Me)CO;

(ii) $X^1$ is CONH;

(jj) $X^1$ is CONH or CON(Me);

(kk) $X^1$ is CO;

(ll) $Q^b$ is (1-8C)alkyl, (2-8C)alkenyl, (2-8C)alkynyl, halogeno-(1-6C)alkyl, hydroxy-(1-6C)alkyl, mercapto-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (1-6C)alkylthio-(1-6C)alkyl, (1-6C)alkylsulphinyl-(1-6C)alkyl, (1-6C)alkylsulphonyl-(1-6C)alkyl or (2-6C)alkanoylamino-(1-6C)alkyl, or $Q^b$ is aryl, aryl-(1-6C)alkyl, (3-8C)cycloalkyl, (3-8C)cycloalkyl-(1-6C)alkyl, heteroaryl, heteroaryl-(1-6C)alkyl, heterocyclyl or heterocyclyl-(1-6C)alkyl, and wherein any CH, CH$_2$ or CH$_3$ group within the $Q^b$ group optionally bears on each said CH, CH$_2$ or CH$_3$ group one or more halogeno or (1-8C)alkyl substituents and/or a substituent selected from hydroxy, amino, cyano, carboxy, carbamoyl, ureido, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoylamino and N-(1-6C)alkyl-(2-6C)alkanoylamino, and wherein any aryl, (3-8C)cycloalkyl, heteroaryl or heterocyclyl group within the $Q^b$ group optionally bears 1, 2 or 3 substituents, which may be the same or different, selected from halogeno, trifluoromethyl, cyano, hydroxy, amino, (1-8C)alkyl, (2-8C)alkenyl, (2-8C)alkynyl, (1-6C)alkoxy, (1-6C)alkylamino and di-[(1-6C)alkyl]amino, or from a group of the formula:

—$X^7$—$R^{14}$ wherein $X^7$ is a direct bond or is selected from O and N($R^{15}$), wherein $R^{15}$ is hydrogen or (1-8C)alkyl, and $R^{14}$ is hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl, and wherein any heterocyclyl group within the $Q^b$ group optionally bears 1 or 2 oxo or thioxo substituents;

(mm) $Q^b$ is (1-8C)alkyl, (2-8C)alkenyl, (2-8C)alkynyl, halogeno-(1-6C)alkyl, hydroxy-(1-6C)alkyl, mercapto-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (1-6C)alkylthio-(1-6C)alkyl, (1-6C)alkylsulphinyl-(1-6C)alkyl, (1-6C)alkylsulphonyl-(1-6C)alkyl or (2-6C)alkanoylamino-(1-6C)alkyl, or $Q^b$ is aryl, aryl-(1-6C)alkyl, (3-8C)cycloalkyl, (3-8C)cycloalkyl-(1-6C)alkyl, heteroaryl, heteroaryl-(1-6C)alkyl, heterocyclyl or heterocyclyl-(1-6C)alkyl, and wherein any CH, CH$_2$ or CH$_3$ group within the $Q^b$ group optionally bears on each said CH, CH$_2$ or CH$_3$ group one or more halogeno or (1-8C)alkyl substituents and/or a substituent selected from hydroxy, amino, cyano, carboxy, carbamoyl, ureido, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoylamino and N-(1-6C)alkyl-(2-6C)alkanoylamino, and wherein any aryl, (3-8C)cycloalkyl, heteroaryl or heterocyclyl group within the $Q^b$ group optionally bears 1, 2 or 3 substituents, which may be the same or different, selected from halogeno, trifluoromethyl, cyano, hydroxy, amino, carbamoyl, (1-8C)alkyl, (2-8C)alkenyl, (2-8C)alkynyl, (1-6C)alkoxy, (1-6C)alkylamino and di-[(1-6C)alkyl]amino, or from a group of the formula:

—$X^7$—$R^{14}$ wherein $X^7$ is a direct bond or is selected from O and N($R^{15}$), wherein $R^{15}$ is hydrogen or (1-8C)alkyl, and $R^{14}$ is hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl, or from a group of the formula:

—$X^8$-$Q^5$ wherein $X^8$ is a direct bond or is selected from O, CO and N($R^{17}$), wherein $R^{17}$ is hydrogen or (1-8C)alkyl, and $Q^5$ is heterocyclyl or heterocyclyl-(1-6C)alkyl which optionally bears 1 or 2 substituents, which may be the same or different, selected from halogeno, hydroxy, (1-8C)alkyl and (1-6C)alkoxy, and wherein any heterocyclyl group within the $Q^b$ group optionally bears 1 or 2 oxo or thioxo substituents;

(nn) $Q^b$ is (1-8C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (1-6C)alkylthio-(1-6C)alkyl or (2-6C)alkanoylamino-(1-6C)alkyl, or $Q^b$ is aryl, aryl-(1-6C)alkyl, (3-8C)cycloalkyl, (3-8C)cycloalkyl-(1-6C)alkyl, heteroaryl, heteroaryl-(1-6C)alkyl, heterocyclyl or heterocyclyl-(1-6C)alkyl, and wherein any CH, CH$_2$ or CH$_3$ group within the $Q^b$ group optionally bears on each said CH, CH$_2$ or CH$_3$ group 1, 2 or 3 halogeno or (1-8C)alkyl substituents and/or a substituent selected from hydroxy, amino, cyano, carboxy, carbamoyl, ureido, (1-6C)alkoxy, (1-6C)alkylthio, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoylamino and N-(1-6C)alkyl-(2-6C)alkanoylamino, and wherein any aryl, (3-8C)cycloalkyl, heteroaryl or heterocyclyl group within the $Q^b$ group optionally bears 1 or 2 substituents, which may be the same or different, selected from halogeno, trifluoromethyl, cyano, hydroxy, amino, (1-8C)alkyl, (1-6C)alkoxy, (1-6C)alkylamino and di-[(1-6C)alkyl]amino, or from a group of the formula:

—$X^7$—$R^{14}$ wherein $X^7$ is a direct bond and $R^{14}$ is hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl;

(oo) $Q^b$ is (1-8C)alkyl, hydroxy-(1-6C)alkyl, (1-6C)alkoxy-(1-6C)alkyl, amino-(1-6C)alkyl, (1-6C)alkylamino-(1-6C)alkyl, di-[(1-6C)alkyl]amino-(1-6C)alkyl or (1-6C)alkylthio-(1-6C)alkyl, or $Q^b$ is aryl, aryl-(1-6C)alkyl, (3-8C)cycloalkyl, (3-8C)cycloalkyl-(1-6C)alkyl, heteroaryl, heteroaryl-(1-6C)alkyl, heterocyclyl or heterocyclyl-(1-6C)alkyl, and wherein any aryl, (3-8C)cycloalkyl, heteroaryl or heterocyclyl group within the $Q^b$ group optionally bears 1 or 2 substituents, which may be the same or different, selected from halogeno, trifluoromethyl, hydroxy, amino, (1-8C) alkyl, (1-6C)alkoxy, (1-6C)alkylamino, di-[(1-6C)alkyl] amino, hydroxy-(1-6C)alkyl, amino-(1-6C)alkyl, (1-6C) alkylamino-(1-6C)alkyl and di-[(1-6C)alkyl]amino-(1-6C) alkyl;

(pp) $Q^b$ is (1-8C)alkyl, hydroxy-(1-6C)alkyl, (1-6C)alkoxy-(1-6C)alkyl, cyano-(1-6C)alkyl, amino-(1-6C)alkyl, (1-6C) alkylamino-(1-6C)alkyl, di-[(1-6C)alkyl]amino-(1-6C) alkyl, (1-6C)alkylsulphonyl-(1-6C)alkyl or (2-6C) alkanoylamino-(1-6C)alkyl, or $Q^b$ is aryl, aryl-(1-6C)alkyl, (3-8C)cycloalkyl, (3-8C)cycloalkyl-(1-6C)alkyl, heteroaryl, heteroaryl-(1-6C)alkyl, heterocyclyl or heterocyclyl-(1-6C) alkyl, and wherein any CH, $CH_2$ or $CH_3$ group within the $Q^b$ group optionally bears on each said CH, $CH_2$ or $CH_3$ group a substituent selected from hydroxy, amino, cyano, carbamoyl, (1-6C)alkoxy, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoylamino and N-(1-6C)alkyl-(2-6C) alkanoylamino, and wherein any aryl, (3-8C)cycloalkyl, heteroaryl or heterocyclyl group within the $Q^b$ group optionally bears 1 or 2 substituents, which may be the same or different, selected from halogeno, trifluoromethyl, hydroxy, amino, carbamoyl, (1-8C)alkyl, (1-6C)alkoxy, (1-6C)alkylamino, di-[(1-6C) alkyl]amino, hydroxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl and heterocyclyl-(1-6C)alkyl;

(qq) $Q^b$ is methyl, ethyl, propyl, butyl, pentyl, aminomethyl, 2-aminoethyl, 3-aminopropyl, 4-aminobutyl, 5-aminopentyl, methylaminomethyl, 2-methylaminoethyl, 3-methylaminopropyl, 4-methylaminobutyl, 5-methylaminopentyl, ethylaminomethyl, 2-ethylaminoethyl, 3-ethylaminopropyl, 4-ethylaminobutyl, 5-ethylaminopentyl, dimethylaminomethyl, 2-dimethylaminoethyl, 3-dimethylaminopropyl, 4-dimethylaminobutyl, 5-dimethylaminopentyl, diethylaminomethyl, 2-diethylaminoethyl, 3-diethylaminopropyl, 4-diethylaminobutyl or 5-diethylaminopentyl, or $Q^b$ is phenyl, benzyl, 2-phenylethyl, cyclopropyl, cyclohexyl, cycloheptyl, cyclopentylmethyl, cyclohexylmethyl, cycloheptylmethyl, furyl, thienyl, oxazolyl, imidazolyl, thiazolyl, oxadiazolyl, thiadiazolyl, pyridyl, pyrimidinyl, furylmethyl, thienylmethyl, oxazolylmethyl, imidazolylmethyl, thiazolylmethyl, oxadiazolylmethyl, thiadiazolylmethyl, pyridylmethyl, pyrimidinylmethyl, tetrahydrofuranyl, tetrahydropyranyl, tetrahydrothiopyranyl, pyrrolinyl, pyrrolidinyl, imidazolidinyl, pyrazolidinyl, morpholinyl, tetrahydro-1,4-thiazinyl, piperidinyl, homopiperidinyl, piperazinyl, homopiperazinyl, 2-azabicyclo[2.2.1]heptyl, indolinyl, isoindolinyl, dihydropyridinyl, tetrahydrofuranylmethyl, tetrahydropyranylmethyl, tetrahydrothiopyranylmethyl, pyrrolinylmethyl, pyrrolidinylmethyl, imidazolidinylmethyl, pyrazolidinylmethyl, morpholinylmethyl, 2-(morpholinyl)ethyl, tetrahydro-1,4-thiazinylmethyl, 2-(tetrahydro-1,4-thiazinyl)ethyl, piperidinylmethyl, 2-(piperidinyl)ethyl, homopiperidinylmethyl, piperazinylmethyl, 2-(piperazinyl)ethyl, homopiperazinylmethyl or 2-azabicyclo[2.2.1]heptylmethyl, and wherein any aryl, (3-8C)cycloalkyl, heteroaryl or heterocyclyl group within the $Q^b$ group optionally bears 1 or 2 substituents, which may be the same or different, selected from fluoro, chloro, trifluoromethyl, hydroxy, amino, methyl, ethyl, methoxy, ethoxy, methylamino, dimethylamino, hydroxymethyl, 2-hydroxyethyl, aminomethyl, 2-aminoethyl, methylaminomethyl, 2-methylaminoethyl, dimethylaminomethyl and 2-dimethylaminoethyl;

(rr) $Q^b$ is methyl, ethyl, propyl, isopropyl, butyl, pentyl, allyl, 2-hydroxyethyl, 3-hydroxypropyl, 2-methoxyethyl, 3-methoxypropyl, 2-ethoxyethyl, 3-ethoxypropyl, cyanomethyl, 2-cyanoethyl, 3-cyanopropyl, 1-cyano-1-methylethyl, 4-cyanobutyl, 5-cyanopentyl, aminomethyl, 2-aminoethyl, 3-aminopropyl, 4-aminobutyl, 5-aminopentyl, methylaminomethyl, 2-methylaminoethyl, 3-methylaminopropyl, 4-methylaminobutyl, 5-methylaminopentyl, ethylaminomethyl, 2-ethylaminoethyl, 3-ethylaminopropyl, 4-ethylaminobutyl, 5-ethylaminopentyl, 1-isopropyl-1-methylaminomethyl, dimethylaminomethyl, 2-dimethylaminoethyl, 3-dimethylaminopropyl, 4-dimethylaminobutyl, 5-dimethylaminopentyl, diethylaminomethyl, 2-diethylaminoethyl, 3-diethylaminopropyl, 4-diethylaminobutyl, 5-diethylaminopentyl, 2-methylsulphonylethyl, 3-methylsulphonylpropyl, acetamidomethyl or 1-acetamidoethyl, or $Q^b$ is phenyl, benzyl, 2-phenylethyl, cyclopropyl, cyclobutyl, cyclopentyl, cyclohexyl, cycloheptyl, cyclopropylmethyl, cyclobutylmethyl, cyclopentylmethyl, cyclohexylmethyl, cycloheptylmethyl, furyl, thienyl, oxazolyl, isoxazolyl, imidazolyl, pyrazolyl, thiazolyl, triazolyl, oxadiazolyl, thiadiazolyl, tetrazolyl, pyridyl, pyrazinyl, pyridazinyl, pyrimidinyl, furylmethyl, 2-furylethyl, thienylmethyl, 2-thienylethyl, oxazolylmethyl, 2-oxazolylethyl, isoxazolylmethyl, 2-isoxazolylethyl, imidazolylmethyl, 2-imidazolylethyl, pyrazolylmethyl, 2-pyrazolylethyl, thiazolylmethyl, 2-thiazolylethyl, triazolylmethyl, 2-triazolylethyl, oxadiazolylmethyl, 2-oxadiazolylethyl, thiadiazolylmethyl, 2-thiadiazolylethyl, tetrazolylmethyl, 2-tetrazolylethyl, pyridylmethyl, 2-pyridylethyl, pyrazinylmethyl, 2-pyrazinylethyl, pyridazinylmethyl, 2-pyridazinylethyl, pyrimidinylmethyl, 2-pyrimidinylethyl, tetrahydrofuranyl, tetrahydropyranyl, tetrahydrothiopyranyl, azetidinyl, pyrrolinyl, pyrrolidinyl, imidazolidinyl, pyrazolidinyl, morpholinyl, tetrahydro-1,4-thiazinyl, piperidinyl, homopiperidinyl, piperazinyl, homopiperazinyl, 2-azabicyclo[2.2.1]heptyl, indolinyl, isoindolinyl, dihydropyridinyl, tetrahydrofuranylmethyl, tetrahydropyranylmethyl, tetrahydrothiopyranylmethyl, 1,3-dioxolanylmethyl, 1,4-dioxanylmethyl, pyrrolinylmethyl, pyrrolidinylmethyl, imidazolidinylmethyl, pyrazolidinylmethyl, morpholinylmethyl, 2-(morpholinyl)ethyl, tetrahydro-1,4-thiazinylmethyl, 2-(tetrahydro-1,4-thiazinyl)ethyl, piperidinylmethyl, 2-(piperidinyl)ethyl, homopiperidinylmethyl, piperazinylmethyl, 2-(piperazinyl)ethyl, homopiperazinylmethyl or 2-azabicyclo[2.2.1]heptylmethyl, and wherein any CH, $CH_2$ or $CH_3$ group within the $Q^b$ group optionally bears on each said CH, $CH_2$ or $CH_3$ group a substituent selected from hydroxy, amino, cyano, carbamoyl, methoxy, ethoxy, methylsulphonyl, methylamino, ethylamino, dimethylamino, diethylamino, methoxycarbonyl, ethoxycarbonyl, N-methylcarbamoyl, N-ethylcarbamoyl, N-isopropylcarbamoyl, N,N-dimethylcarbamoyl, N,N-diethylcarbamoyl, acetyl, propionyl, butyryl, pivaloyl, acetamido, propionamido and N-methylacetamido, and wherein any aryl, (3-8C)cycloalkyl, heteroaryl or heterocyclyl group within the $Q^b$ group optionally bears 1 or 2 substituents, which may be the same or different, selected from fluoro, chloro, trifluoromethyl, hydroxy, amino, carbamoyl, methyl, ethyl, methoxy, ethoxy, methylamino, dimethylamino, hydroxymethyl, 2-hydroxyethyl, methoxymethyl, 2-methoxyethyl, cyanomethyl, 2-cyanoethyl, aminomethyl, 2-aminoethyl, methylaminomethyl, 2-methylaminoethyl, dimethylaminomethyl, 2-dimethylaminoethyl, pyrrolidinylmethyl, morpholinylmethyl, piperidinylmethyl, homopiperidinylmethyl, piperazinylmethyl and homopiperazinylmethyl;

(ss) $Q^b$ is methyl, ethyl, propyl, butyl, pentyl, aminomethyl, 2-aminoethyl, 3-aminopropyl, 4-aminobutyl, 5-aminopentyl, methylaminomethyl, 2-methylaminoethyl, 3-methylaminopropyl, 4-methylaminobutyl, 5-methylaminopentyl, dimethylaminomethyl, 2-dimethylaminoethyl, 3-dimethylaminopropyl, 4-dimethylaminobutyl or 5-dimethylaminopentyl, or $Q^b$ is phenyl, benzyl, 2-phenylethyl, cyclopentyl, cyclohexyl, cyclopentylmethyl, cyclohexylmethyl, thienyl, imidazolyl, thiazolyl, thiadiazolyl, thienylmethyl, imidazolylmethyl, thiazolylmethyl, thiadiazolylmethyl, tetrahydrofuranyl, tetrahydropyranyl, tetrahydrothiopyranyl, pyrrolinyl, pyrrolidinyl, morpholinyl, tetrahydro-1,4-thiazinyl, piperidinyl, homopiperidinyl, piperazinyl, homopiperazinyl, indolinyl, isoindolinyl, pyrrolidinylmethyl, morpholinylmethyl, 2-(morpholinyl)ethyl, piperidinylmethyl, 2-(piperidinyl)ethyl, homopiperidinylmethyl, piperazinylmethyl, 2-(piperazinyl)ethyl, homopiperazinylmethyl or 2-azabicyclo[2.2.1]heptylmethyl, and wherein any aryl, (3-8C)cycloalkyl, heteroaryl or heterocyclyl group within the $Q^b$ group optionally bears a substituent selected from fluoro, chloro, trifluoromethyl, hydroxy, amino, methyl, methoxy, methylamino and dimethylamino and any such aryl, (3-8C)cycloalkyl, heteroaryl or heterocyclyl group within the $Q^b$ group optionally bears a further substituent selected from aminomethyl, methylaminomethyl and dimethylaminomethyl;

(tt) $Q^b$ is methyl, ethyl, propyl, isopropyl, butyl, pentyl, allyl, 2-methoxyethyl, 3-methoxypropyl, 2-ethoxyethyl, 3-ethoxypropyl, cyanomethyl, 2-cyanoethyl, 3-cyanopropyl, 1-cyano-1-methylethyl, 4-cyanobutyl, 5-cyanopentyl, aminomethyl, 2-aminoethyl, 3-aminopropyl, 4-aminobutyl, 5-aminopentyl, methylaminomethyl, 2-methylaminoethyl, 3-methylaminopropyl, 4-methylaminobutyl, 5-methylaminopentyl, ethylaminomethyl, 2-ethylaminoethyl, 3-ethylaminopropyl, 4-ethylaminobutyl, 5-ethylaminopentyl, dimethylaminomethyl, 2-dimethylaminoethyl, 3-dimethylaminopropyl, 4-dimethylaminobutyl, 5-dimethylaminopentyl, diethylaminomethyl, 2-diethylaminoethyl, 3-diethylaminopropyl, 4-diethylaminobutyl, 5-diethylaminopentyl, 2-methylsulphonylethyl or acetamidomethyl, or $Q^b$ is phenyl, benzyl, 2-phenylethyl, cyclopropyl, cyclobutyl, cyclopentyl, cyclohexyl, cyclopropylmethyl, cyclobutylmethyl, cyclopentylmethyl, cyclohexylmethyl, furyl, thienyl, oxazolyl, isoxazolyl, imidazolyl, pyrazolyl, thiazolyl, triazolyl, oxadiazolyl, thiadiazolyl, tetrazolyl, pyridyl, pyrazinyl, pyridazinyl, pyrimidinyl, furylmethyl, thienylmethyl, oxazolylmethyl, isoxazolylmethyl, imidazolylmethyl, 2-imidazolylethyl, pyrazolylmethyl, thiazolylmethyl, triazolylmethyl, oxadiazolylmethyl, thiadiazolylmethyl, tetrazolylmethyl, pyridylmethyl, 2-pyridylethyl, pyrazinylmethyl, 2-pyrazinylethyl, pyridazinylmethyl, 2-pyridazinylethyl, pyrimidinylmethyl, 2-pyrimidinylethyl, tetrahydrofuranyl, tetrahydropyranyl, tetrahydrothiopyranyl, azetidinyl, pyrrolinyl, pyrrolidinyl, morpholinyl, tetrahydro-1,4-thiazinyl, piperidinyl, homopiperidinyl, piperazinyl, homopiperazinyl, indolinyl, isoindolinyl, tetrahydrofuranylmethyl, tetrahydropyranylmethyl, 1,3-dioxolanylmethyl, 1,4-dioxanylmethyl, pyrrolidinylmethyl, morpholinylmethyl, 2-(morpholinyl)ethyl, piperidinylmethyl, 2-(piperidinyl)ethyl, homopiperidinylmethyl, piperazinylmethyl, 2-(piperazinyl)ethyl or homopiperazinylmethyl, and wherein any CH, CH$_2$ or CH$_3$ group within the $Q^b$ group optionally bears on each said CH, CH$_2$ or CH$_3$ group a substituent selected from hydroxy, amino, cyano, carbamoyl, methoxy, ethoxy, methylsulphonyl, methylamino, dimethylamino, methoxycarbonyl, ethoxycarbonyl, N-methylcarbamoyl, N-ethylcarbamoyl, N-isopropylcarbamoyl, N,N-dimethylcarbamoyl, acetyl, propionyl, pivaloyl, acetamido and N-methylacetamido, and wherein any aryl, (3-8C)cycloalkyl, heteroaryl or heterocyclyl group within the $Q^b$ group optionally bears 1 or 2 substituents, which may be the same or different, selected from fluoro, chloro, trifluoromethyl, hydroxy, amino, carbamoyl, methyl, methoxy, methylamino and dimethylamino and any such aryl, (3-8C)cycloalkyl, heteroaryl or heterocyclyl group within the $Q^b$ group optionally bears a substituent selected from hydroxymethyl, methoxymethyl, cyanomethyl, aminomethyl, methylaminomethyl, dimethylaminomethyl, pyrrolidinylmethyl, morpholinylmethyl, piperidinylmethyl and piperazinylmethyl;

(uu) the $X^1$-$Q^b$ group is an amino carboxamido group;

(vv) the $X^1$-$Q^b$ group is a naturally-occurring α-amino carboxamido group; and (ww) the $X^1$-$Q^b$ group is selected from glycylamino, sarcosylamino, (N,N-dimethylglycyl)amino, glycylglycylamino, L-alanylamino, 2-methylalanylamino, (N-methylalanyl)amino, (2S)-2-aminobutanoylamino, L-valylamino, (N-methyl-L-valyl)amino, 2-aminopent-4-ynoylamino, 2-aminopentanoylamino, L-isoleucylamino, L-leucylamino, 2-methyl-L-leucylamino, (N-methyl-L-leucyl)amino, serylamino, (O-methyl-L-seryl)amino, (N-methyl-L-seryl)amino, (O-methyl-L-homoseryl)amino, L-threonylamino, (S-methyl-L-cysteinyl)amino, (S-methyl-L-homocysteinyl)amino, L-methionylamino, (N-methyl-L-lysyl)amino, (N-methyl-L-ornithyl)amino, D-asparaginylamino, D-glutaminylamino, L-tyrosylamino, propylamino and histidylamino.

A particular compound of the invention is a pyrimidine derivative of the Formula I wherein:—

$Q^a$ is furyl, pyrrolyl, thienyl, oxazolyl, isoxazolyl, imidazolyl, pyrazolyl, thiazolyl, isothiazolyl, oxadiazolyl, thiadiazolyl, triazolyl, pyridyl, pyridazinyl, pyrimidinyl, pyrazinyl, benzimidazolyl, benzoxazolyl or benzothiazolyl, and $Q^a$ bears 1 or 2 substituents comprising a first substituent selected from hydroxy, carbamoyl, methoxy, ethoxy, acetamido, propionamido, N-methylacetamido, N-methylpropionamido, hydroxymethyl, 1-hydroxyethyl and 1-hydroxy-1-methylethyl, and an optional second substituent selected from fluoro, chloro, trifluoromethyl, cyano, hydroxy, methyl, ethyl, methoxy and ethoxy;

$G^1$ is CH and $G^2$ is N, or $G^1$ is N and $G^2$ is CH;

q is 0 or q is 1 and the $R^3$ group is methyl;

r is 0 or r is 1 and the $R^4$ group is selected from fluoro, chloro, trifluoromethyl, hydroxy, amino, methyl, methoxy, methylamino and dimethylamino;

the $X^1$-$Q^b$ group is located at the 3- or 4-position;

$X^1$ is selected from CO, NHCO, N(Me)CO, CONH, CON(Me), NHCONH, NHCOCH$_2$O, NHCOCH$_2$NH and NHCOCH$_2$NHCO; and $Q^b$ is methyl, ethyl, propyl, isopropyl, butyl, pentyl, allyl, 2-methoxyethyl, 3-methoxypropyl, 2-ethoxyethyl, 3-ethoxypropyl, cyanomethyl, 2-cyanoethyl, 3-cyanopropyl, 1-cyano-1-methylethyl, 4-cyanobutyl, 5-cyanopentyl, aminomethyl, 2-aminoethyl, 3-aminopropyl, 4-aminobutyl, 5-aminopentyl, methylaminomethyl, 2-methylaminoethyl, 3-methylaminopropyl, 4-methylaminobutyl, 5-methylaminopentyl, ethylaminomethyl, 2-ethylaminoethyl, 3-ethylaminopropyl, 4-ethylaminobutyl, 5-ethylaminopentyl, dimethylaminomethyl, 2-dimethylaminoethyl, 3-dimethylaminopropyl, 4-dimethylaminobutyl, 5-dimethylaminopentyl, diethylaminomethyl, 2-diethylaminoethyl, 3-diethylaminopropyl, 4-diethylaminobutyl, 5-diethylaminopentyl, 2-methylsulphonylethyl or acetamidomethyl, or $Q^b$ is phenyl, benzyl, 2-phenylethyl, cyclopropyl, cyclobutyl, cyclopentyl, cyclohexyl, cyclopropylmethyl, cyclobutylmethyl, cyclopentylmethyl, cyclohexylmethyl, furyl, thienyl, oxazolyl, isoxazolyl, imidazolyl, pyrazolyl, thiazolyl, triazolyl, oxadiazolyl, thiadiazolyl, tetrazolyl, pyridyl, pyrazinyl, pyridazinyl, pyrimidinyl, furylmethyl, thienylmethyl, oxazolylmethyl, isoxazolylmethyl, imidazolylmethyl, 2-imidazolylethyl, pyrazolylmethyl, thiazolylmethyl, triazolylmethyl, oxadiazolylmethyl, thiadiazolylmethyl, tetrazolylmethyl, pyridylmethyl, 2-pyridylethyl, pyrazinylmethyl, 2-pyrazinylethyl, pyridazinylmethyl, 2-pyridazinylethyl, pyrimidinylmethyl, 2-pyrimidinylethyl, tetrahydrofuranyl, tetrahydropyranyl, tetrahydrothiopyranyl, azetidinyl, pyrrolinyl, pyrrolidinyl, morpholinyl, tetrahydro-1,4-thiazinyl, piperidinyl, homopiperidinyl, piperazinyl, homopiperazinyl, indolinyl, isoindolinyl, tetrahydrofuranylmethyl, tetrahydropyranylmethyl, 1,3-dioxolanylmethyl, 1,4-dioxanylmethyl, pyrrolidinylmethyl, morpholinylmethyl, 2-(morpholinyl)ethyl, piperidinylmethyl, 2-(piperidinyl)ethyl, homopiperidinylmethyl, piperazinylmethyl, 2-(piperazinyl)ethyl or homopiperazinylmethyl, and wherein any CH, $CH_2$ or $CH_3$ group within the $Q^b$ group optionally bears on each said CH, $CH_2$ or $CH_3$ group a substituent selected from hydroxy, amino, cyano, carbamoyl, methoxy, ethoxy, methylsulphonyl, methylamino, dimethylamino, methoxycarbonyl, ethoxycarbonyl, N-methylcarbamoyl, N-ethylcarbamoyl, N-isopropylcarbamoyl, N,N-dimethylcarbamoyl, acetyl, propionyl, pivaloyl, acetamido and N-methylacetamido, and wherein any aryl, (3-8C)cycloalkyl, heteroaryl or heterocyclyl group within the $Q^b$ group optionally bears 1 or 2 substituents, which may be the same or different, selected from fluoro, chloro, trifluoromethyl, hydroxy, amino, carbamoyl, methyl, methoxy, methylamino and dimethylamino and any such aryl, (3-8C)cycloalkyl, heteroaryl or heterocyclyl group within the $Q^b$ group optionally bears a substituent selected from hydroxymethyl, methoxymethyl, cyanomethyl, aminomethyl, methylaminomethyl, dimethylaminomethyl, pyrrolidinylmethyl, morpholinylmethyl, piperidinylmethyl and piperazinylmethyl;

or a pharmaceutically-acceptable salt, solvate or pro-drug thereof.

A further particular compound of the invention is a pyrimidine derivative of the Formula I wherein:—

$Q^a$ is furyl, pyrrolyl, thienyl, oxazolyl, isoxazolyl, imidazolyl, pyrazolyl, thiazolyl, isothiazolyl, oxadiazolyl, thiadiazolyl, triazolyl, pyridyl, pyridazinyl, pyrimidinyl or pyrazinyl, and $Q^a$ bears 1 or 2 substituents comprising a first substituent selected from hydroxy, carbamoyl, methoxy, ethoxy, acetamido, propionamido, N-methylacetamido, N-methylpropionamido, hydroxymethyl, 1-hydroxyethyl and 1-hydroxy-1-methylethyl, and an optional second substituent selected from fluoro, chloro, trifluoromethyl, cyano, hydroxy, methyl, ethyl, methoxy and ethoxy;

$G^1$ is CH and $G^2$ is N, or $G^1$ is N and $G^2$ is CH;

q is 0 or q is 1 and the $R^3$ group is methyl;

r is 0 or r is 1 and the $R^4$ group is selected from fluoro, chloro, trifluoromethyl, hydroxy, amino, methyl, methoxy, methylamino and dimethylamino;

the $X^1$-$Q^b$ group is located at the 3-position;

$X^1$ is selected from NHCO, NHCONH, $NHCOCH_2O$, $NHCOCH_2NH$ and $NHCOCH_2NHCO$; and $Q^b$ is methyl, ethyl, propyl, butyl, pentyl, aminomethyl, 2-aminoethyl, 2-amino-2-methylpropyl, 3-aminopropyl, 4-aminobutyl, 5-aminopentyl, methylaminomethyl, 2-methylaminoethyl, 3-methylaminopropyl, 4-methylaminobutyl, 5-methylaminopentyl, dimethylaminomethyl, 2-dimethylaminoethyl, 3-dimethylaminopropyl, 4-dimethylaminobutyl or 5-dimethylaminopentyl, or $Q^b$ is phenyl, benzyl, 2-phenylethyl, cyclopentyl, cyclohexyl, cyclopentylmethyl, cyclohexylmethyl, thienyl, imidazolyl, thiazolyl, thiadiazolyl, thienylmethyl, imidazolylmethyl, thiazolylmethyl, thiadiazolylmethyl, tetrahydrofuranyl, tetrahydropyranyl, tetrahydrothiopyranyl, pyrrolinyl, pyrrolidinyl, morpholinyl, tetrahydro-1,4-thiazinyl, piperidinyl, homopiperidinyl, piperazinyl, homopiperazinyl, indolinyl, isoindolinyl, pyrrolidinylmethyl, morpholinylmethyl, 2-(morpholinyl)ethyl, piperidinylmethyl, 2-(piperidinyl)ethyl, piperidinyloxymethyl, homopiperidinylmethyl, piperazinylmethyl, 2-(piperazinyl)ethyl, homopiperazinylmethyl or 2-azabicyclo[2.2.1]heptylmethyl, and wherein any aryl, (3-8C)cycloalkyl, heteroaryl or heterocyclyl group within the $Q^b$ group optionally bears a substituent selected from fluoro, chloro, trifluoromethyl, hydroxy, amino, methyl, methoxy, methylamino and dimethylamine and any such aryl, (3-8C)cycloalkyl, heteroaryl or heterocyclyl group within the $Q^b$ group optionally bears a further substituent selected from aminomethyl, methylaminomethyl and dimethylaminomethyl;

or a pharmaceutically-acceptable salt, solvate or pro-drug thereof.

A further particular compound of the invention is a pyrimidine derivative of the Formula I wherein:—

$Q^a$ is furyl, thienyl, oxazolyl, isoxazolyl, imidazolyl, pyrazolyl, thiazolyl, isothiazolyl, pyridyl, pyridazinyl, pyrimidinyl or pyrazinyl, and $Q^a$ bears 1 or 2 substituents comprising a first substituent selected from hydroxy, carbamoyl, methoxy, acetamido, N-methylacetamido, hydroxymethyl, 1-hydroxyethyl and 1-hydroxy-1-methylethyl, and an optional second substituent selected from fluoro, chloro, trifluoromethyl, cyano, hydroxy, methyl and methoxy;

$G^1$ is CH and $G^2$ is N, or $G^1$ is N and $G^2$ is CH;

q is 0;

r is 0;

the $X^1$-$Q^b$ group is located at the 3-position;

$X^1$ is NHCO; and $Q^b$ is methyl, aminomethyl, 2-aminopropyl, 2-amino-2-methylpropyl, 3-aminopropyl, methylaminomethyl or dimethylaminomethyl, or $Q^b$ is phenyl, benzyl, 2-phenylethyl, cyclopentyl, cyclohexyl, cyclohexylmethyl, thiazol-5-yl, thien-3-ylmethyl, imidazol-1-ylmethyl, 1,2,4-thiadiazol-3-ylmethyl, tetrahydropyran-4-yl, tetrahydrothiopyran-4-yl, 3-pyrrolin-2-yl, pyrrolidin-2-yl, pyrrolidin-3-yl, morpholin-2-yl, piperidin-2-yl, piperidin-3-yl, piperidin-4-yl, piperazin-1-yl, isoindoline-1-yl, pyrrolidin-2-ylmethyl, piperidin-4-ylmethyl, 2-(piperidin-4-yl)ethyl, piperidin-4-yloxymethyl, piperazin-1-ylmethyl or 2-azabicyclo[2.2.1]hept-2-ylmethyl, and wherein any aryl, (3-8C)cycloalkyl, heteroaryl or heterocyclyl group within the $Q^b$ group optionally bears a substituent selected from amino, methyl, methylamino and aminomethyl;

or a pharmaceutically-acceptable salt, solvate or pro-drug thereof.

A further particular compound of the invention is a pyrimidine derivative of the Formula I wherein:—

Q$^a$ is furyl, thienyl, oxazolyl, isoxazolyl, imidazolyl, pyrazolyl, thiazolyl, isothiazolyl, pyridyl, pyridazinyl, pyrimidinyl, pyrazinyl, benzimidazolyl, benzoxazolyl or benzothiazolyl, and Q$^a$ bears 1 or 2 substituents comprising a first substituent selected from hydroxy, carbamoyl, methoxy, acetamido, N-methylacetamido, hydroxymethyl, 1-hydroxyethyl and 1-hydroxy-1-methylethyl, and an optional second substituent selected from fluoro, chloro, trifluoromethyl, cyano, hydroxy, methyl and methoxy;

G$^1$ is CH and G$^2$ is N, or G$^1$ is N and G$^2$ is CH;

q is 0;

r is 0 or r is 1 and the R$^4$ group is selected from fluoro, chloro and methyl;

the X$^1$-Q$^b$ group is located at the 3- or 4-position;

X$^1$ is NHCO, N(Me)CO, CONH or CON(Me); and

Q$^b$ is methyl, ethyl, propyl, isopropyl, 2-ethoxyethyl, 3-ethoxypropyl, cyanomethyl, 2-cyanoethyl, aminomethyl, 2-aminoethyl, methylaminomethyl, 2-methylaminoethyl, ethylaminomethyl, 2-ethylaminoethyl, dimethylaminomethyl, 2-dimethylaminoethyl, 4-dimethylaminobutyl, 2-methylsulphonylethyl or acetamidomethyl, or Q$^b$ is phenyl, benzyl, cyclopropyl, cyclobutyl, cyclopentyl, cyclohexyl, cyclopropylmethyl, cyclobutylmethyl, cyclopentylmethyl, cyclohexylmethyl, oxazol-5-yl, isoxazol-3-yl, isoxazol-4-yl, imidazol-2-yl, imidazol-4-yl, pyrazol-3-yl, thiazol-5-yl, 1,2,3-triazol-5-yl, tetrazol-5-yl, pyridin-2-yl, pyridin-3-yl, pyridin-4-yl, pyrazin-2-yl, pyridazin-4-yl, pyrimidin-2-yl, pyrimidin-4-yl, thien-3-ylmethyl, oxazol-4-ylmethyl, isoxazol-3-ylmethyl, isoxazol-4-ylmethyl, imidazol-1-ylmethyl, imidazol-2-ylmethyl, 2-imidazol-1-ylethyl, 2-imidazol-2-ylethyl, 2-imidazol-4-ylethyl, pyrazol-1-ylmethyl, pyrazol-3-ylmethyl, 1,2,3-triazol-1-ylmethyl, 1,2,3-triazol-4-ylmethyl, 1,2,4-oxadiazol-3-ylmethyl, 1,2,3-thiadiazol-3-ylmethyl, tetrazol-1-ylmethyl, tetrazol-5-ylmethyl, pyridin-2-ylmethyl, pyridin-3-ylmethyl, pyridin-4-ylmethyl, 2-pyridin-2-ylethyl, 2-pyridin-3-ylethyl, 2-pyridin-4-ylethyl, pyrazin-2-ylmethyl, 2-pyrazin-2-ylethyl, pyridazin-4-ylmethyl, 2-pyridazin-4-ylethyl, pyrimidin-2-ylmethyl, pyrimidin-4-ylmethyl, 2-pyrimidin-2-ylethyl, 2-pyrimidin-4-ylethyl, tetrahydrofuran-2-yl, tetrahydropyran-4-yl, tetrahydrothiopyran-4-yl, azetidin-2-yl, 3-pyrrolin-2-yl, pyrrolidin-1-yl, pyrrolidin-2-yl, pyrrolidin-3-yl, morpholino, morpholin-2-yl, piperidino, piperidin-2-yl, piperidin-3-yl, piperidin-4-yl, piperazin-1-yl, isoindoline-1-yl, tetrahydrofuran-2-ylmethyl, tetrahydropyran-4-ylmethyl, 1,3-dioxolan-2-ylmethyl, 1,4-dioxan-2-ylmethyl, pyrrolidin-2-ylmethyl, piperidin-2-ylmethyl, piperidin-3-ylmethyl, piperidin-4-ylmethyl, 2-(piperidin-4-yl)ethyl, piperidin-4-yloxymethyl, piperazin-1-ylmethyl or 2-(piperazin-1-yl)ethyl, and wherein any CH, CH$_2$ or CH$_3$ group within the Q$^b$ group optionally bears on each said CH, CH$_2$ or CH$_3$ group a substituent selected from hydroxy, carbamoyl, methoxycarbonyl, ethoxycarbonyl, N-methylcarbamoyl, N-ethylcarbamoyl, N-isopropylcarbamoyl, N,N-dimethylcarbamoyl, acetyl, propionyl, pivaloyl, acetamido and N-methylacetamido, and wherein any aryl, (3-8C)cycloalkyl, heteroaryl or heterocyclyl group within the Q$^b$ group optionally bears 1 or 2 substituents, which may be the same or different, selected from fluoro, chloro, hydroxy, amino, carbamoyl, methyl, methylamino, dimethylamino, hydroxymethyl, methoxymethyl, cyanomethyl, aminomethyl, methylaminomethyl, dimethylaminomethyl and 1-methylpiperidin-4-ylmethyl;

or a pharmaceutically-acceptable salt, solvate or pro-drug thereof.

A further particular compound of the invention is a pyrimidine derivative of the Formula I wherein:—

Q$^a$ is 2-furyl, 3-furyl, 2-thienyl, 3-thienyl, 3-pyridyl, 4-pyridyl, 4-pyrimidinyl or 5-pyrimidinyl, and Q$^a$ bears 1 or 2 substituents comprising a first substituent selected from hydroxy, methoxy, hydroxymethyl and 1-hydroxyethyl, and an optional second substituent selected from fluoro, chloro, trifluoromethyl, cyano, hydroxy, methyl and methoxy;

G$^1$ is CH and G$^2$ is N, or G$^1$ is N and G$^2$ is CH;

q is 0;

r is 0;

the X$^1$-Q$^b$ group is located at the 3-position;

X$^1$ is NHCO; and

Q$^b$ is methyl, aminomethyl, 2-aminocyclopent-1-yl, 4-aminocyclohex-1-yl, 3-aminocyclohex-1-ylmethyl, 4-aminomethylcyclohex-1-yl, imidazol-1-ylmethyl, 5-amino-1,2,4-thiadiazol-3-ylmethyl, pyrrolidin-3-yl, N-methylpyrrolidin-2-yl, piperidin-2-yl, piperidin-3-yl, piperidin-4-yl, N-methylpiperidin-4-yl, pyrrolidin-2-ylmethyl, piperidin-4-ylmethyl, 2-(piperidin-4-yl)ethyl, piperidin-4-yloxymethyl or 4-methylpiperazin-1-ylmethyl, or a pharmaceutically-acceptable salt, solvate or pro-drug thereof.

A further particular compound of the invention is a pyrimidine derivative of the Formula I wherein:—

Q$^a$ is 2-furyl, 3-furyl, 2-thienyl, 3-thienyl, 3-pyridyl, 4-pyridyl, 4-pyrimidinyl, 5-pyrimidinyl, 4-benzimidazolyl or 5-benzimidazolyl, and Q$^a$ bears 1 or 2 substituents comprising a first substituent selected from hydroxy, methoxy, hydroxymethyl and 1-hydroxyethyl, and an optional second substituent selected from fluoro, chloro, trifluoromethyl, cyano, hydroxy, methyl and methoxy;

G$^1$ is CH and G$^2$ is N, or G$^1$ is N and G$^2$ is CH;

q is 0;

r is 0;

the X$^1$-Q$^b$ group is located at the 3- or 4-position;

X$^1$ is NHCO or N(Me)CO; and

Q$^b$ is aminomethyl, methylaminomethyl, ethylaminomethyl, dimethylaminomethyl, acetamidomethyl, 3-aminomethylphenyl, 4-aminomethylphenyl, 5-methylisoxazol-3-yl, 1-methylpyrazol-3-yl, 1H-1,2,3-triazol-5-yl, pyridin-4-yl, pyrazin-2-yl, 2-imidazol-1-ylethyl, 2-imidazol-2-ylethyl, 3,5-dimethyl-1H-pyrazol-1-ylmethyl, 1H-tetrazol-5-ylmethyl, 2-pyridin-3-ylethyl, 2-pyridazin-4-ylethyl, azetidin-2-yl, 3-pyrrolin-2-yl, N-methylpyrrolidin-2-yl, 4-hydroxypyrrolidin-2-yl, piperidin-3-yl, piperidin-4-yl, N-methylpiperidin-4-yl, piperazin-1-yl, piperidin-3-ylmethyl, piperidin-4-yloxymethyl or piperazin-1-ylmethyl;

or a pharmaceutically-acceptable salt, solvate or pro-drug thereof.

A further particular compound of the invention is a pyrimidine derivative of the Formula I wherein:—

Q$^a$ is 2-furyl, 3-furyl, 2-thienyl, 3-thienyl, 3-pyridyl, 4-pyridyl, 4-pyrimidinyl, 5-pyrimidinyl, 4-benzimidazolyl or 5-benzimidazolyl, and Q$^a$ bears 1 or 2 substituents comprising a first substituent selected from hydroxy, methoxy, hydroxymethyl and 1-hydroxyethyl, and an optional second substituent selected from fluoro, chloro, trifluoromethyl, cyano, hydroxy, methyl and methoxy;

G$^1$ is CH and G$^2$ is N, or G$^1$ is N and G$^2$ is CH;

q is 0;

r is 0;

the X$^1$-Q$^b$ group is located at the 3- or 4-position;

X$^1$ is CONH or CON(Me); and

Q$^b$ is methyl, ethyl, propyl, isopropyl, 2-ethoxyethyl, 3-ethoxypropyl, cyanomethyl, 1-cyano-1-methylethyl, 2-cyanoethyl, 5-cyanopentyl, 2-aminoethyl, 2-methylaminoethyl, 2-dimethylaminoethyl, 4-dimethylaminobutyl, 2-methylsulphonylethyl, 3-methoxycarbonylpropyl, carbamoylmethyl, 1-carbamoylethyl, 2-carbamoylethyl, N-methylcarbamoylmethyl, N-isopropylcarbamoylmethyl, N,N-dimethylcarbamoylmethyl, pivaloylmethyl, 4-aminomethylphenyl, 4-aminobenzyl, cyclopropyl, cyclobutyl, cyclopentyl, cyclopropylmethyl, cyclobutylmethyl, cyclopentylmethyl, thien-3-ylmethyl, oxazol-4-ylmethyl, 5-methylisoxazol-3-ylmethyl, isoxazol-4-ylmethyl, 1H-imidazol-1-ylmethyl, 1H-imidazol-2-ylmethyl, 2-(1H-imidazol-1-yl)ethyl, 2-(1H-imidazol-2-yl)ethyl, 2-(1H-imidazol-4-yl)ethyl, pyridin-2-ylmethyl, pyridin-3-ylmethyl, pyridin-4-ylmethyl, 2-pyridin-2-ylethyl, 2-pyridin-3-ylethyl, 2-pyridin-4-ylethyl, pyrazin-2-ylmethyl, 5-methylpyrazin-2-ylmethyl, tetrahydropyran-4-yl, tetrahydrothiopyran-4-yl, tetrahydrofuran-2-ylmethyl, tetrahydropyran-4-ylmethyl, 1,3-dioxolan-2-ylmethyl or 1,4-dioxan-2-ylmethyl;

or a pharmaceutically-acceptable salt, solvate or pro-drug thereof.

A further particular compound of the invention is a pyrimidine derivative of the Formula I wherein:—

$Q^a$ is 2-furyl, 3-furyl, 2-thienyl, 3-thienyl, 3-pyridyl, 4-pyridyl, 4-pyrimidinyl, 5-pyrimidinyl, 4-benzimidazolyl or 5-benzimidazolyl, and $Q^a$ bears 1 or 2 substituents comprising a first substituent selected from hydroxy, methoxy, hydroxymethyl and 1-hydroxyethyl, and an optional second substituent selected from fluoro, chloro, trifluoromethyl, cyano, hydroxy, methyl and methoxy;

$G^1$ is CH and $G^2$ is N, or $G^2$ is N and $G^2$ is CH;

q is 0;

r is 0;

the $X^1$-$Q^b$ group is located at the 3- or 4-position;

$X^1$ is CO; and $Q^b$ is 2-carbamoylpyrrolidin-1-yl, 2-methoxymethylpyrrolidin-1-yl, 4-aminopiperidin-1-yl, 4-aminomethylpiperidin-1-yl, 3-cyanomethylpiperidin-1-yl, 3-oxopiperazine-1-yl, 4-(1-methylpiperidin-4-ylmethyl)piperazin-1-yl or 5-oxo-1,4-diazepane-1-yl;

or a pharmaceutically-acceptable salt, solvate or pro-drug thereof.

A further particular compound of the invention is a pyrimidine derivative of the Formula I wherein:—

$Q^a$ is 5-hydroxymethylthien-2-yl, 2-methoxypyrimidin-5-yl or 2,4-dimethoxypyrimidin-5-yl;

$G^1$ is CH and $G^2$ is N;

q is 0;

r is 0;

the $X^1$-$Q^b$ group is located at the 3-position;

$X^1$ is NHCO; and $Q^b$ is methyl or piperidin-4-yl;

or a pharmaceutically-acceptable salt, solvate or pro-drug thereof.

A further particular compound of the invention is a pyrimidine derivative of the Formula I wherein:—

$Q^a$ is 5-hydroxymethylfuran-2-yl, 5-hydroxymethylthien-2-yl or benzimidazol-4-yl;

$G^1$ is CH and $G^2$ is N, or $G^1$ is N and $G^2$ is CH;

q is 0;

r is 0;

the $X^1$-$Q^b$ group is located at the 3-position;

$X^1$ is NHCO; and $Q^b$ is piperidin-3-yl or piperidin-4-yl;

or a pharmaceutically-acceptable salt, solvate or pro-drug thereof.

Particular compounds of the invention are, for example, the pyrimidine derivatives of the Formula I that are disclosed within Examples 1 to 6 that are set out hereinafter.

A particular compound of the invention is, for example, a pyrimidine derivative of the Formula I selected from:—

4-(5-hydroxymethylthien-2-yl)-6-morpholino-2-(3-piperidin-4-ylcarbonylaminophenyl)-pyrimidine, 2-(3-acetamidophenyl)-4-(2-methoxypyrimidin-5-yl)-6-morpholinopyrimidine, 2-(5-hydroxymethylfuran-2-yl)-6-morpholino-4-(3-piperidin-3-ylcarbonylaminophenyl)-pyrimidine or 4-(5-hydroxymethylfuran-2-yl)-6-morpholino-2-(3-piperidin-4-ylcarbonylaminophenyl)-pyrimidine;

or a pharmaceutically-acceptable salt, solvate or pro-drug thereof.

A pyrimidine derivative of the Formula I, or a pharmaceutically-acceptable salt, solvate or pro-drug thereof, may be prepared by any process known to be applicable to the preparation of chemically-related compounds. Such processes, when used to prepare a pyrimidine derivative of the Formula I are provided as a further feature of the invention and are illustrated by the following representative process variants in which, unless otherwise stated, $Q^a$, $G^1$, $G^2$, q, $R^3$, r, $R^4$, $X^1$ and $Q^b$ have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

(a) The reaction, conveniently in the presence of a suitable catalyst, of a pyrimidine of the Formula II

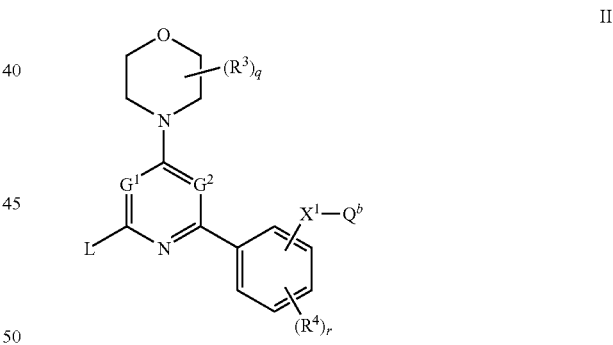

II wherein L is a displaceable group and $G^1$, $G^2$, q, $R^3$, r, $R^4$, $X^1$ and $Q^b$ have any of the meanings defined hereinbefore except that any functional group is protected if necessary, with an organoboron reagent of the Formula III

III wherein each of $L^1$ and $L^2$, which may be the same or different, is a suitable ligand and $Q^a$ has any of the meanings defined hereinbefore except that any functional group is protected if necessary, whereafter any protecting group that is present is removed by conventional means.

A suitable displaceable group L is, for example, a halogeno, alkoxy, aryloxy or sulphonyloxy group, for example a chloro, bromo, methoxy, phenoxy, pentafluorophenoxy, methanesulphonyloxy or toluene-4-sulphonyloxy group.

A suitable value for the ligands $L^1$ and $L^2$ which are present on the boron atom of the aryl-boron reagent include, for example, a hydroxy, (1-4C)alkoxy or (1-6C)alkyl ligand, for example a hydroxy, methoxy, ethoxy, propoxy, isopropoxy, butoxy, methyl, ethyl, propyl, isopropyl or butyl ligand. Alternatively the ligands $L^1$ and $L^2$ may be linked such that, together with the boron atom to which they are attached, they form a ring. For example, $L^1$ and $L^2$ together may define an oxy-(2-4C)alkylene-oxy group, for example an oxyethyleneoxy or oxytrimethyleneoxy group such that, together with the boron atom to which they are attached, they form a cyclic boronic acid ester group. Particularly suitable organoboron reagents include, for example, compounds wherein each of $L^1$ and $L^2$ is a hydroxy, a isopropoxy or an ethyl group.

A suitable catalyst for the reaction includes, for example, a metallic catalyst such as a palladium(0), palladium(II), nickel (0) or nickel(II) catalyst, for example tetrakis(triphenylphosphine)palladium(0), palladium(II) chloride, palladium(II) bromide, bis(triphenylphosphine)palladium(II) chloride, tetrakis(triphenylphosphine)nickel(0), nickel(II) chloride, nickel(II) bromide or bis(triphenylphosphine)nickel(II) chloride or [1,1'-bis(diphenylphosphino)ferrocene]dichloropalladium (II). In addition, a free radical initiator may conveniently be added, for example an azo compound such as azo(bisisobutyronitrile). Conveniently, the reaction may be carried out in the presence of a suitable base such as an alkali or alkaline earth metal carbonate or hydroxide, for example sodium bicarbonate, sodium carbonate, potassium bicarbonate, potassium carbonate, calcium carbonate, caesium carbonate, sodium hydroxide or potassium hydroxide, or, for example, an alkali metal alkoxide, for example sodium tert-butoxide, or, for example, an alkali metal amide, for example sodium hexamethyldisilazane, or, for example, an alkali metal hydride, for example sodium hydride.

The reaction is conveniently carried out in the presence of a suitable inert solvent or diluent, for example an ether such as tetrahydrofuran, 1,4-dioxan or 1,2-dimethoxyethane, an aromatic solvent such as benzene, toluene or xylene, or an alcohol such as methanol or ethanol, and the reaction is conveniently carried out at a temperature in the range, for example 10 to 250° C., preferably in the range 40 to 120° C.

Heteoraryl-boron reagents of the Formula III may be obtained by standard procedures of organic chemistry which are within the ordinary skill of an organic chemist, for example by the reaction of a heteroaryl-metal reagent where the metal is, for example, lithium or the magnesium halide portion of a Grignard reagent, with an organoboron compound of the formula L-B($L^1$)($L^2$) wherein L is a displaceable group as defined hereinbefore. Preferably the compound of the formula L-B($L^1$)($L^2$) is, for example, boric acid or a tri-(1-4C)alkyl borate such as tri-isopropyl borate.

In an alternative procedure, the heteroaryl-boron reagent of the Formula III may be replaced with an organometallic compound of the formula heteroaryl-M wherein M is a metal atom or a metallic group (that is a metal atom bearing suitable ligands). Suitable values for the metal atom include, for example, lithium and copper. Suitable values for the metallic group include, for example, groups which contain a tin, silicon, zirconium, aluminium, magnesium, mercury or zinc atom. Suitable ligands within such a metallic group include, for example, hydroxy groups, (1-6C)alkyl groups such as methyl, ethyl, propyl, isopropyl and butyl groups, halogeno groups such as chloro, bromo and iodo groups, and (1-6C) alkoxy groups such as methoxy, ethoxy, propoxy, isopropoxy and butoxy groups. A particular organometallic compound of the formula heteroaryl-M is, for example, an organotin compound such as a compound of the formula heteroaryl-SnBu$_3$, an organosilicon compound such as a compound of the formula heteroaryl-Si(Me)F$_2$, an organozirconium compound such as a compound of the formula heteroaryl-ZrCl$_3$, an organoaluminum compound such as a compound of the formula heteroaryl-AlEt$_2$, an organomagnesium compound such as a compound of the formula heteroaryl-MgBr, an organomercury compound such as a compound of the formula heteroaryl-HgBr, or an organozinc compound such as a compound of the formula heteroaryl-ZnBr.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1-20 carbon atoms). Examples of carboxy protecting groups include straight or branched chain (1-12C)alkyl groups (for example isopropyl, and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butyryloxymethyl and pivaloyloxymethyl); lower alkoxycarbonyloxy-lower alkyl groups (for example 1-methoxycarbonyloxyethyl and 1-ethoxycarbonyloxyethyl); aryl-lower alkyl groups (for example benzyl, 4-methoxybenzyl, 2-nitrobenzyl, 4-nitrobenzyl, benzhydryl and phthalidyl); tri(lower alkyl)silyl groups (for example trimethylsilyl and tert-butyldimethylsilyl); tri(lower alkyl)silyl-lower alkyl groups (for example trimethylsilylethyl); and (2-6C)alkenyl groups (for example allyl). Methods particularly appropriate for the removal of carboxyl protecting groups include for example acid-, base-, metal- or enzymically-catalysed cleavage.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower alkyl (for example benzyl) groups.

Examples of amino protecting groups include formyl, aryl-lower alkyl groups (for example benzyl and substituted benzyl, 4-methoxybenzyl, 2-nitrobenzyl and 2,4-dimethoxybenzyl, and triphenylmethyl); di-4-anisylmethyl and furylmethyl groups; lower alkoxycarbonyl (for example tert-butoxycarbonyl); lower alkenyloxycarbonyl (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); trialkylsilyl (for example trimethylsilyl and tert-butyldimethylsilyl); alkylidene (for example methylidene) and benzylidene and substituted benzylidene groups.

Methods appropriate for removal of hydroxy and amino protecting groups include, for example, acid-, base-, metal- or enzymically-catalysed hydrolysis for groups such as 2-nitrobenzyloxycarbonyl, hydrogenation for groups such as benzyl and photolytically for groups such as 2-nitrobenzyloxycarbonyl.

The reader is referred to Advanced Organic Chemistry, 4th Edition, by J. March, published by John Wiley & Sons 1992, for general guidance on reaction conditions and reagents and to Protective Groups in Organic Synthesis, $2^{nd}$ Edition, by T. Green et al., also published by John Wiley & Son, for general guidance on protecting groups.

In addition, a compound of the Formula I that bears functional group substitution, for example within the $Q^a$, $R^3$ or $Q^b$ groups, may be converted into a compound of the invention of the Formula I as defined hereinbefore by conventional organic chemistry.

For example, a compound of the Formula I wherein a $Q^a$ group carries a hydroxy-(1-8C)alkyl substituent may be obtained by the reduction by conventional means of the corresponding compound wherein the $Q^a$ group carries a OHC-(0-7C)alkyl substituent; for example, a compound of the Formula I wherein a $Q^a$ group carries a hydroxymethyl substituent may be obtained by the reduction by conventional means of the corresponding compound wherein the $Q^a$ group carries a formyl substituent. A suitable reducing agent is, for example, a hydride reducing agent, for example an alkali metal aluminium hydride such as lithium aluminium hydride or, preferably, an alkali metal borohydride such as sodium borohydride, sodium cyanoborohydride, sodium triethylborohydride, sodium trimethoxyborohydride and sodium triacetoxyborohydride. The reaction is conveniently performed in a suitable inert solvent or diluent, for example tetrahydrofuran and diethyl ether for the more powerful reducing agents such as lithium aluminium hydride, and, for example, methylene chloride or a protic solvent such as methanol and ethanol for the less powerful reducing agents such as sodium triacetoxyborohydride and sodium cyanoborohydride. The reaction is performed at a temperature in the range, for example, 10 to 80° C., conveniently at or near ambient temperature.

For example, a compound of the Formula I wherein a $Q^a$ group carries a halogeno substituent may be reacted with a metal cyanide to form a compound of the Formula I wherein the $Q^a$ group carries a cyano group. Conveniently, the reaction may be carried out in the presence of a suitable catalyst. A suitable metal cyanide is, for example, a heavy metal cyanide such as zinc cyanide. A suitable catalyst is, for example, an organometallic reagent, for example an organoiron compound such as diphenylphosphinoferrocene. The conversion reaction is conveniently carried out in the presence of a suitable inert diluent or carrier as defined hereinbefore and at a temperature in the range 10 to 150° C., preferably at or near 100° C.

For example, a compound of the Formula I wherein a $Q^a$ group carries a halogeno substituent may be reacted with a (2-8C)alkyne to form a compound of the Formula I wherein wherein the $Q^a$ group carries a (2-8C)alkynyl group such as an ethynyl group. The reaction may conveniently be carried out in the presence of a suitable base as defined hereinbefore and in the presence of a suitable catalyst. For this conversion, a suitable catalyst is, for example, an organometallic reagent, for example an organopalladium compound such as tetrakis (triphenylphosphine)palladium(0). The conversion reaction is conveniently carried out in the presence of a suitable inert diluent or carrier as defined hereinbefore and at a temperature in the range 10 to 150° C., preferably at or near 60° C.

For example, a compound of the Formula I wherein the $Q^a$ group is a phenyl ring that bears two amino substituents on adjacent ring positions may be converted into the corresponding compound wherein the $Q^a$ group is a benzimidazolyl group. Such a conversion may be carried out by conventional means, for example, by reaction with formic acid or an equivalent thereof such as ethyl formate or triethyl orthoformate. The reaction is conveniently performed in the presence of a suitable acidic catalyst such as 4-toluenesulphonic acid using a suitable inert solvent or diluent, for example an excess of triethyl orthoformate, and at a temperature in the range, for example, 20 to 140° C., conveniently at or near 80° C.

For example, a compound of the Formula I wherein a $Q^a$ group carries a (1-6C)alkylamino group, the alkylation, conveniently in the presence of a suitable base as defined hereinbefore, of a compound of the Formula I wherein the $Q^a$ group carries a primary or secondary amino group. A suitable alkylating agent is, for example, an alkyl halide, for example a (1-6C)alkyl chloride, bromide or iodide, conveniently in the presence of a suitable base as defined hereinbefore, in a suitable inert solvent or diluent as defined hereinbefore and at a temperature in the range, for example, 10 to 140° C., conveniently at or near ambient temperature. Conveniently, a reductive amination reaction may be employed. For example, for the production of those compounds of the Formula I wherein the $Q^a$ group carries a methylamino group, the corresponding compound wherein the $Q^a$ group carries an amino group may be reacted with formaldehyde in the presence of a suitable reducing agent. A suitable reducing agent is, for example, an alkali metal borohydride such as sodium borohydride or sodium cyanoborohydride. The reaction is conveniently performed in a suitable inert solvent or diluent, for example methylene chloride or a protic solvent such as methanol and ethanol. The reaction is performed at a temperature in the range, for example, 10 to 80° C., conveniently at or near ambient temperature.

Pyrimidine starting materials of the Formula II may be obtained by conventional procedures such as those disclosed in the Examples that are set out hereinafter. For example, for the production of those compounds of the Formula III wherein $X^1$ is $N(R^{13})CO$, an amine of the Formula X

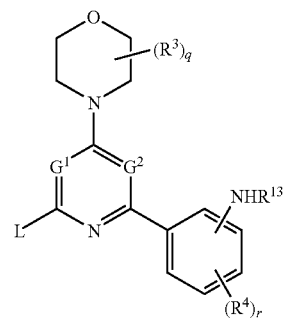

X wherein L, $G^1$, $G^2$, q, $R^3$, r, $R^4$ and $R^{13}$ have any of the meanings defined hereinbefore except that any functional group is protected if necessary, may be acylated, conveniently in the presence of a suitable base as defined hereinbefore, with a carboxylic acid of the Formula V $HO_2C-Q^b$                                                                          V or a reactive derivative thereof as defined hereinafter, wherein $Q^b$ has any of the meanings defined hereinbefore except that any functional group is protected if necessary, whereafter any protecting group that is present is removed by conventional means.

(b) For the production of those compounds of the Formula I wherein $X^1$ is $N(R^{13})CO$, the acylation, conveniently in the presence of a suitable base, of an amine of the Formula IV

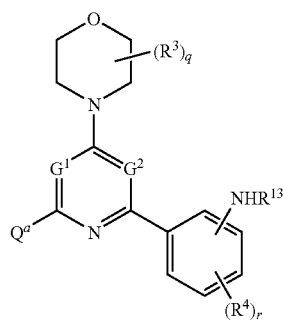

IV wherein $Q^a$, $G^1$, $G^2$, q, $R^3$, r, $R^4$ and $R^{13}$ have any of the meanings defined hereinbefore except that any functional group is protected if necessary, with a carboxylic acid of the Formula V $$HO_2C-Q^b$$ V or a reactive derivative thereof, wherein $Q^b$ has any of the meanings defined hereinbefore except that any functional group is protected if necessary, whereafter any protecting group that is present is removed by conventional means.

A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal amide, for example sodium hexamethyldisilazane, or, for example, an alkali metal hydride, for example sodium hydride.

A suitable reactive derivative of a carboxylic acid of the Formula V is, for example, an acyl halide, for example an acyl chloride formed by the reaction of the acid with an inorganic acid chloride, for example thionyl chloride; a mixed anhydride, for example an anhydride formed by the reaction of the acid with a chloroformate such as isobutyl chloroformate; an active ester, for example an ester formed by the reaction of the acid with a phenol such as pentafluorophenol, with an ester such as pentafluorophenyl trifluoroacetate or with an alcohol such as methanol, ethanol, isopropanol, butanol or N-hydroxybenzotriazole; an acyl azide, for example an azide formed by the reaction of the acid with an azide such as diphenylphosphoryl azide; an acyl cyanide, for example a cyanide formed by the reaction of an acid with a cyanide such as diethylphosphoryl cyanide; or the product of the reaction of the acid with a carbodiimide such as dicyclohexylcarbodiimide or with a uronium compound such as 2-(7-azabenzotriazol-1-yl)-1,1,3,3-tetramethyluronium hexafluorophosphate(V).

The reaction is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene. Conveniently, the reaction is conveniently carried out in the presence of a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 0 to 120° C., preferably at or near ambient temperature.

Pyrimidine starting materials of the Formula IV may be obtained by conventional procedures such as those disclosed in the Examples that are set out hereinafter.

For example, a pyrimidine of the Formula XI

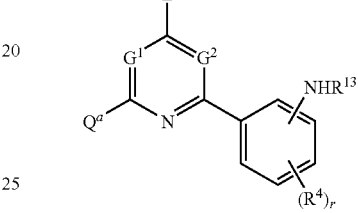

XI wherein L is a displaceable group as defined hereinbefore and $Q^a$, $G^1$, $G^2$, r, $R^4$ and $R^{13}$ have any of the meanings defined hereinbefore except that any functional group is protected if necessary, may be reacted with a morpholine of the Formula VII

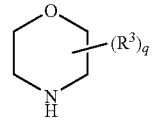

VII wherein q and $R^3$ have any of the meanings defined hereinbefore except that any functional group is protected if necessary, whereafter any protecting group that is present is removed by conventional means.

Alternatively, a pyrimidine of the Formula XII

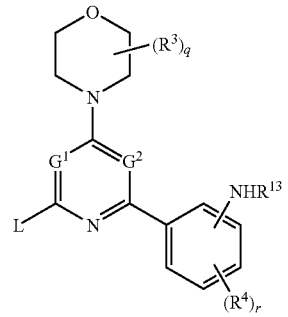

XII wherein L is a displaceable group as defined hereinbefore and $G^1$, $G^2$, q, $R^3$, r, $R^4$ and $R^{13}$ have any of the meanings defined hereinbefore except that any functional group is protected if necessary, may be reacted, conveniently in the presence of a suitable catalyst as defined hereinbefore, with an organoboron reagent of the Formula III

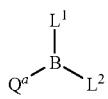
III wherein each of $L^1$ and $L^2$, which may be the same or different, is a suitable ligand as defined hereinbefore and $Q^a$ has any of the meanings defined hereinbefore except that any functional group is protected if necessary, whereafter any protecting group that is present is removed by conventional means.

(c) The reaction of a pyrimidine of the Formula VI

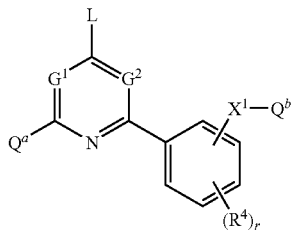
VI wherein L is a displaceable group as defined hereinbefore and $Q^a$, $G^1$, $G^2$, r, $R^4$, $X^1$ and $Q^b$ have any of the meanings defined hereinbefore except that any functional group is protected if necessary, with a morpholine of the Formula VII

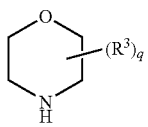
VII wherein q and $R^3$ have any of the meanings defined hereinbefore except that any functional group is protected if necessary, whereafter any protecting group that is present is removed by conventional means.

The reaction may conveniently be carried out in the presence of a suitable acid or in the presence of a suitable base. A suitable acid is, for example, an inorganic acid such as, for example, hydrogen chloride or hydrogen bromide. A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal amide, for example sodium hexamethyldisilazane, or, for example, an alkali metal hydride, for example sodium hydride.

The reaction is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 0 to 250° C., preferably in the range 25 to 150° C.

Typically, the pyrimidine of the Formula VI may be reacted with a morpholine of the Formula VII in the presence of an aprotic solvent such as N,N-dimethylformamide or N,N-dimethylacetamide, conveniently in the presence of a suitable base, for example potassium carbonate or sodium hexamethyldisilazane, and at a temperature in the range, for example, 0 to 200° C., preferably in the range, for example, 25 to 150° C.

Pyrimidine starting materials of the Formula VI may be obtained by conventional procedures such as those disclosed in the Examples that are set out hereinafter.

For example, a pyrimidine of the Formula XIII

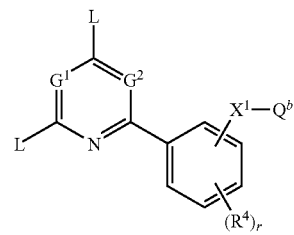
XIII wherein L is a displaceable group as defined hereinbefore and $G^1$, $G^2$, r, $R^4$, $X^1$ and $Q^b$ have any of the meanings defined hereinbefore except that any functional group is protected if necessary, may be reacted, conveniently in the presence of a suitable catalyst as defined hereinbefore, with an organoboron reagent of the Formula III

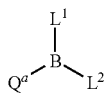
III wherein each of $L^1$ and $L^2$, which may be the same or different, is a suitable ligand as defined hereinbefore and $Q^a$ has any of the meanings defined hereinbefore except that any functional group is protected if necessary, whereafter any protecting group that is present is removed by conventional means.

(d) For the production of those compounds of the Formula I wherein $X^1$ is $N(R^{13})CON(R^{13})$, the coupling, conveniently in the presence of a suitable base as defined hereinbefore, of phosgene, or a chemical equivalent thereof, with an amine of the Formula IV

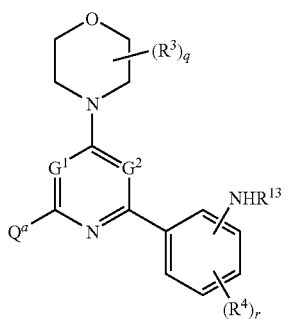
IV and an amine of the Formula VIII $R^{13}NH-Q^b$   VIII wherein $Q^a$, $G^1$, $G^2$, q, $R^3$, r, $R^4$, $R^{13}$ and $Q^b$ have any of the meanings defined hereinbefore except that any functional group is protected if necessary, whereafter any protecting group that is present is removed by conventional means.

A suitable chemical equivalent of phosgene is, for example, a compound of the Formula IX

L-CO-L          IX wherein L is a suitable displaceable group as defined hereinbefore. For example, a suitable displaceable group L is, for example, an alkoxy, aryloxy or sulphonyloxy group, for example a methoxy, phenoxy, methanesulphonyloxy or toluene-4-sulphonyloxy group. Alternatively, a suitable chemical equivalent of phosgene is a carbonate derivative such as disuccinimido carbonate.

The reaction is conveniently carried out in the presence of a suitable inert solvent or diluent as defined hereinbefore and at a temperature in the range, for example, 0 to 120° C., preferably at or near ambient temperature.

(e) The reaction, conveniently in the presence of a suitable catalyst as defined hereinbefore, of a pyrimidine of the Formula XIV

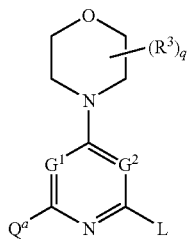

XIV wherein L is a displaceable group as defined hereinbefore and $Q^a$, $G^1$, $G^2$, q and $R^3$ have any of the meanings defined hereinbefore except that any functional group is protected if necessary, with an organoboron reagent of the Formula XV

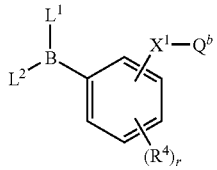

XV wherein each of $L^1$ and $L^2$, which may be the same or different, is a suitable ligand for the boron atom as defined hereinbefore and r, $R^4$, $X^1$ and $Q^b$ have any of the meanings defined hereinbefore except that any functional group is protected if necessary, whereafter any protecting group that is present is removed by conventional means.

Conveniently, the reaction may be carried out in the presence of a suitable base such as an alkali or alkaline earth metal carbonate or hydroxide, for example sodium bicarbonate, sodium carbonate, potassium bicarbonate, potassium carbonate, calcium carbonate, caesium carbonate, sodium hydroxide or potassium hydroxide, or, for example, an alkali metal alkoxide, for example sodium tert-butoxide, or, for example, an alkali metal amide, for example sodium hexamethyldisilazane, or, for example, an alkali metal hydride, for example sodium hydride.

The reaction is conveniently carried out in the presence of a suitable inert solvent or diluent, for example an ether such as tetrahydrofuran, 1,4-dioxan or 1,2-dimethoxyethane, an aromatic solvent such as benzene, toluene or xylene, or an alcohol such as methanol or ethanol, and the reaction is conveniently carried out at a temperature in the range, for example 10 to 250° C., preferably in the range 40 to 150° C.

Aryl-boron reagents of the Formula XV may be obtained by standard procedures of organic chemistry which are within the ordinary skill of an organic chemist, for example by the reaction of an aryl-metal reagent where the metal is, for example, lithium or the magnesium halide portion of a Grignard reagent, with an organoboron compound of the formula L-B($L^1$)($L^2$) wherein L is a displaceable group as defined hereinbefore. Preferably the compound of the formula L-B($L^1$)($L^2$) is, for example, boric acid or a tri-(1-4C)alkyl borate such as tri-isopropyl borate.

In an alternative procedure, the aryl-boron reagent of the Formula XV may be replaced with an organometallic compound of the formula aryl-M wherein M is a metal atom or a metallic group (that is a metal atom bearing suitable ligands). Suitable values for the metal atom include, for example, lithium and copper. Suitable values for the metallic group include, for example, groups which contain a tin, silicon, zirconium, aluminium, magnesium, mercury or zinc atom. Suitable ligands within such a metallic group include, for example, hydroxy groups, (1-6C)alkyl groups such as methyl, ethyl, propyl, isopropyl and butyl groups, halogeno groups such as chloro, bromo and iodo groups, and (1-6C) alkoxy groups such as methoxy, ethoxy, propoxy, isopropoxy and butoxy groups. A particular organometallic compound of the formula aryl-M is, for example, an organotin compound such as a compound of the formula aryl-SnBu$_3$, an organosilicon compound such as a compound of the formula aryl-Si(Me)F$_2$, an organozirconium compound such as a compound of the formula aryl-ZrCl$_3$, an organoaluminum compound such as a compound of the formula aryl-AlEt$_2$, an organomagnesium compound such as a compound of the formula aryl-MgBr, an organomercury compound such as a compound of the formula aryl-HgBr, or an organozinc compound such as a compound of the formula aryl-ZnBr.

Pyrimidine starting materials of the Formula XIV may be obtained by conventional procedures such as those disclosed in the Examples that are set out hereinafter.

(f) For the production of those compounds of the Formula I wherein $X^1$ is CON($R^{13}$), the acylation, conveniently in the presence of a suitable base as defined hereinbefore, of an amine of the Formula VIII $R^{13}$NH-$Q^b$          VIII wherein $R^{13}$ and $Q^b$ have any of the meanings defined hereinbefore except that any functional group is protected if necessary, with a carboxylic acid, or a reactive derivative thereof as defined hereinbefore, of the Formula XVI

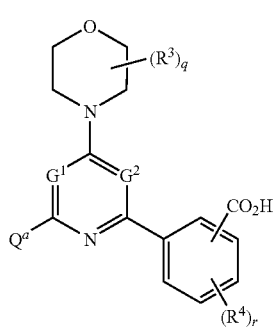

XVI wherein $Q^a$, $G^1$, $G^2$, q, $R^3$, r and $R^4$ have any of the meanings defined hereinbefore except that any functional group is protected if necessary, whereafter any protecting group that is present is removed by conventional means.

The reaction is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene. Conveniently, the reaction is conveniently carried out in the presence of a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 0 to 120° C., preferably at or near ambient temperature.

Pyrimidine starting materials of the Formula XVI may be obtained by conventional procedures that are analogous to those disclosed in the Examples that are set out hereinafter.

(g) For the production of those compounds of the Formula I wherein $X^1$ is CO and $Q^b$ is a N-linked heterocyclyl group, the acylation, conveniently in the presence of a suitable base as defined hereinbefore, of a N-containing heterocyclic compound wherein any functional group is protected if necessary, with a carboxylic acid, or a reactive derivative thereof as defined hereinbefore, of the Formula XVI

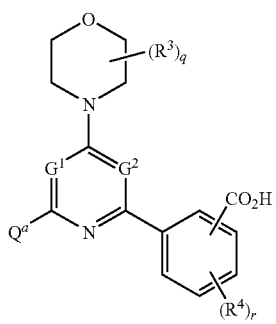

XVI wherein $Q^a$, $G^1$, $G^2$, q, $R^3$, r and $R^4$ have any of the meanings defined hereinbefore except that any functional group is protected if necessary, whereafter any protecting group that is present is removed by conventional means.

The reaction is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene. Conveniently, the reaction is conveniently carried out in the presence of a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 0 to 120° C., preferably at or near ambient temperature.

The pyrimidine derivative of the Formula I may be obtained from the process variants described hereinbefore in the form of the free base or alternatively it may be obtained in the form of a salt with the acid of the formula H-L wherein L has the meaning defined hereinbefore. When it is desired to obtain the free base from the salt, the salt may be treated with a suitable base, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

When a pharmaceutically-acceptable salt of a pyrimidine derivative of the Formula I is required, for example an acid-addition salt, it may be obtained by, for example, reaction of said pyrimidine derivative with a suitable acid using a conventional procedure.

When a pharmaceutically-acceptable pro-drug of a pyrimidine derivative of the Formula I is required, it may be obtained using a conventional procedure. For example, an in vivo cleavable ester of a pyrimidine derivative of the Formula I may be obtained by, for example, reaction of a compound of the Formula I containing a carboxy group with a pharmaceutically-acceptable alcohol or by reaction of a compound of the Formula I containing a hydroxy group with a pharmaceutically-acceptable carboxylic acid. For example, an in vivo cleavable amide of a pyrimidine derivative of the Formula I may be obtained by, for example, reaction of a compound of the Formula I containing a carboxy group with a pharmaceutically-acceptable amine or by reaction of a compound of the Formula I containing an amino group with a pharmaceutically-acceptable carboxylic acid.

Many of the intermediates defined herein are novel and these are provided as a further feature of the invention. For example, many compounds of the Formulae II, IV, VI, XIV and XVI are novel compounds.

Biological Assays

The following assays can be used to measure the effects of the compounds of the present invention as PI3 kinase inhibitors, as inhibitors in vitro of the activation of PI3 kinase signalling pathways, as inhibitors in vitro of the proliferation of MDA-MB-468 human breast adenocarcinoma cells, and as inhibitors in vivo of the growth in nude mice of xenografts of MDA-MB-468 carcinoma tissue.

(a) In Vitro Enzyme Assay

The assay used AlphaScreen technology (Gray et al., *Analytical Biochemistry*, 2003, 313: 234-245) to determine the ability of test compounds to inhibit phosphorylation by recombinant Type I PI3K enzymes of the lipid PI(4,5)P2.

DNA fragments encoding human PI3K catalytic and regulatory subunits were isolated from cDNA libraries using standard molecular biology and PCR cloning techniques. The selected DNA fragments were used to generate baculovirus expression vectors. In particular, full length DNA of each of the p110α, p110β and p110δ Type Ia human PI3K p110 isoforms (EMBL Accession Nos. HSU79143, S67334, Y10055 for p110α, p110β and p110δ respectively) were sub-cloned into a pDEST10 vector (Invitrogen Limited, Fountain drive, Paisley, UK). The vector is a Gateway-adapted version of Fastbac1 containing a 6-His epitope tag. A truncated form of Type Ib human PI3K p110γ isoform corresponding to amino acid residues 144-1102 (EMBL Accession No. X8336A) and the full length human p85α regulatory subunit (EMBL Accession No. HSP13KIN) were also sub-cloned into pFastBac1 vector containing a 6-His epitope tag. The Type Ia p110 constructs were co-expressed with the p85α regulatory subunit. Following expression in the baculovirus system using standard baculovirus expression techniques, expressed proteins were purified using the His epitope tag using standard purification techniques.

DNA corresponding to amino acids 263 to 380 of human Grp1 PH domain was isolated from a cDNA library using standard molecular biology and PCR cloning techniques. The resultant DNA fragment was sub-cloned into a pGEX 4T1 *E. coli* expression vector containing a GST epitope tag (Amersham Pharmacia Biotech, Rainham, Essex, UK) as described by Gray et al., *Analytical Biochemistry,* 2003, 313: 234-245). The GST-tagged Grp1 PH domain was expressed and purified using standard techniques.

Test compounds were prepared as 10 mM stock solutions in DMSO and diluted into water as required to give a range of final assay concentrations. Aliquots (2 µl) of each compound dilution were placed into a well of a Greiner 384-well low volume (LV) white polystyrene plate (Greiner Bio-one, Brunel Way, Stonehouse, Gloucestershire, UK Catalogue No. 784075). A mixture of each selected recombinant purified PI3K enzyme (15 ng), DiC8-PI(4,5)P2 substrate (40 µM; Cell Signals Inc., Kinnear Road, Columbus, USA, Catalogue No. 901), adenosine triphosphate (ATP; 4 µM) and a buffer solution [comprising Tris-HCl pH7.6 buffer (40 mM, 10 µl), 3-[(3-cholamidopropyl)dimethylammonio]-1-propane-sulphonate (CHAPS; 0.04%), dithiothreitol (DTT; 2 mM) and magnesium chloride (10 mM)] was agitated at ambient temperature for 20 minutes.

Control wells that produced a minimum signal corresponding to maximum enzyme activity were created by using 5% DMSO instead of test compound. Control wells that produced a maximum signal corresponding to fully inhibited enzyme were created by adding wortmannin (6 µM; Calbiochem/Merck Bioscience, Padge Road, Beeston, Nottingham, UK, Catalogue No. 681675) instead of test compound. These assay solutions were also agitated for 20 minutes at ambient temperature.

Each reaction was stopped by the addition of 10 µl of a mixture of EDTA (100 mM), bovine serum albumin (BSA, 0.045%) and Tris-HCl pH7.6 buffer (40 mM).

Biotinylated-DiC8-PI(3,4,5)P3 (50 nM; Cell Signals Inc., Catalogue No. 107), recombinant purified GST-Grp1 PH protein (2.5 nM) and AlphaScreen Anti-GST donor and acceptor beads (100 ng; Packard Bioscience Limited, Station Road, Pangbourne, Berkshire, UK, Catalogue No. 6760603M) were added and the assay plates were left for about 5 to 20 hours at ambient temperature in the dark. The resultant signals arising from laser light excitation at 680 nm were read using a Packard AlphaQuest instrument.

PI(3,4,5)P3 is formed in situ as a result of PI3K mediated phosphorylation of PI(4,5)P2. The GST-Grp1 PH domain protein that is associated with AlphaScreen Anti-GST donor beads forms a complex with the biotinylated PI(3,4,5)P3 that is associated with Alphascreen Streptavidin acceptor beads. The enzymatically-produced PI(3,4,5)P3 competes with biotinylated PI(3,4,5)P3 for binding to the PH domain protein. Upon laser light excitation at 680 nm, the donor bead: acceptor bead complex produces a signal that can be measured. Accordingly, PI3K enzyme activity to form PI(3,4,5)P3 and subsequent competition with biotinylated PI(3,4,5)P3 results in a reduced signal. In the presence of a PI3K enzyme inhibitor, signal strength is recovered.

PI3K enzyme inhibition for a given test compound was expressed as an $IC_{50}$ value.

(b) In Vitro Phospho-Ser473 Akt Assay

This assay determines the ability of test compounds to inhibit phosphorylation of Serine 473 in Akt as assessed using Acumen Explorer technology (Acumen Bioscience Limited), a plate reader that can be used to rapidly quantitate features of images generated by laser-scanning.

A MDA-MB-468 human breast adenocarcinoma cell line (LGC Promochem, Teddington, Middlesex, UK, Catalogue No. HTB-132) was routinely maintained at 37° C. with 5% $CO_2$ up to a confluency of 70-90% in Dulbecco's modified Eagle's growth medium (DMEM; Invitrogen Limited, Paisley, UK Catalogue No. 41966-029) containing 10% heat-inactivated foetal calf serum (FCS; Sigma, Poole, Dorset, UK, Catalogue No. F0392) and 1% L-glutamine (Gibco, Catalogue No. 25030-024).

For the assay, the cells were detached from the culture flask using 'Accutase' (Innovative Cell Technologies Inc., San Diego, Calif., USA; Catalogue No. AT104) using standard tissue culture methods and resuspended in media to give $1.7 \times 10^5$ cells per ml. Aliquots (90 µl) were seeded into each of the inner 60 wells of a black Packard 96 well plate (PerkinElmer, Boston, Mass., USA; Catalogue No. 6005182) to give a density of ~15000 cells per well. Aliquots (90 µl) of culture media were placed in the outer wells to prevent edge effects. The cells were incubated overnight at 37° C. with 5% $CO_2$ to allow them to adhere.

On day 2, the cells were treated with test compounds and incubated for 2 hours at 37° C. with 5% $CO_2$. Test compounds were prepared as 10 mM stock solutions in DMSO and serially diluted as required with growth media to give a range of concentrations that were 10-fold the required final test concentrations. Aliquots (10 µl) of each compound dilution were placed in a well (in triplicate) to give the final required concentrations. As a minimum response control, each plate contained wells having a final concentration of 100 µM LY294002 (Calbiochem, Beeston, UK, Catalogue No. 440202). As a maximum response control, wells contained 1% DMSO instead of test compound. Following incubation, the contents of the plates were fixed by treatment with a 1.6% aqueous formaldehyde solution (Sigma, Poole, Dorset, UK, Catalogue No. F1635) at ambient temperature for 1 hour.

All subsequent aspiration and wash steps were carried out using a Tecan 96 well plate washer (aspiration speed 10 mm/sec). The fixing solution was removed and the contents of the plates were washed with phosphate-buffered saline (PBS; 50 µl; Gibco, Catalogue No. 10010015). The contents of the plates were treated for 10 minutes at ambient temperature with an aliquot (50 µl) of a cell permeabilisation buffer consisting of a mixture of PBS and 0.5% Tween-20. The 'permeabilisation' buffer was removed and non-specific binding sites were blocked by treatment for 1 hour at ambient temperature of an aliquot (50 µl) of a blocking buffer consisting of 5% dried skimmed milk ['Marvel' (registered trade mark); Premier Beverages, Stafford, GB] in a mixture of PBS and 0.05% Tween-20. The 'blocking' buffer was removed and the cells were incubated for 1 hour at ambient temperature with rabbit anti phospho-Akt (Ser473) antibody solution (50 µl per well; Cell Signalling, Hitchin, Herts, U.K., Catalogue No 9277) that had been diluted 1:500 in 'blocking' buffer. Cells were washed three times in a mixture of PBS and 0.05% Tween-20. Subsequently, cells were incubated for 1 hour at ambient temperature with Alexafluor488 labelled goat anti-rabbit IgG (50 µl per well; Molecular Probes, Invitrogen Limited, Paisley, UK, Catalogue No. A11008) that had been diluted 1:500 in 'blocking' buffer. Cells were washed 3 times with a mixture of PBS and 0.05% Tween-20. An aliquot of PBS (50 µl) was added to each well and the plates were sealed with black plate sealers and the fluorescence signal was detected and analysed.

Fluorescence dose response data obtained with each compound were analysed and the degree of inhibition of Serine 473 in Akt was expressed as an $IC_{50}$ value.

(c) In Vitro MDA-MB-468 Human Breast Adenocarcinoma Proliferation Assay

This assay determines the ability of test compounds to inhibit cell proliferation as assessed using Cellomics Arrayscan technology. A MDA-MB-468 human breast adenocarcinoma cell line (LGC Promochem, Catalogue No. HTB-132) was routinely maintained as described in Biological Assay (b) hereinbefore.

For the proliferation assay, the cells were detached from the culture flask using Accutase and seeded into the inner 60 wells of a black Packard 96 well plate at a density of 8000 cells per well in 100 µl of complete growth media. The outer wells contained 100 µl of sterile PBS. The cells were incubated overnight at 37° C. with 5% $CO_2$ to allow them to adhere.

On day 2, the cells were treated with test compounds and incubated for 48 hours at 37° C. with 5% $CO_2$. Test compounds were prepared as 10 mM stock solutions in DMSO and serially diluted as required with growth media to give a range of test concentrations. Aliquots (50 µl) of each compound dilution were placed in a well and the cells were incubated for 2 days at 37° C. with 5% $CO_2$. Each plate contained control wells without test compound.

On day 4, BrdU labelling reagent (Sigma, Catalogue No. B9285) at a final dilution of 1:1000 was added and the cells were incubated for 2 hours at 37° C. The medium was removed and the cells in each well were fixed by treatment with 100 µl of a mixture of ethanol and glacial acetic acid (90% ethanol, 5% glacial acetic acid and 5% water) for 30 minutes at ambient temperature. The cells in each well were washed twice with PBS (100 µl). Aqueous hydrochloric acid (2M, 100 µl) was added to each well. After 20 minutes at ambient temperature, the cells were washed twice with PBS. Hydrogen peroxide (3%, 50 µl; Sigma, Catalogue No. H1009) was added to each well. After 10 minutes at ambient temperature, the wells were washed again with PBS.

BrdU incorporation was detected by incubation for 1 hour at ambient temperature with mouse anti-BrdU antibody (50 µl; Caltag, Burlingame, Calif., US; Catalogue No. MD5200) that was diluted 1:40 in PBS containing 1% BSA and 0.05% Tween-20. Unbound antibody was removed with two washes of PBS. For visualisation of incorporated BrdU, the cells were treated for 1 hour at ambient temperature with PBS (50 µl) and 0.05% Tween-20 buffer containing a 1:1000 dilution of Alexa fluor 488-labelled goat anti-mouse IgG. For visualisation of the cell nucleus, a 1:1000 dilution of Hoechst stain (Molecular Probes, Catalogue No. H3570) was added. Each plate was washed in turn with PBS. Subsequently, PBS (100 µl) was added to each well and the plates were analysed using a Cellomics array scan to assess total cell number and number of BrdU positive cells.

Fluorescence dose response data obtained with each compound were analysed and the degree of inhibition of MDA-MB-468 cell growth was expressed as an $IC_{50}$ value.

(d) In Vivo MDA-MB-468 Xenograft Growth Assay

This test measures the ability of compounds to inhibit the growth of MDA-MB-468 human breast adenocarcinoma cells grown as a tumour in athymic nude mice (Alderley Park nu/nu strain). A total of about $5 \times 10^6$ MDA-MB-468 cells in matrigel (Beckton Dickinson Catalogue No. 40234) are injected subcutaneously into the left flank of each test mouse and the resultant tumours are allowed to grow for about 14 days. Tumour size is measured twice weekly using calipers and a theoretical volume is calculated. Animals are selected to provide control and treatment groups of approximately equal average tumour volume. Test compounds are prepared as a ball-milled suspension in 1% polysorbate vehicle and dosed orally once daily for a period of about 28 days. The effect on tumour growth is assessed.

Although the pharmacological properties of the compounds of the Formula I vary with structural change as expected, in general activity possessed by compounds of the Formula I, may be demonstrated at the following concentrations or doses in one or more of the above tests (a), (b), (c) and (d):—

Test (a):—$IC_{50}$ versus p110α Type Ia human PI3K in the range, for example, 0.1-50 µM;
Test (b):—$IC_{50}$ in the range, for example, 0.1-50 µM;
Test (c):—$IC_{50}$ in the range, for example, 0.1-50 µM;
Test (d):—activity in the range, for example, 1-200 mg/kg/day.

For example, the pyrimidine compound disclosed within Example 1 possesses activity in Test (a) with an $IC_{50}$ versus p110α Type Ia human PI3K of approximately 10 µM, and in Test (b) with an $IC_{50}$ of approximately 50 µM; the pyrimidine compound disclosed within Example 2 possesses activity in Test (a) with an $IC_{50}$ of approximately 12 µM, and in Test (b) with an $IC_{50}$ of approximately 28 µM; the pyrimidine compound disclosed within Example 4 possesses activity in Test (a) with an $IC_{50}$ of approximately 0.6 µM; and the pyrimidine compound disclosed within Example 5 possesses activity in Test (a) with an $IC_{50}$ of approximately 0.5 µM, and in Test (b) with an $IC_{50}$ of approximately 1 µM.

No untoward toxicological effects are expected when a compound of Formula I, or a pharmaceutically-acceptable salt thereof, as defined hereinbefore is administered at the dosage ranges defined hereinafter.

According to a further aspect of the invention there is provided a pharmaceutical composition which comprises a pyrimidine derivative of the Formula I, or a pharmaceutically-acceptable salt, solvate or pro-drug thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 1 mg to 1 g of active agent (more suitably from 1 to 250 mg, for example from 1 to 100 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the disease state, the age and sex of the animal or patient and the route of administration, according to well known principles of medicine.

In using a compound of the Formula I for therapeutic or prophylactic purposes it will generally be administered so that a daily dose in the range, for example, 1 mg/kg to 100 mg/kg body weight is received, given if required in divided doses. In general, lower doses will be administered when a parenteral route is employed. Thus, for example, for intravenous administration, a dose in the range, for example, 1 mg/kg to 25 mg/kg body weight will generally be used. Similarly, for administration by inhalation, a dose in the range, for example, 1 mg/kg to 25 mg/kg body weight will be used. Oral administration is however preferred, particularly in tablet form. Typically, unit dosage forms will contain about 10 mg to 0.5 g of a compound of this invention.

As stated above, it is known that PI3K enzymes contribute to tumorigenesis by one or more of the effects of mediating proliferation of cancer and other cells, mediating angiogenic events and mediating the motility, migration and invasiveness of cancer cells. We have found that the pyrimidine derivatives of the present invention possess potent anti-tumour activity which it is believed is obtained by way of inhibition of one or more of the Class I PI3K enzymes (such as the Class Ia PI3K enzymes and/or the Class Ib PI3K enzyme) that are involved in the signal transduction steps which lead to the proliferation and survival of tumour cells and the invasiveness and migratory ability of metastasising tumour cells.

Accordingly, the derivatives of the present invention are of value as anti-tumour agents, in particular as selective inhibitors of the proliferation, survival, motility, dissemination and invasiveness of mammalian cancer cells leading to inhibition of tumour growth and survival and to inhibition of metastatic tumour growth. Particularly, the pyrimidine derivatives of the present invention are of value as anti-proliferative and anti-invasive agents in the containment and/or treatment of solid tumour disease. Particularly, the compounds of the present invention are expected to be useful in the prevention or treatment of those tumours which are sensitive to inhibition of one or more of the multiple PI3K enzymes such as the Class Ia PI3K enzymes and the Class Ib PI3K enzyme that are involved in the signal transduction steps which lead to the proliferation and survival of tumour cells and the migratory ability and invasiveness of metastasising tumour cells. Further, the compounds of the present invention are expected to be useful in the prevention or treatment of those tumours which are mediated alone or in part by inhibition of PI3K enzymes such as the Class Ia PI3K enzymes and the Class Ib PI3K enzyme, i.e. the compounds may be used to produce a PI3K enzyme inhibitory effect in a warm-blooded animal in need of such treatment.

As stated hereinbefore, inhibitors of PI3K enzymes should be of therapeutic value for treatment of, for example, cancer of the breast, colorectum, lung (including small cell lung cancer, non-small cell lung cancer and bronchioalveolar cancer) and prostate, and of cancer of the bile duct, bone, bladder, head and neck, kidney, liver, gastrointestinal tissue, oesophagus, ovary, pancreas, skin, testes, thyroid, uterus, cervix and vulva, and of leukaemias [including acute lymphocytic leukaemia (ALL) and chronic myelogenous leukaemia (CML)], multiple myeloma and lymphomas.

According to a further aspect of the invention there is provided a pyrimidine derivative of the Formula I, or a pharmaceutically-acceptable salt, solvate or pro-drug thereof, as defined hereinbefore for use as a medicament in a warm-blooded animal such as man.

According to a further aspect of the invention, there is provided a pyrimidine derivative of the Formula I, or a pharmaceutically-acceptable salt, solvate or pro-drug thereof, as defined hereinbefore for use in the production of an anti-proliferative effect in a warm-blooded animal such as man.

According to a further feature of this aspect of the invention there is provided a pyrimidine derivative of the Formula I, or a pharmaceutically-acceptable salt, solvate or pro-drug thereof, as defined hereinbefore for use in a warm-blooded animal such as man as an anti-invasive agent in the containment and/or treatment of solid tumour disease.

According to a further aspect of the invention, there is provided the use of a pyrimidine derivative of the Formula I, or a pharmaceutically-acceptable salt, solvate or pro-drug thereof, as defined hereinbefore for the production of an anti-proliferative effect in a warm-blooded animal such as man.

According to a further feature of this aspect of the invention there is provided the use of a pyrimidine derivative of the Formula I, or a pharmaceutically-acceptable salt, solvate or pro-drug thereof, as defined hereinbefore in the manufacture of a medicament for use in the production of an anti-proliferative effect in a warm-blooded animal such as man.

According to a further feature of this aspect of the invention there is provided the use of a pyrimidine derivative of the Formula I, or a pharmaceutically-acceptable salt, solvate or pro-drug thereof, as defined hereinbefore in the manufacture of a medicament for use in a warm-blooded animal such as man as an anti-invasive agent in the containment and/or treatment of solid tumour disease.

According to a further feature of this aspect of the invention there is provided a method for producing an anti-proliferative effect in a warm-blooded animal, such as man, in need of such treatment which comprises administering to said animal an effective amount of a pyrimidine derivative of the Formula I, or a pharmaceutically-acceptable salt, solvate or pro-drug thereof, as defined hereinbefore.

According to a further feature of this aspect of the invention there is provided a method for producing an anti-invasive effect by the containment and/or treatment of solid tumour disease in a warm-blooded animal, such as man, in need of such treatment which comprises administering to said animal an effective amount of a pyrimidine derivative of the Formula I, or a pharmaceutically-acceptable salt thereof, solvate or pro-drug, as defined hereinbefore.

According to a further aspect of the invention there is provided the use of a pyrimidine derivative of the Formula I, or a pharmaceutically-acceptable salt, solvate or pro-drug thereof, as defined hereinbefore in the manufacture of a medicament for use in the prevention or treatment of solid tumour disease in a warm-blooded animal such as man.

According to a further feature of this aspect of the invention there is provided a method for the prevention or treatment of solid tumour disease in a warm-blooded animal, such as man, in need of such treatment which comprises administering to said animal an effective amount of a pyrimidine derivative of the Formula I, or a pharmaceutically-acceptable salt, solvate or pro-drug thereof, as defined hereinbefore.

According to a further aspect of the invention there is provided a pyrimidine derivative of the Formula I, or a pharmaceutically-acceptable salt, solvate or pro-drug thereof, as defined hereinbefore for use in the prevention or treatment of those tumours which are sensitive to inhibition of PI3K enzymes (such as the Class Ia enzymes and/or the Class Ib PI3K enzyme) that are involved in the signal transduction steps which lead to the proliferation, survival, invasiveness and migratory ability of tumour cells.

According to a further feature of this aspect of the invention there is provided the use of a pyrimidine derivative of the Formula I, or a pharmaceutically-acceptable salt, solvate or pro-drug thereof, as defined hereinbefore in the manufacture of a medicament for use in the prevention or treatment of those tumours which are sensitive to inhibition of PI3K enzymes (such as the Class Ia enzymes and/or the Class Ib PI3K enzyme) that are involved in the signal transduction steps which lead to the proliferation, survival, invasiveness and migratory ability of tumour cells.

According to a further feature of this aspect of the invention there is provided a method for the prevention or treatment of those tumours which are sensitive to inhibition of PI3K enzymes (such as the Class Ia enzymes and/or the Class Ib PI3K enzyme) that are involved in the signal transduction steps which lead to the proliferation, survival, invasiveness and migratory ability of tumour cells which comprises administering to said animal an effective amount of a pyrimidine derivative of the Formula I, or a pharmaceutically-acceptable salt, solvate or pro-drug thereof, as defined hereinbefore.

According to a further aspect of the invention there is provided a pyrimidine derivative of the Formula I, or a pharmaceutically-acceptable salt, solvate or pro-drug thereof, as defined hereinbefore for use in providing a PI3K enzyme inhibitory effect (such as a Class Ia PI3K enzyme or Class Ib PI3K enzyme inhibitory effect).

According to a further feature of this aspect of the invention there is provided the use of a pyrimidine derivative of the Formula I, or a pharmaceutically-acceptable salt, solvate or pro-drug thereof, as defined hereinbefore in the manufacture of a medicament for use in providing a PI3K enzyme inhibitory effect (such as a Class Ia PI3K enzyme or Class Ib PI3K enzyme inhibitory effect).

According to a further aspect of the invention there is also provided a method for providing a PI3K enzyme inhibitory effect (such as a Class Ia PI3K enzyme or Class Ib PI3K enzyme inhibitory effect) which comprises administering an effective amount of a pyrimidine derivative of the Formula I, or a pharmaceutically-acceptable salt, solvate or pro-drug thereof, as defined hereinbefore.

As stated hereinbefore, certain compounds of the present invention, possess substantially better potency against Class Ia PI3K enzymes than against the Class Ib PI3K enzyme or against EGF receptor tyrosine kinase, VEGF receptor tyrosine kinase or Src non-receptor tyrosine kinase enzymes. Such compounds possess sufficient potency against Class Ia PI3K enzymes that they may be used in an amount sufficient to inhibit Class Ia PI3K enzymes whilst demonstrating little activity against the Class Ib PI3K enzyme or against EGF receptor tyrosine kinase, VEGF receptor tyrosine kinase or Src non-receptor tyrosine kinase enzymes. Such compounds are likely to be useful for the selective inhibition of Class Ia PI3K enzymes and are likely to be useful for the effective treatment of, for example Class Ia PI3K enzyme driven tumours.

According to this aspect of the invention there is provided a pyrimidine derivative of the Formula I, or a pharmaceutically-acceptable salt, solvate or pro-drug thereof, as defined hereinbefore for use in providing a selective Class Ia PI3K enzyme inhibitory effect.

According to a further feature of this aspect of the invention there is provided the use of a pyrimidine derivative of the Formula I, or a pharmaceutically-acceptable salt, solvate or pro-drug thereof, as defined hereinbefore in the manufacture of a medicament for use in providing a selective Class Ia PI3K enzyme inhibitory effect.

According to a further aspect of the invention there is also provided a method for providing a selective Class Ia PI3K enzyme inhibitory effect which comprises administering an effective amount of a pyrimidine derivative of the Formula I, or a pharmaceutically-acceptable salt, solvate or pro-drug thereof, as defined hereinbefore.

By "a selective Class Ia PI3K enzyme inhibitory effect" is meant that the pyrimidine derivatives of the Formula I are more potent against Class Ia PI3K enzymes than against other kinase enzymes. In particular, some of the compounds according to the invention are more potent against Class Ia PI3K enzymes than against other kinases such as receptor or non-receptor tyrosine kinases or serine/threonine kinases. For example a selective Class Ia PI3K enzyme inhibitor according to the invention is at least 5 times more potent, preferably at least 10 times more potent, more preferably at least 100 times more potent, against Class Ia PI3K enzymes than against other kinases.

According to a further feature of the invention there is provided a pyrimidine derivative of the Formula I, or a pharmaceutically-acceptable salt, solvate or pro-drug, as defined hereinbefore for use in the treatment of cancer of the breast, colorectum, lung (including small cell lung cancer, non-small cell lung cancer and bronchioalveolar cancer) and prostate.

According to a further feature of this aspect of the invention there is provided a pyrimidine derivative of the Formula I, or a pharmaceutically-acceptable salt, solvate or pro-drug thereof, as defined hereinbefore for use in the treatment of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

According to a further feature of this aspect of the invention there is provided the use of a pyrimidine derivative of the Formula I, or a pharmaceutically-acceptable salt, solvate or pro-drug thereof, as defined hereinbefore in the manufacture of a medicament for use in the treatment of cancer of the breast, colorectum, lung (including small cell lung cancer, non-small cell lung cancer and bronchioalveolar cancer) and prostate.

According to a further feature of this aspect of the invention there is provided the use of a pyrimidine derivative of the Formula I, or a pharmaceutically-acceptable salt, solvate or pro-drug thereof, as defined hereinbefore in the manufacture of a medicament for use in the treatment of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

According to a further feature of this aspect of the invention there is provided a method for treating cancer of the breast, colorectum, lung (including small cell lung cancer, non-small cell lung cancer and bronchioalveolar cancer) and prostate in a warm blooded animal such as man that is in need of such treatment which comprises administering an effective amount of a pyrimidine derivative of the Formula I, or a pharmaceutically-acceptable salt, solvate or pro-drug thereof, as defined hereinbefore.

According to a further feature of this aspect of the invention there is provided a method for treating cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas in a warm blooded animal such as man that is in need of such treatment which comprises administering an effective amount of a pyrimidine derivative of the Formula I, or a pharmaceutically-acceptable salt, solvate or pro-drug thereof, as defined hereinbefore.

As stated hereinbefore, the in vivo effects of a compound of the Formula I may be exerted in part by one or more metabolites that are formed within the human or animal body after administration of a compound of the Formula I.

The anti-cancer treatment defined hereinbefore may be applied as a sole therapy or may involve, in addition to the pyrimidine derivative of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyqyuinazoline (AZD0530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib; BMS-354825; *J. Med. Chem.*, 2004, 47, 6658-6661), and metalloproteinase inhibitors like marimastat and inhibitors of urokinase plasminogen activator receptor function);

(iv) inhibitors of growth factor function: for example such inhibitors include growth factor antibodies and growth factor receptor antibodies (for example the anti-erbB2 antibody trastuzumab [Herceptin™] and the anti-erbB1 antibody cetuximab [C225]); such inhibitors also include, for example, tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033) and erbB2 tyrosine kinase inhibitors such as lapatinib), inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)) and inhibitors of cell signalling through MEK, AKT and/or PI3K kinases;

(v) antiangiogenic agents such as those which inhibit the effects of vascular endothelial growth factor, [for example the anti-vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy) quinazoline (AZD2171; Example 240 within WO 00/47212), vatalanib (PTK787; WO 98/35985) and SU11248 (sunitinib; WO 01/60814), and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a pharmaceutical product comprising a pyrimidine derivative of the formula I as defined hereinbefore and an additional anti-tumour agent as defined hereinbefore for the conjoint treatment of cancer.

Although the compounds of the Formula I are primarily of value as therapeutic agents for use in warm-blooded animals (including man), they are also useful whenever it is required to inhibit the effects of PI3K enzymes. Thus, they are useful as pharmacological standards for use in the development of new biological tests and in the search for new pharmacological agents.

The invention will now be illustrated in the following Examples in which, generally:

(i) operations were carried out at ambient temperature, i.e. in the range 17 to 25° C. and under an atmosphere of an inert gas such as nitrogen or argon unless otherwise stated;

(ii) reactions conducted under microwave radiation were performed using a Smith Synthesiser (300 KWatts) on either the normal or high setting, which instrument makes use of a temperature probe to adjust the microwave power output automatically in order to maintain the required temperature;

(iii) in general, the course of reactions was followed by thin layer chromatography (TLC) and/or analytical high pressure liquid chromatography (HPLC); the reaction times that are given are not necessarily the minimum attainable;

(iv) when necessary, organic solutions were dried over anhydrous magnesium sulphate, work-up procedures were carried out after removal of residual solids by filtration, evaporations were carried out by rotary evaporation in vacuo;

(v) yields, where present, are not necessarily the maximum attainable, and, when necessary, reactions were repeated if a larger amount of the reaction product was required;

(vi) in general, the structures of the end-products of the Formula I were confirmed by nuclear magnetic resonance (NMR) and/or mass spectral techniques; electrospray mass spectral data were obtained using a Waters ZMD or Waters ZQ LC/mass spectrometer acquiring both positive and negative ion data, generally, only ions relating to the parent structure are reported; proton NMR chemical shift values were measured on the delta scale using a Bruker Spectrospin DPX300 spectrometer operating at a field strength of 300 MHz; the following abbreviations have been used: s, singlet; d, doublet; t, triplet; q, quartet; m, multiplet; br, broad;

(vii) unless stated otherwise compounds containing an asymmetric carbon and/or sulphur atom were not resolved;

(viii) intermediates were not necessarily fully purified but their structures and purity were assessed by TLC, analytical HPLC, infra-red (IR) and/or NMR analysis;

(ix) unless otherwise stated, column chromatography (by the flash procedure) and medium pressure liquid chromatography (MPLC) were performed on Merck Kieselgel silica (Art. 9385);

(x) preparative HPLC was performed on C18 reversed-phase silica, for example on a Waters 'Xterra' preparative reversed-phase column (5 microns silica, 19 mm diameter, 100 mm length) using decreasingly polar mixtures as eluent, for example decreasingly polar mixtures of water (containing 1% acetic acid or 1% aqueous ammonium hydroxide (d=0.88) and acetonitrile;

(xi) where certain compounds were obtained as an acid-addition salt, for example a mono-hydrochloride salt or a di-hydrochloride salt, the stoichiometry of the salt was based on the number and nature of the basic groups in the compound, the exact stoichiometry of the salt was generally not determined, for example by means of elemental analysis data;

(xii) the following abbreviations have been used:—
DMSO dimethylsulphoxide
DMA N,N-dimethylacetamide

EXAMPLE 1

4-(5-hydroxymethylthien-2-yl)-6-morpholino-2-(3-piperidin-4-ylcarbonylaminophenyl)pyrimidine A mixture of 2-[3-(1-tert-butoxycarbonylpiperidin-4-ylcarbonylamino)phenyl]-4-chloro-6-morpholinopyrimidine (0.054 g), 5-hydroxymethylthien-2-ylboronic acid (0.021 g), caesium fluoride (0.046 g), a [1,1'-bis(diphenylphosphino) ferrocene]dichloropalladium(II) 1:1 complex with methylene chloride (3 mg), and methanol (2 ml) was stirred and heated to 120° C. using microwave radiation for 20 minutes under an atmosphere of nitrogen in a sealed glass tube. The resultant reaction mixture was evaporated and the residue was partitioned between methylene chloride and water. The organic solution was dried over magnesium sulphate and evaporated. The residue was purified by column chromatography on silica using an increasingly polar gradient of 0% to 5% methanol in methylene chloride as eluent. There was thus obtained 2-[3-(N-tert-butoxycarbonylpiperidin-4-ylcarbonylamino)phenyl]-4-(5-hydroxymethylthien-2-yl)-6-morpholinopyrimidine as a gum. Trifluoroacetic acid (2 ml) was added to the material so obtained and the mixture was stirred at ambient temperature for 30 minutes. The mixture was evaporated and the residue was purified by HPLC using a Waters 'Xterra' preparative reversed-phase column (5 microns silica, 19 mm diameter, 100 mm length) using decreasingly polar mixtures of water (containing 1% of a concentrated (d=0.88) aqueous ammonium hydroxide solution) and acetonitrile as eluent. There was thus obtained the title compound as a solid (0.015 g); NMR Spectrum: (DMSO-$d_6$) 1.55-1.66 (m, 2H), 3.04 (d, 2H), 3.77 (d, 8H), 4.69 (d, 2H), 5.57 (t, 1H), 7.05 (d, 1H), 7.19 (s, 1H), 7.4 (t, 1H), 7.9-7.95 (m, 2H), 8.07 (d, 1H), 8.48 (s, 1H), 10.01 (s, 1H); Mass Spectrum: M+H$^+$480.

The 2-[3-(1-tert-butoxycarbonylpiperidin-4-ylcarbonylamino)phenyl]-4-chloro-6-morpholinopyrimidine used as a starting material was prepared as follows:—

3-Nitrobenzamidine hydrochloride (20 g) was added to a stirred solution of sodium methoxide (20.5 g) in methanol (200 ml) and the mixture was stirred under an atmosphere of nitrogen at ambient temperature for 30 minutes. Diethyl malonate (22.6 ml) was added dropwise over 3 minutes and the resultant mixture was stirred at ambient temperature for 18 hours. The reaction mixture was evaporated. The residue was treated with hot water (400 ml) and the insoluble material was removed by filtration. The filtrate was acidified to pH5 with acetic acid. The precipitated solid was collected and washed with water. The resultant solid was triturated under hot ethanol. The insoluble material was collected by filtration, washed with ethanol and dried under vacuum. There was thus obtained 6-hydroxy-2-(3-nitrophenyl)pyrimidin-4(3H)-one (9.4 g); NMR Spectrum: (DMSOd$_6$) 5.58 (s, 1H), 7.83 (t, 1H), 8.38-8.42 (m, 1H), 8.58 (d, 1H), 8.99 (s, 1H).

A mixture of 6-hydroxy-2-(3-nitrophenyl)pyrimidin-4 (3H)-one (5 g) and phosphorus oxychloride (100 ml) was stirred and heated to 105° C. under an atmosphere of nitrogen for 3 hours. The resultant reaction mixture was evaporated, toluene (50 ml) was added and the mixture was evaporated again. The residue was dissolved in methylene chloride (200 ml), an excess of solid potassium carbonate was added portionwise until effervescence ceased and the mixture was stirred at ambient temperature for 30 minutes. The mixture was filtered and the filtrate was evaporated. The residue was purified by column chromatography on silica gel using a 1:1 mixture of isohexane and methylene chloride as eluent. There was thus obtained 4,6-dichloro-2-(3-nitrophenyl)pyrimidine (4.38 g) as a white solid; NMR Spectrum: (DMSO-d$_6$) 7.89 (t, 1H), 8.1 (s, 1H), 8.49 (d, 1H), 8.71 (d, 1H), 9.0 (s, 1H).

A mixture of 4,6-dichloro-2-(3-nitrophenyl)pyrimidine (8.1 g), stannous chloride dihydrate (27.1 g) and ethyl acetate (1 liter) was stirred and heated to reflux for 3 hours under an atmosphere of nitrogen. After cooling to ambient temperature, aqueous ammonium hydroxide solution (d=0.88) was added with vigorous stirring to produce a slurry of tin salts. The mixture was filtered and the ethyl acetate layer was decanted. The aqueous layer was washed with ethyl acetate. The organic layers were combined, dried over magnesium sulphate and evaporated. The residue was purified by column chromatography on silica using an increasingly polar solvent gradient from 0% to 100% ethyl acetate in methylene chloride as eluent. There was thus obtained 2-(3-aminophenyl)-4,6-dichloropyrimidine (5.4 g); NMR Spectrum: (DMSOd$_6$) 5.4 (s, 2H), 6.76-6.81 (m, 1H), 7.19 (t, 1H), 7.48 (m, 1H), 7.53 (t, 1H), 7.88 (s, 1H).

2-(7-Azabenzotriazol-1-yl)-1,1,3,3-tetramethyluronium hexafluorophosphate(V) (5.36 g) was added to a mixture of 1-(tert-butoxycarbonyl)piperidine-4-carboxylic acid (3.23 g), diisopropylethylamine (2.4 ml) and DMA (80 ml) and the mixture was stirred at ambient temperature for 1 hour under an atmosphere of nitrogen. 2-(3-Aminophenyl)-4,6-dichloropyrimidine (5 g) was added and the reaction mixture was stirred at ambient temperature for 1 hour. The resultant reaction mixture was stirred and heated to 70° C. for 1 hour. The reaction mixture was evaporated and the residue was purified by column chromatography on silica using an increasingly polar gradient of 0% to 30% ethyl acetate in methylene chloride as eluent. There was thus obtained 2-[3-(1-tert-butoxycarbonylpiperidin-4-ylcarbonylamino)phenyl]-4,6-dichloropyrimidine as a solid (3.6 g); NMR Spectrum: (CDCl$_3$) 1.41 (s, 9H), 1.62-1.77 (m, 2H), 1.81-1.91 (m, 2H), 2.28-2.39 (m, 1H), 2.68-2.8 (m, 2H), 4.14 (d, 2H), 7.19 (s, 2H), 7.22 (s, 1H), 7.26 (s, 1H), 7.38 (t, 1H), 7.94 (d, 1H), 8.12 (d, 1H), 8.21 (t, 1H).

Morpholine (0.65 g) was added to a mixture of 2-[3-(1-tert-butoxycarbonylpiperidin-4-ylcarbonylamino)phenyl]-4,6-dichloropyrimidine (3 g) and triethylamine (1.36 ml) and the resultant mixture was stirred at ambient temperature for 1 hour. The reaction mixture was evaporated and the residue was partitioned between methylene chloride and an aqueous ammonium hydroxide solution (d=0.88). The organic layer was separated, dried over magnesium sulphate and evaporated. The residue was purified by column chromatography on silica using an increasingly polar solvent gradient from 0% to 20% ethyl acetate in methylene chloride as eluent. There was thus obtained 2-[3-(1-tert-butoxycarbonylpiperidin-4-ylcarbonylamino)phenyl]-4-chloro-6-morpholinopyrimidine as an oil (3.8 g); NMR Spectrum: (DMSO-d$_6$) 1.43 (s, 10H), 1.45-1.58 (m, 2H), 1.8 (d, 2H), 2.71-2.84 (m, 2H), 3.68-3.78 (m, 8H), 4.01 (d, 2H), 6.91 (s, 1H), 7.4 (t, 1H), 7.88-7.93 (m, 1H), 7.95-7.99 (m, 1H), 8.44 (t, 1H), 10.07 (s, 1H).

EXAMPLE 2

2-(3-acetamidophenyl)-4-(2-methoxypyrimidin-5-yl)-6-morpholinopyrimidine

A mixture of 2-(3-acetamidophenyl)-4-bromo-6-morpholinopyrimidine (0.037 g), 2-methoxypyrimidin-5-ylboronic acid (0.019 g), tetrakis(triphenylphosphine)palladium (0) (3 mg), a saturated aqueous sodium bicarbonate solution (0.2 ml) and 1,2-dimethoxyethane (2 ml) was stirred and heated to 60° C. for 18 hours under an atmosphere of nitrogen. A second portion of each of 2-methoxypyrimidin-5-ylboronic acid (0.019 g), tetrakis(triphenylphosphine)palladium (0) (2 mg), a saturated aqueous sodium bicarbonate solution (0.2 ml) and 1,2-dimethoxyethane (1 ml) was added and the resultant mixture was heated to 60° C. for a further 18 hours. The resultant reaction mixture was evaporated and the residue was triturated under a 5:1 mixture (1 ml) of methylene chloride and methanol. The soluble material was purified by column chromatography on reversed-phase silica using an 'Isolute SCX' column (1 g; International Sorbent Technology Limited, Mid Glamorgan, UK) by initially washing the column with methanol (5 ml) followed by elution with a 5:3:2 mixture of methanol, methylene chloride and a 7M methanolic ammonia solution. The material so obtained was dried under vacuum. There was thus obtained the title compound as a solid (0.034 g); NMR Spectrum: (DMSOd$_6$) 2.05 (s, 3H), 3.66-3.8 (m, 8H), 3.97 (s, 3H), 7.3-7.37 (m, 2H), 7.82 (d, 1H), 8.03-8.09 (m, 1H), 8.52 (s, 1H), 9.38 (s, 2H), 9.98 (s, 1H); Mass Spectrum: M+H$^+$407.

The 2-(3-acetamidophenyl)-4-bromo-6-morpholinopyrimidine used as a starting material was prepared as follows:—

Phosphorus oxybromide (49.1 g) was added portionwise to a stirred mixture of 6-hydroxy-2-(3-nitrophenyl)pyrimidin-4 (3H)-one (5 g), triethylamine (11.9 ml) and acetonitrile (200 ml) that had been cooled to 5° C. under an atmosphere of nitrogen. The mixture was allowed to warm to ambient temperature and was then heated to 65° C. for 2 hours. After cooling, the mixture was filtered and the filtrate was evaporated. Toluene was added and the filtrate residue was re-evaporated. The resultant residue was suspended in methylene chloride and washed with a 1:1 mixture of aqueous ammonium hydroxide solution (d=0.88) and water. The organic layer was separated, dried over magnesium sulphate and evaporated. The residue was purified by column chromatography on silica using methylene chloride as eluent. There was thus obtained 4,6-dibromo-2-(3-nitrophenyl)pyrimidine (1.45 g); NMR Spectrum: (CDCl$_3$) 7.58-7.66 (m, 2H), 8.32 (d, 1H), 8.70 (d, 1H), 9.22 (s, 1H).

Morpholine (2.0 g) was added dropwise over 5 minutes to a solution of 4,6-dibromo-2-(3-nitrophenyl)pyrimidine (7.5 g) in DMA (75 ml) that had been cooled to 5° C. The mixture was stirred at ambient temperature for 1 hour. Further portions of morpholine (0.6 ml, 0.5 ml and 0.3 ml) were added in turn until all of the starting material had been consumed. The reaction mixture was evaporated and the residue was triturated under a cold aqueous ammonium hydroxide solution. The resultant solid was isolated, washed with water and dried under vacuum. There was thus obtained 4-bromo-6-morpholino-2-(3-nitrophenyl)pyrimidine as a pale yellow solid (8.4 g); NMR Spectrum: (DMSOd$_6$) 3.66-3.81 (m, 8H), 7.15 (s, 1H), 7.79 (t, 1H), 8.37 (d, 1H), 8.69 (d, 1H), 8.99 (s, 1H).

A mixture of 4-bromo-6-morpholino-2-(3-nitrophenyl)pyrimidine (8.2 g), stannous chloride dihydrate (17.7 g) and ethyl acetate (500 ml) was stirred and heated to reflux for 8 hours under an atmosphere of nitrogen. After cooling to ambient temperature, aqueous ammonium hydroxide solution (d=0.88) was added over 5 minutes with vigorous stirring to produce a white slurry of tin residues. The ethyl acetate layer was decanted and the aqueous slurry was washed with ethyl acetate. The organic layers were combined, dried over magnesium sulphate and evaporated. The residue was purified by column chromatography on silica using an increasingly polar solvent gradient from 0% to 20% ethyl acetate in methylene chloride as eluent. There was thus obtained 2-(3-aminophenyl)-4-bromo-6-morpholinopyrimidine (5.49 g); NMR Spectrum: (DMSO-d$_6$) 3.7 (s, 8H), 5.24 (s, 2H), 6.66-6.72 (m, 1H), 6.98 (s, 1H), 7.11 (t, 1H), 7.44 (d, 1H), 7.54 (s, 1H).

Acetic anhydride (30 ml) was added to a stirred solution of 2-(3-aminophenyl)-4-bromo-6-morpholinopyrimidine (2.5 g) in DMA (50 ml) and the resultant mixture was heated to 60° C. under an atmosphere of nitrogen for 1 hour. After cooling, the mixture was evaporated and the residue was dried under vacuum. There was thus obtained 2-(3-acetamidophenyl)-4-bromo-6-morpholinopyrimidine (2.54 g); NMR Spectrum: (DMSOd$_6$) 2.06 (s, 3H), 3.73 (s, 8H), 7.04 (s, 1H), 7.4 (t, 1H), 7.88 (d, 1H), 7.95 (d, 1H), 8.38 (s, 1H), 10.08 (s, 1H).

EXAMPLE 3

4-(2,4-dimethoxypyrimidin-5-yl)-6-morpholino-2-(3-piperidin-4-ylcarbonylaminophenyl)pyrimidine A mixture of 2-[3-(1-tert-butoxycarbonylpiperidin-4-ylcarbonylamino)phenyl]-6-chloro-4-(2,4-dimethoxypyrimidin-5-yl)pyrimidine (0.072 g), morpholine (0.056 g) and acetonitrile (2.5 ml) was stirred under an atmosphere of nitrogen and heated to 100° C. for 5 minutes using microwave radiation. The reaction mixture was evaporated. Toluene was added and the mixture was re-evaporated. Trifluoroacetic acid (3 ml) was added to the material so obtained and the mixture was stirred at ambient temperature for 3 hours. The mixture was evaporated. Toluene was added and the mixture was re-evaporated and the residue was purified by column chromatography on an 'Isolute SCX' column (1 g) by initially washing the column with methylene chloride and then with methanol (5 ml) followed by elution with a 7M methanolic ammonia solution. The material so obtained was dried under vacuum. There was thus obtained the title compound as a solid (0.019 g); NMR Spectrum: (CDCl$_3$) 1.68-1.84 (m, 2H), 1.91-2.0 (m, 2H), 2.37-2.5 (m, 1H), 2.63-2.76 (m, 2H), 3.14-3.27 (m, 2H), 3.74-3.91 (m, 8H), 7.07 (s, 1H), 7.12 (s, 1H), 7.42 (t, 1H), 8.03 (d, 1H), 8.21 (d, 1H), 8.31 (s, 1H), 9.37 (s, 1H); Mass Spectrum: M+H$^+$ 506.

The 2-[3-(1-tert-butoxycarbonylpiperidin-4-ylcarbonylamino)phenyl]-6-chloro-4-(2,4-dimethoxypyrimidin-5-yl)pyrimidine used as a starting material was prepared as follows:—

A mixture of 2-[3-(1-tert-butoxycarbonylpiperidin-4-ylcarbonylamino)phenyl]-4,6-dichloropyrimidine (0.19 g), 2,4-dimethoxypyrimidin-5-ylboronic acid (0.085 g), caesium fluoride (0.064 g), a [1,1'-bis(diphenylphosphino)ferrocene]dichloropalladium(II) 1:1 complex with methylene chloride (0.01 g) and methanol (20 ml) was stirred under an atmosphere of nitrogen and heated to reflux for 18 hours. The resultant reaction mixture was evaporated and the residue was partitioned between methylene chloride and a saturated aqueous sodium bicarbonate solution. The organic solution was washed with brine, dried over magnesium sulphate and evaporated. The residue was purified by column chromatography on silica using a 1:1 mixture of hexane and ethyl acetate as eluent. There was thus obtained 2-[3-(1-tert-butoxycarbonylpiperidin-4-ylcarbonylamino)phenyl]-6-chloro-4-(2,4-dimethoxypyrimidin-5-yl)pyrimidine as a solid (0.067 g); NMR Spectrum: (CDCl$_3$) 1.48 (s, 9H), 1.65-1.85 (m, 2H), 1.89-2.01 (m, 2H), 2.43 (t, 1H), 2.74-2.87 (m, 2H), 4.11 (s, 3H), 4.19 (s, 3H), 7.27 (s, 1H), 7.46 (t, 1H), 7.55 (s, 1H), 7.9 (s, 1H), 8.07 (d, 1H), 8.24 (d, 1H), 8.29-8.32 (m, 1H).

EXAMPLE 4

2-(5-hydroxymethylfuran-2-yl)-6-morpholino-4-(3-piperidin-3-ylcarbonylaminophenyl)pyrimidine Sodium borohydride (0.076 g) was added portionwise to a mixture of 4-[3-(1-tert-butoxycarbonylpiperidin-3-ylcarbonylamino)phenyl]-2-(5-formylfuran-2-yl)-6-morpholinopyrimidine (0.112 g) and ethanol (5 ml) and the reaction mixture was stirred at ambient temperature for 3 hours. The mixture was evaporated to give 4-[3-(1-tert-butoxycarbonylpiperidin-3-ylcarbonylamino)phenyl]-2-(5-hydroxymethylfuran-2-yl)-6-morpholinopyrimidine which was used without further purification. A mixture of the material so obtained, trifluoroacetic acid (1.5 ml) and methylene chloride (2.5 ml) was stirred at ambient temperature for 1 hour and then heated to 40° C. for 10 minutes. The mixture was evaporated and the residue was partitioned between methylene chloride and water. The aqueous layer was separated, basified by the addition of aqueous ammonium hydroxide (d=0.88) and extracted with methylene chloride. The organic extracts were combined, dried over magnesium sulphate and evaporated. The residue was purified by HPLC using a Waters 'Xterra' preparative reversed-phase column (5 microns silica, 19 mm diameter, 100 mm length) using decreasingly polar mixtures of water [containing 1% aqueous ammonium hydroxide (d=0.88)] and acetonitrile as eluent. There was thus obtained the title compound as a solid (4.4 mg); NMR Spectrum: (CD$_3$OD) 1.47-1.58 (m, 1H), 1.64-1.75 (m, 2H), 1.91-1.97 (m, 1H), 2.5-2.65 (m, 2H), 2.82 (m, 1H), 2.9-2.94 (m, 1H), 3.07 (m, 1H), 3.17-3.28 (m, 8H), 4.53 (s, 2H), 6.38 (d, 1H), 6.85 (s, 1H), 7.15 (d, 1H), 7.34 (t, 1H), 7.6 (d, 1H), 7.69 (d, 1H), 8.16 (s, 1H); Mass Spectrum: M+H$^+$ 464.

The 4-[3-(1-tert-butoxycarbonylpiperidin-3-ylcarbonylamino)phenyl]-2-(5-formylfuran-2-yl)-6-morpholinopyrimidine used as a starting material was prepared as follows:—

A mixture of 2,4,6-trichloropyrimidine (3.66 g), 3-nitrophenylboronic acid (3.34 g), tetrakis(triphenylphosphine)palladium(0) (0.02 g), a saturated aqueous solution of sodium carbonate (6.36 g) and 1,2-dimethoxyethane (60 ml) was stirred and heated to 90° C. for 30 minutes and to 85° C. for 16 hours under an atmosphere of nitrogen. The resultant reaction mixture was allowed to cool to ambient temperature. The precipitate was isolated by filtration and washed with methylene chloride (20 ml). There was thus obtained 2,6-dichloro-4-(3-nitrophenyl)pyrimidine (1.1 g), which was used without further characterisation.

A mixture of 2,6-dichloro-4-(3-nitrophenyl)pyrimidine (1.1 g), morpholine (0.177 g) and DMA (5 ml) was stirred at ambient temperature for 2 hours. The solvent was evaporated and the residue was re-suspended in methylene chloride. The resultant solid was collected by filtration and washed with a small amount of methylene chloride. There was thus obtained 2-chloro-6-morpholino-4-(3-nitrophenyl)pyrimidine (0.262 g) which was used without further purification. A sample (0.02 g) of the material was purified by column chromatography on silica using an increasingly polar solvent gradient from 0% to 3% ethyl acetate in methylene chloride as eluent to give purified 2-chloro-6-morpholino-4-(3-nitrophenyl)pyrimidine as a solid (0.014 g); NMR Spectrum: (DMSOd$_6$) 3.74 (d, 8H), 7.55 (s, 1H), 7.83 (t, 1H), 8.37 (d, 1H), 8.60 (d, 1H), 8.92 (t, 1H).

The previous reaction steps were repeated to obtain further amounts of 2-chloro-6-morpholino-4-(3-nitrophenyl)pyrimidine. Stannous chloride dihydrate (12 g) was added to a stirred suspension of 2-chloro-6-morpholino-4-(3-nitrophenyl)pyrimidine (4.27 g) in ethyl acetate (220 ml) and the resultant mixture was stirred and heated to 60° C. for 3.5 hours. The reaction mixture was allowed to cool and aqueous ammonium hydroxide (d=0.88; 60 ml) was added. The mixture was stirred vigorously for 30 minutes after which the ethyl acetate layer was decanted off. The organic solvent was evaporated and the residue was purified by column chromatography on silica using an increasingly polar gradient of 0% to 30% ethyl acetate in methylene chloride as eluent. There was thus obtained 4-(3-aminophenyl)-2-chloro-6-morpholinopyrimidine as a solid (1.29 g); NMR Spectrum: (DMSO-d$_6$) 3.69 (s, 8H), 5.26 (s, 2H), 6.7 (m, 1H), 7.13 (t, 1H), 7.16 (s, 1H), 7.24 (m, 1H), 7.34 (t, 1H); Mass Spectrum: M+H$^+$ 291.

Diisopropylethylamine (1.07 g) was added to a stirred solution of N-(tert-butoxycarbonyl)piperidine-3-carboxylic acid (1.23 g), 2-(7-azabenzotriazol-1-yl)-1,1,3,3-tetramethyluronium hexafluorophosphate (2.04 g) and DMA (20 ml) and the mixture was stirred at ambient temperature for 5 minutes. 4-(3-Aminophenyl)-2-chloro-6-morpholinopyrimidine (1.2 g) was added and the reaction mixture was stirred at ambient temperature for 2 hours. The solution was evaporated and the residue was adsorbed onto reversed-phase silica using an 'Isolute SCX-3' column (50 g) and allowed to stand for 5 minutes. The column was eluted initially with a 10:1 mixture of methylene chloride and methanol. There was thus obtained 4-{3-[N-(tert-butoxycarbonyl)piperidin-3-ylcarbonylamino]phenyl}-2-chloro-6-morpholinopyrimidine (0.52 g); NMR Spectrum: (CDCl$_3$) 1.41 (s, 9H), 1.43-1.51 (m, 2H), 1.81-1.9 (m, 1H), 1.99-2.06 (m, 1H), 2.41-2.49 (m, 1H), 3.11-3.26 (m, 1H), 3.43-3.84 (m, 11H), 6.7 (s, 1H), 7.19 (s, 1H), 7.33 (t, 1H), 7.62-7.68 (m, 2H), 8.11 (s, 1H). The column was subsequently eluted with a 7M methanolic ammonia solution. There was thus obtained 2-chloro-6-morpholino-4-(3-piperidin-3-ylcarbonylaminophenyl)pyrimidine as a solid (0.52 g); NMR Spectrum: (CDCl$_3$) 1.69-1.82 (m, 3H), 3.06-3.17 (m, 2H), 3.25-3.31 (m, 1H), 3.62-3.82 (m, 11H), 6.75 (s, 1H), 7.36 (t, 1H), 7.64 (d, 1H), 7.74 (d, 1H), 8.15 (s, 1H), 10.04 (s, 1H).

A mixture 4-{3-[N-(tert-butoxycarbonyl)piperidin-3-yl-carbonylamino]phenyl}-2-chloro-6-morpholinopyrimidine (0.5 g), 5-formylfuran-2-ylboronic acid (0.28 g), caesium fluoride (0.304 g), [1,1'-bis(diphenylphosphino)ferrocene]dichloropalladium(II) 1:1 complex with methylene chloride (0.041 g), and methanol (5 ml) was placed in a sealed glass tube under an atmosphere of nitrogen and heated to 120° C. for 15 minutes. The reaction mixture was allowed to cool to ambient temperature. The mixture was evaporated and the residue was purified by chromatography on silica using increasingly polar mixtures of methylene chloride and methanol as eluent. There was thus obtained 4-[3-(1-tert-butoxycarbonylpiperidin-3-ylcarbonylamino)phenyl]-2-(5-formylfuran-2-yl)-6-morpholinopyrimidine which was used without further characterisation.

EXAMPLE 5

4-(5-hydroxymethylfuran-2-yl)-6-morpholino-2-(3-piperidin-4-ylcarbonylaminophenyl)pyrimidine Using analogous procedures to those described in Example 4, 2-[3-(1-tert-butoxycarbonylpiperidin-4-ylcarbonylamino)phenyl]-4-(5-formylfuran-2-yl)-6-morpholinopyrimidine was converted into the title compound in 26% yield; NMR Spectrum: (DMSO-$d_6$ & $CD_3CO_2D$) 1.95-2.06 (m, 2H), 2.61-2.75 (m, 1H), 2.88-3.0 (m, 2H), 3.37 (d, 2H), 3.75 (s, 8H), 4.51 (s, 2H), 6.51 (d, 1H), 6.92 (s, 1H), 7.25 (d, 1H), 7.4 (t, 1H), 7.87-7.92 (m, 1H), 8.08-8.13 (m, 1H), 8.49-8.51 (m, 1; Mass Spectrum: M+H$^+$ 464.

The 2-[3-(1-tert-butoxycarbonylpiperidin-4-ylcarbonylamino)phenyl]-4-(5-formylfuran-2-yl)-6-morpholinopyrimidine used as a starting material was prepared as follows:—

Using analogous procedures to those described in the last paragraph of the portion of Example 4 that is concerned with the preparation of starting materials, 2-{3-[N-(tert-butoxycarbonyl)piperidin-4-ylcarbonylamino]phenyl}-4-chloro-6-morpholinopyrimidine was reacted with 5-formylfuran-2-ylboronic acid. There was thus obtained 2-[3-(1-tert-butoxycarbonylpiperidin-4-ylcarbonylamino)phenyl]-4-(5-formylfuran-2-yl)-6-morpholinopyrimidine as an oil that was used without further characterisation.

EXAMPLE 6

2-(1H-benzimidazol-4-yl)-6-morpholino-4-(3-piperidin-3-ylcarbonylaminophenyl)pyrimidine A mixture 4-{3-[N-(tert-butoxycarbonyl)piperidin-3-yl-carbonylamino]phenyl}-2-chloro-6-morpholinopyrimidine (0.15 g), 3-(4,4,5,5-tetramethyl-1,3,2-dioxaborolan-2-yl)benzene-1,2-diamine (0.072 g), tetrakis(triphenylphosphine)palladium(0) (6 mg), a saturated aqueous solution of sodium carbonate (0.127 g) and 1,4-dioxane (18 ml) was placed in a sealed glass tube under an atmosphere of nitrogen and heated to 140° C. using microwave radiation for 10 minutes. The reaction mixture was allowed to cool to ambient temperature. The mixture was evaporated and the residue was suspended in a 10:1 mixture of methylene chloride and methanol. The supernatant solution was decanted from inorganic material and evaporated. The resultant residue was purified by column chromatography on silica using an increasingly polar gradient of 0% to 5% methanol in methylene chloride as eluent. There was thus obtained 2-(2,3-diaminophenyl)-4-{3-[N-(tert-butoxycarbonyl)piperidin-3-ylcarbonylamino]phenyl}-6-morpholinopyrimidine as a gum (0.171 g); Mass Spectrum: M+H$^+$ 574.

A mixture of a portion (0.143 g) of the material so obtained, triethyl orthoformate (0.7 ml) and 4-toluenesulphonic acid (0.005 g) was stirred and heated to 80° C. for 45 minutes. The reaction mixture was cooled to ambient temperature. Trifluoroacetic acid (5 ml) was added and the reaction mixture was stirred at ambient temperature for 30 minutes. The mixture was evaporated. Toluene was added to the residue and this mixture was evaporated. The residue was purified by column chromatography on silica using initially a 10:1 mixture of methylene chloride and methanol and subsequently an increasingly polar gradient of 1% to 10% methanolic ammonia (7M) in methylene chloride. There was thus obtained the title compound as a foam (0.077 g); NMR Spectrum: (DMSO-$d_6$) 1.42-1.56 (m, 1H), 1.63-1.74 (m, 2H), 1.93-2.02 (m, 1H), 2.55-2.65 (m, 2H), 2.8 (t, 1H), 2.92-2.99 (m, 1H), 3.12-3.19 (m, 1H), 3.75-3.88 (m, 8H), 7.25 (s, 1H), 7.37 (t, 1H), 7.49 (t, 1H), 7.72 (d, 1H), 7.86 (d, 1H), 7.92 (d, 1H), 8.32-8.38 (m, 2H), 8.7 (s, 1H), 10.24 (s, 1H), 11.88 (s, 1H); Mass Spectrum: M+H$^+$ 484.

The 3-(4,4,5,5-tetramethyl-1,3,2-dioxaborolan-2-yl)benzene-1,2-diamine used as a starting material was prepared as follows:—

A mixture of 3-acetamido-2-nitrophenylboronic acid (*Bioconjugate Chem.* 1991, 2, 317-322; 1.55 g) and 2N aqueous hydrochloric acid (20 ml) was stirred and heated to 90° C. for 15 minutes. The reaction mixture was evaporated. The residue was suspended in 1,4-dioxane and evaporated again. The resultant residue was suspended in 1,4-dioxane and pinacol (1.58 g) was added. The reaction mixture was stirred and heated to 80° C. for 20 minutes. The mixture was evaporated. There was thus obtained 2-nitro-3-(4,4,5,5-tetramethyl-1,3,2-dioxaborolan-2-yl)aniline; NMR Spectrum: (DMSOd$_6$) 1.3 (s, 12H), 6.54 (d, 1H), 7.01 (d, 1H), 7.35-7.39 (m, 1H), 7.47 (s, 2H).

A solution of a portion (1.4 g) of the material so obtained, 10% palladium on charcoal catalyst (0.5 g) and glacial acetic acid (10 ml) was stirred under an atmosphere pressure of hydrogen and heated to 40° C. for 1 hour. The reaction mixture was filtered and the filtrate was evaporated. The residue was purified by column chromatography on silica using an increasingly polar gradient of 0% to 10% methanol in methylene chloride as eluent. There was thus obtained 3-(4,4,5,5-tetramethyl-1,3,2-dioxaborolan-2-yl)benzene-1,2-diamine as a solid (0.42 g); NMR Spectrum: 1.31 (s, 12H), 6.37 (t, 1H), 6.63 (d, 1H), 6.79 (d, 1H).

The invention claimed is:
1. A pyrimidine derivative of the Formula I

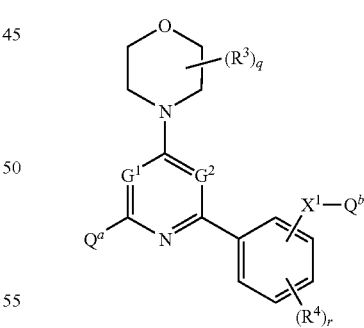

I wherein:—
Q$^a$ is a heteroaryl group that optionally bears 1, 2, 3 or 4 substituents, which may be the same or different, selected from halogeno, trifluoromethyl, cyano, isocyano, nitro, hydroxy, mercapto, amino, formyl, carboxy, carbamoyl, ureido, (1-8C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N'-(1-6C)alkylureido, N',N''-di-[(1-6C)alkyl]ureido, N-(1-6C)alkylureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$$Q^2\text{-}X^2-$$

wherein $X^2$ is a direct bond or is selected from O, S, SO, $SO_2$, $N(R^5)$, CO, $CH(OR^5)$, $CON(R^5)$, $N(R^5)CO$, $N(R^5)CON(R^5)$, $SO_2N(R^5)$, $N(R^5)SO_2$, $OC(R^5)_2$, $SC(R^5)_2$ and $N(R^5)C(R^5)_2$, wherein $R^5$ is hydrogen or (1-8C)alkyl, and $Q^2$ is aryl, aryl-(1-6C)alkyl, (3-8C)cycloalkyl, (3-8C)cycloalkyl-(1-6C)alkyl, (3-8C)cycloalkenyl, (3-8C)cycloalkenyl-(1-6C)alkyl, heteroaryl, heteroaryl-(1-6C)alkyl, heterocyclyl or heterocyclyl-(1-6C)alkyl, or $Q^a$ bears a (1-3C)alkylenedioxy substituent, and wherein any CH, $CH_2$ or $CH_3$ group within a substituent on $Q^a$ optionally bears on each said CH, $CH_2$ or $CH_3$ group one or more halogeno or (1-8C)alkyl substituents and/or a substituent selected from hydroxy, mercapto, amino, cyano, carboxy, carbamoyl, ureido, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylureido, N'-(1-6C)alkylureido, N',N'-di-[(1-6C)alkyl]ureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$$-X^3\text{-}Q^3$$

wherein $X^3$ is a direct bond or is selected from O, S, SO, $SO_2$, $N(R^6)$, CO, $CH(OR^6)$, $CON(R^6)$, $N(R^6)CO$, $N(R^6)CON(R^6)$, $SO_2N(R^6)$, $N(R^6)SO_2$, $C(R^6)_2O$, $C(R^6)_2S$ and $C(R^6)_2N(R^6)$, wherein $R^6$ is hydrogen or (1-8C)alkyl, and $Q^3$ is aryl, aryl-(1-6C)alkyl, (3-8C)cycloalkyl, (3-8C)cycloalkyl-(1-6C)alkyl, (3-8C)cycloalkenyl, (3-8C)cycloalkenyl-(1-6C)alkyl, heteroaryl, heteroaryl-(1-6C)alkyl, heterocyclyl or heterocyclyl-(4-6C)alkyl, and wherein any aryl, (3-8C)cycloalkyl, (3-8C)cycloalkenyl, heteroaryl or heterocyclyl group within a substituent on $Q^a$ optionally bears 1, 2 or 3 substituents, which may be the same or different, selected from halogeno, trifluoromethyl, cyano, nitro, hydroxy, amino, carboxy, carbamoyl, ureido, (1-8C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (2-6C)alkanoylamino, N-(1-6C)alkyl-(2-6C)alkanoylamino, N-(1-6C)alkylureido, N'-(1-6C)alkylureido, N',N'-di-[(1-6C)alkyl]ureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$$-X^4-R^7$$

wherein $X^4$ is a direct bond or is selected from O and $N(R^8)$, wherein $R^8$ is hydrogen or (1-8C)alkyl, and $R^7$ is halogeno-(1-6C)alkyl, hydroxy-(1-6C)alkyl, mercapto-(1-6C)alkyl, (1-6C)alkylthio-(1-6C)alkyl, (1-6C)alkoxy-(1-6C)alkyl, (1-6C)alkylthio-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, (1-6C)alkoxycarbonylamino-(1-6C)alkyl, N-(1-6C)alkylureido-(1-6C)alkyl, N'-(1-6C)alkylureido-(1-6C)alkyl, N',N'-di-[(1-6C)alkyl]ureido-(1-6C)alkyl, N'-di-[(1-6C)alkyl]ureido-(1-6C)alkyl or N,N',N'-tri-[(1-6C)alkyl]ureido-(1-6C)alkyl, or from a group of the formula:

$$-X^5\text{-}Q^4$$

wherein $X^5$ is a direct bond or is selected from O, CO and $N(R^9)$, wherein $R^9$ is hydrogen or (1-8C)alkyl, and $Q^4$ is aryl, aryl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, hydroxy, (1-8C)alkyl and (1-6C)alkoxy, and wherein any heterocyclyl group within a substituent on $Q^a$ optionally bears 1 or 2 oxo or thioxo substituents, and wherein adjacent carbon atoms in any (2-6C)alkylene chain within a substituent on $Q^a$ are optionally separated by the insertion into the chain of a group selected from O, S, SO, $SO_2$, $N(R^{10})$, CO, $CH(OR^{10})$, $CON(R^{10})$, $N(R^{10})CO$, $N(R^{10})CON(R^{10})$, $SO_2N(R^{10})$, $N(R^{10})SO_2$, CH=CH and C≡C wherein $R^{10}$ is hydrogen or (1-8C)alkyl;

$G^1$ is N or $C(R^1)$ wherein $R^1$ is hydrogen or (1-8C)alkyl, and $G^2$ is N or $C(R^2)$ wherein $R^2$ is hydrogen or (1-8C)alkyl, provided that one of $G^1$ and $G^2$ is N, and if $G^1$ is N then $G^2$ is $C(R^2)$, or if $G^2$ is N then $G^1$ is $C(R^1)$;

q is 0, 1, 2, 3 or 4;

each $R^3$ group, which may be the same or different, is (1-8C)alkyl or a group of the formula:

$$-X^6-R^{11}$$

wherein $X^6$ is a direct bond or is selected from O and $N(R^{12})$, wherein $R^{12}$ is hydrogen or (1-8C)alkyl, and $R^{11}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl or (2-6C)alkanoylamino-(1-6C)alkyl;

r is 0, 1 or 2;

each $R^4$ group, which may be the same or different, is selected from halogeno, trifluoromethyl, cyano, nitro, hydroxy, mercapto, amino, carboxy, carbamoyl, ureido, (1-8C)alkyl, (2-8C)alkenyl, (2-8C)alkynyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N'-(1-6C)alkylureido, N',N'-di-[(1-6C)alkyl]ureido, N-(1-6C)alkylureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino;

$X^1$ is selected from CO, $N(R^{13})CO$, $CON(R^{13})$, $N(R^{13})CON(R^{13})$, $N(R^{13})COC(R^{13})_2O$, $N(R^{13})COC(R^{13})_2S$, $N(R^{13})COC(R^{13})_2N(R^{13})$ and $N(R^{13})COC(R^{13})_2N(R^{13})CO$, wherein $R^{13}$ is hydrogen or (1-8C)alkyl; and $Q^b$ is (1-8C)alkyl, (2-8C)alkenyl, (2-8C)alkynyl, halogeno-(1-6C)alkyl, hydroxy-(1-6C)alkyl, mercapto-(1-

6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (1-6C)alkylthio-(1-6C)alkyl, (1-6C)alkylsulphinyl-(1-6C)alkyl, (1-6C)alkylsulphonyl-(1-6C)alkyl, (2-6C)alkanoylamino-(1-6C)alkyl, N-(1-6C)alkyl-(2-6C)alkanoylamino-(1-6C)alkyl, (1-6C)alkoxycarbonylamino-(1-6C)alkyl, N-(1-6C)alkylureido-(1-6C)alkyl, N'-(1-6C)alkylureido-(1-6C)alkyl, N',N'-di-[(1-6C)alkyl]ureido-(1-6C)alkyl, N,N'-di-[(1-6C)alkyl]ureido-(1-6C)alkyl, N,N',N'-tri-[(1-6C)alkyl]ureido-(1-6C)alkyl, (1-6C)alkanesulphonylamino-(1-6C)alkyl or N-(1-6C)alkyl-(1-6C)alkanesulphonylamino-(1-6C)alkyl, or $Q^b$ is aryl, aryl-(1-6C)alkyl, (3-8C)cycloalkyl, (3-8C)cycloalkyl-(1-6C)alkyl, (3-8C)cycloalkenyl, (3-8C)cycloalkenyl-(1-6C)alkyl, heteroaryl, heteroaryl-(1-6C)alkyl, heterocyclyl or heterocyclyl-(1-6C)alkyl, and wherein any CH, $CH_2$ or $CH_3$ group within the $Q^b$ group optionally bears on each said CH, $CH_2$ or $CH_3$ group one or more halogeno or (1-8C)alkyl substituents and/or a substituent selected from hydroxy, mercapto, amino, cyano, carboxy, carbamoyl, ureido, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N'-(1-6C)alkylureido, N',N'-di-[(1-6C)alkyl]ureido, N-(1-6C)alkylureido, N,N'-di-[(1-6C)alkyl]ureido, N,N',N'-tri-[(1-6C)alkyl]ureido, N-(1-6C)alkylsulphamoyl, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, and wherein any aryl, (3-8C)cycloalkyl, (3-8C)cycloalkenyl, heteroaryl or heterocyclyl group within the $Q^b$ group optionally bears 1, 2 or 3 substituents, which may be the same or different, selected from halogeno, trifluoromethyl, cyano, nitro, hydroxy, amino, carboxy, carbamoyl, ureido, (1-8C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (2-6C)alkanoylamino, N-(1-6C)alkyl-(2-6C)alkanoylamino, N'-(1-6C)alkylureido, N',N'-di-[(1-6C)alkyl]ureido, N-(1-6C)alkylureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—$X^7$—$R^{14}$ wherein $X^7$ is a direct bond or is selected from O and $N(R^{15})$, wherein $R^{15}$ is hydrogen or (1-8C)alkyl, and $R^{14}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl, or from a group of the formula:

—$X^8$-$Q^5$ wherein $X^8$ is a direct bond or is selected from O, CO and $N(R^{17})$, wherein $R^{17}$ is hydrogen or (1-8C)alkyl, and $Q^5$ is aryl, aryl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, hydroxy, (1-8C)alkyl and (1-6C)alkoxy, and wherein any heterocyclyl group within the $Q^b$ group optionally bears 1 or 2 oxo or thioxo substituents, and wherein adjacent carbon atoms in any (2-6C)alkylene chain within the $Q^b$ group are optionally separated by the insertion into the chain of a group selected from O, S, SO, $SO_2$, $N(R^{16})$, $N(R^{16})CO$, $CON(R^{16})$, $N(R^{16})CON(R^{16})$, CO, $CH(OR^{16})$, $N(R^{16})SO_2$, $SO_2N(R^{16})$, CH=CH and C≡C wherein $R^{16}$ is hydrogen or (1-8C)alkyl;

or a pharmaceutically-acceptable salt thereof.

2. The pyrimidine derivative of the Formula I according to claim 1 wherein:—

$Q^a$ is furyl, pyrrolyl, thienyl, oxazolyl, isoxazolyl, imidazolyl, pyrazolyl, thiazolyl, isothiazolyl, oxadiazolyl, thiadiazolyl, triazolyl, pyridyl, pyridazinyl, pyrimidinyl, pyrazinyl, benzimidazolyl, benzoxazolyl or benzothiazolyl, and $Q^a$ bears 1 or 2 substituents comprising a first substituent selected from hydroxy, carbamoyl, methoxy, ethoxy, acetamido, propionamido, N-methylacetamido, N-methylpropionamido, hydroxymethyl, 1-hydroxyethyl and 1-hydroxy-1-methylethyl, and an optional second substituent selected from fluoro, chloro, trifluoromethyl, cyano, hydroxy, methyl, ethyl, methoxy and ethoxy;

$G^1$ is CH and $G^2$ is N, or $G^1$ is N and $G^2$ is CH;

q is 0 or q is 1 and the $R^3$ group is methyl;

r is 0 or r is 1 and the $R^4$ group is selected from fluoro, chloro, trifluoromethyl, hydroxy, amino, methyl, methoxy, methylamino and dimethylamino;

the $X^1$-$Q^b$ group is located at the 3- or 4-position;

$X^1$ is selected from CO, NHCO, N(Me)CO, CONH, CON(Me), NHCONH, $NHCOCH_2O$, $NHCOCH_2NH$ and $NHCOCH_2NHCO$; and $Q^b$ is methyl, ethyl, propyl, isopropyl, butyl, pentyl, allyl, 2-methoxyethyl, 3-methoxypropyl, 2-ethoxyethyl, 3-ethoxypropyl, cyanomethyl, 2-cyanoethyl, 3-cyanopropyl, 1-cyano-1-methylethyl, 4-cyanobutyl, 5-cyanopentyl, aminomethyl, 2-aminoethyl, 3-aminopropyl, 4-aminobutyl, 5-aminopentyl, methylaminomethyl, 2-methylaminoethyl, 3-methylaminopropyl, 4-methylaminobutyl, 5-methylaminopentyl, ethylaminomethyl, 2-ethylaminoethyl, 3-ethylaminopropyl, 4-ethylaminobutyl, 5-ethylaminopentyl, dimethylaminomethyl, 2-dimethylaminoethyl, 3-dimethylaminopropyl, 4-dimethylaminobutyl, 5-dimethylaminopentyl, diethylaminomethyl, 2-diethylaminoethyl, 3-diethylaminopropyl, 4-diethylaminobutyl, 5-diethylaminopentyl, 2-methylsulphonylethyl or acetamidomethyl, or $Q^b$ is phenyl, benzyl, 2-phenylethyl, cyclopropyl, cyclobutyl, cyclopentyl, cyclohexyl, cyclopropylmethyl, cyclobutylmethyl, cyclopentylmethyl, cyclohexylmethyl, furyl, thienyl, oxazolyl, isoxazolyl, imidazolyl, pyrazolyl, thiazolyl, triazolyl, oxadiazolyl, thiadiazolyl, tetrazolyl, pyridyl, pyrazinyl, pyridazinyl, pyrimidinyl, furylmethyl, thienylmethyl, oxazolylmethyl, isoxazolylmethyl, imidazolylmethyl, 2-imidazolylethyl, pyrazolylmethyl, thiazolylmethyl, triazolylmethyl, oxadiazolylmethyl, thiadiazolylmethyl, tetrazolylmethyl, pyridylmethyl, 2-pyridylethyl, pyrazinylmethyl, 2-pyrazinylethyl, pyridazinylmethyl, 2-pyridazinylethyl, pyrimidinylmethyl, 2-pyrimidinylethyl, tetrahydrofuranyl, tetrahydropyranyl, tetrahydrothiopyranyl, azetidinyl, pyrrolinyl, pyrrolidinyl, morpholinyl, tetrahydro-1,4-thiazinyl, piperidinyl, homopiperidinyl, piperazinyl, homopiperazinyl, indolinyl, isoindolinyl, tetrahydrofuranylmethyl, tetrahydropyranylmethyl, 1,3-dioxolanylmethyl, 1,4-dioxanylmethyl, pyrrolidinylmethyl, morpholinylmethyl, 2-(morpholinyl)ethyl, piperidinylmethyl, 2-(piperidinyl)ethyl, homopiperidinylmethyl, piperazinylmethyl, 2-(piperazinyl)ethyl or homopiperazinylmethyl, and wherein any CH, $CH_2$ or $CH_3$ group within the $Q^b$ group optionally bears on each said CH, $CH_2$ or $CH_3$ group a substituent selected from hydroxy, amino, cyano, carbamoyl, methoxy, ethoxy, methylsulphonyl, methylamino, dimethylamino, methoxycarbonyl, ethoxycarbonyl, N-methylcarbamoyl, N-ethylcarbamoyl, N-isopropylcarbamoyl, N,N-dimethylcarbamoyl, acetyl, propionyl, pivaloyl, acetamido and N-methylacetamido, and wherein any aryl, (3-8C)cycloalkyl, heteroaryl or heterocyclyl group within the $Q^b$ group optionally bears 1 or 2 substituents, which may be the same or different, selected from fluoro, chloro, trifluoromethyl, hydroxy, amino, carbamoyl, methyl, methoxy, methylamino and dimethylamino and any such aryl, (3-8C)cycloalkyl, heteroaryl or heterocyclyl group within the $Q^b$ group optionally bears a substituent selected from hydroxymethyl, methoxymethyl, cyanomethyl, aminomethyl, methylaminomethyl, dimethylaminomethyl, pyrrolidinylmethyl, morpholinylmethyl, piperidinylmethyl and piperazinylmethyl;

or a pharmaceutically-acceptable salt thereof.

3. The pyrimidine derivative of the Formula I according to claim 1 wherein:—

$Q^a$ is furyl, pyrrolyl, thienyl, oxazolyl, isoxazolyl, imidazolyl, pyrazolyl, thiazolyl, isothiazolyl, oxadiazolyl, thiadiazolyl, triazolyl, pyridyl, pyridazinyl, pyrimidinyl or pyrazinyl, and $Q^a$ bears 1 or 2 substituents comprising a first substituent selected from hydroxy, carbamoyl, methoxy, ethoxy, acetamido, propionamido, N-methylacetamido, N-methylpropionamido, hydroxymethyl, 1-hydroxyethyl and 1-hydroxy-1-methylethyl, and an optional second substituent selected from fluoro, chloro, trifluoromethyl, cyano, hydroxy, methyl, ethyl, methoxy and ethoxy;

$G^1$ is CH and $G^2$ is N, or $G^1$ is N and $G^2$ is CH;

q is 0 or q is 1 and the $R^3$ group is methyl;

r is 0 or r is 1 and the $R^4$ group is selected from fluoro, chloro, trifluoromethyl, hydroxy, amino, methyl, methoxy, methylamino and dimethylamino;

the $X^1$-$Q^b$ group is located at the 3-position;

$X^1$ is selected from NHCO, NHCONH, $NHCOCH_2O$, $NHCOCH_2NH$ and $NHCOCH_2NHCO$; and $Q^b$ is methyl, ethyl, propyl, butyl, pentyl, aminomethyl, 2-aminoethyl, 2-amino-2-methylpropyl, 3-aminopropyl, 4-aminobutyl, 5-aminopentyl, methylaminomethyl, 2-methylaminoethyl, 3-methylaminopropyl, 4-methylaminobutyl, 5-methylaminopentyl, dimethylaminomethyl, 2-dimethylaminoethyl, 3-dimethylaminopropyl, 4-dimethylaminobutyl or 5-dimethylaminopentyl, or $Q^b$ is phenyl, benzyl, 2-phenylethyl, cyclopentyl, cyclohexyl, cyclopentylmethyl, cyclohexylmethyl, thienyl, imidazolyl, thiazolyl, thiadiazolyl, thienylmethyl, imidazolylmethyl, thiazolylmethyl, thiadiazolylmethyl, tetrahydrofuranyl, tetrahydropyranyl, tetrahydrothiopyranyl, pyrrolinyl, pyrrolidinyl, morpholinyl, tetrahydro-1,4-thiazinyl, piperidinyl, homopiperidinyl, piperazinyl, homopiperazinyl, indolionyl, isoindolinyl, pyrrolidinylmethyl, morpholinylmethyl, 2-(morpholinyl)ethyl, piperidinylmethyl, 2-(piperidinyl)ethyl, piperidinyloxymethyl, homopiperidinylmethyl, piperazinylmethyl, 2-(piperazinyl)ethyl, homopiperazinylmethyl or 2-azabicyclo[2.2.1]heptylmethyl, and wherein any aryl, (3-8C)cycloalkyl, heteroaryl or heterocyclyl group within the $Q^b$ group optionally bears a substituent selected from fluoro, chloro, trifluoromethyl, hydroxy, amino, methyl, methoxy, methylamino and dimethylamine and any such aryl, (3-8C)cycloalkyl, heteroaryl or heterocyclyl group within the $Q^b$ group optionally bears a further substituent selected from aminomethyl, methylaminomethyl and dimethylaminomethyl;

or a pharmaceutically-acceptable salt thereof.

4. The pyrimidine derivative of the Formula I according to claim 1 wherein:—

$Q^a$ is furyl, thienyl, oxazolyl, isoxazolyl, imidazolyl, pyrazolyl, thiazolyl, isothiazolyl, pyridyl, pyridazinyl, pyrimidinyl or pyrazinyl, and $Q^a$ bears 1 or 2 substituents comprising a first substituent selected from hydroxy, carbamoyl, methoxy, acetamido, N-methylacetamido, hydroxymethyl, 1-hydroxyethyl and 1-hydroxy-1-methylethyl, and an optional second substituent selected from fluoro, chloro, trifluoromethyl, cyano, hydroxy, methyl and methoxy;

$G^1$ is CH and $G^2$ is N, or $G^1$ is N and $G^2$ is CH;

q is 0;

r is 0;

the $X^1$-$Q^b$ group is located at the 3-position;

$X^1$ is NHCO; and $Q^b$ is methyl, aminomethyl, 2-aminopropyl, 2-amino-2-methylpropyl, 3-aminopropyl, methylaminomethyl or dimethylaminomethyl, or $Q^b$ is phenyl, benzyl, 2-phenylethyl, cyclopentyl, cyclohexyl, cyclohexylmethyl, thiazol-5-yl, thien-3-ylmethyl, imidazol-1-ylmethyl, 1,2,4-thiadiazol-3-ylmethyl, tetrahydropyran-4-yl, tetrahydrothiopyran-4-yl, 3-pyrrolin-2-yl, pyrrolidin-2-yl, pyrrolidin-3-yl, morpholin-2-yl, piperidin-2-yl, piperidin-3-yl, piperidin-4-yl, piperazin-1-yl, isoindolin-1-yl, pyrrolidin-2-ylmethyl, piperidin-4-ylmethyl, 2-(piperidin-4-yl)ethyl, piperidin-4-yloxymethyl, piperazin-1-ylmethyl or 2-azabicyclo[2.2.1]hept-2-ylmethyl, and wherein any aryl, (3-8C)cycloalkyl, heteroaryl or heterocyclyl group within the $Q^b$ group optionally bears a substituent selected from amino, methyl, methylamino and aminomethyl;

or a pharmaceutically-acceptable salt thereof.

5. The pyrimidine derivative of the Formula I according to claim 1 wherein:—

$Q^a$ is furyl, thienyl, oxazolyl, isoxazolyl, imidazolyl, pyrazolyl, thiazolyl, isothiazolyl, pyridyl, pyridazinyl, pyrimidinyl, pyrazinyl, benzimidazolyl, benzoxazolyl or benzothiazolyl, and $Q^a$ bears 1 or 2 substituents comprising a first substituent selected from hydroxy, carbamoyl, methoxy, acetamido, N-methylacetamido, hydroxymethyl, 1-hydroxyethyl and 1-hydroxy-1-methylethyl, and an optional second substituent selected from fluoro, chloro, trifluoromethyl, cyano, hydroxy, methyl and methoxy;

$G^1$ is CH and $G^2$ is N, or $G^1$ is N and $G^2$ is CH;

q is 0;

r is 0 or r is 1 and the $R^4$ group is selected from fluoro, chloro and methyl;

the $X^1$-$Q^b$ group is located at the 3- or 4-position;

$X^1$ is NHCO, N(Me)CO, CONH or CON(Me); and $Q^b$ is methyl, ethyl, propyl, isopropyl, 2-ethoxyethyl, 3-ethoxypropyl, cyanomethyl, 2-cyanoethyl, aminomethyl, 2-aminoethyl, methylaminomethyl, 2-methylaminoethyl, ethylaminomethyl, 2-ethylaminoethyl, dimethylaminomethyl, 2-dimethylaminoethyl, 4-dimethylaminobutyl, 2-methylsulphonylethyl or acetamidomethyl, or $Q^b$ is phenyl, benzyl, cyclopropyl, cyclobutyl, cyclopentyl, cyclohexyl, cyclopropylmethyl, cyclobutylmethyl, cyclopentylmethyl, cyclohexylmethyl, oxazol-5-yl, isoxazol-3-yl, isoxazol-4-yl, imidazol-2-yl, imidazol-4-yl, pyrazol-3-yl, thiazol-5-yl, 1,2,3-triazol-5-yl, tetrazol-5-yl, pyridin-2-yl, pyridin-3-yl, pyridin-4-yl, pyrazin-2-yl, pyridazin-4-yl, pyrimidin-2-yl, pyrimidin-4-yl, thien-3-ylmethyl, oxazol-4-ylmethyl, isoxazol-3-ylmethyl, isoxazol-4-ylmethyl, imidazol-1-ylmethyl, imidazol-2-ylmethyl, 2-imidazol-1-ylethyl, 2-imidazol-2-ylethyl, 2-imidazol-4-ylethyl, pyrazol-1-ylmethyl, pyrazol-3-ylmethyl, 1,2,3-triazol-1-ylmethyl, 1,2,3-triazol-4-ylmethyl, 1,2,4-oxadiazol-3-ylmethyl, 1,2,3-thiadiazol-3-ylmethyl, tetrazol-1-ylmethyl, tetrazol-5-ylmethyl, pyridin-2-ylmethyl, pyridin-3-ylmethyl, pyridin-4-ylmethyl, 2-pyridin-2-ylethyl, 2-pyridin-3-ylethyl, 2-pyridin-4-ylethyl, pyrazin-2-ylmethyl, 2-pyrazin-2-ylethyl, pyridazin-4-ylmethyl, 2-pyridazin-4-ylethyl, pyrimidin-2-ylmethyl, pyrimidin-4-ylmethyl, 2-pyrimidin-2-ylethyl, 2-pyrimidin-4-ylethyl, tetrahydrofuran-2-yl, tetrahydropyran-4-yl, tetrahydrothiopyran-4-yl, azetidin-2-yl, 3-pyrrolin-2-yl, pyrrolidin-1-yl, pyrrolidin-2-yl, pyrrolidin-3-yl, morpholino, morpholin-2-yl, piperidino, piperidin-2-yl, piperidin-3-yl, piperidin-4-yl, piperazin-1-yl, isoindolin-1-yl, tetrahydrofuran-2-ylmethyl, tetrahydropyran-4-ylmethyl, 1,3-dioxolan-2-ylmethyl, 1,4-dioxan-2-ylmethyl, pyrrolidin-2-ylmethyl, piperidin-2-ylmethyl, piperidin-3-ylmethyl, piperidin-4-ylmethyl, 2-(piperidin-4-yl)ethyl, piperidin-4-yloxymethyl, piperazin-1-ylmethyl or 2-(piperazin-1-yl)ethyl, and wherein any CH, CH$_2$ or CH$_3$ group within the $Q^b$ group optionally bears on each said CH, CH$_2$ or CH$_3$ group a substituent selected from hydroxy, carbamoyl, methoxycarbonyl, ethoxycarbonyl, N-methylcarbamoyl, N-ethylcarbamoyl, N-isopropylcarbamoyl, N,N-dimethylcarbamoyl, acetyl, propionyl, pivaloyl, acetamido and N-methylacetamido, and wherein any aryl, (3-8C)cycloalkyl, heteroaryl or heterocyclyl group within the $Q^b$ group optionally bears 1 or 2 substituents, which may be the same or different, selected from fluoro, chloro, hydroxy, amino, carbamoyl, methyl, methylamino, dimethylamino, hydroxymethyl, methoxymethyl, cyanomethyl, aminomethyl, methylaminomethyl, dimethylaminomethyl and 1-methylpiperidin-4-ylmethyl;

or a pharmaceutically-acceptable salt thereof.

6. The pyrimidine derivative of the Formula I according to claim 1 wherein:—

$Q^a$ is 2-furyl, 3-furyl, 2-thienyl, 3-thienyl, 3-pyridyl, 4-pyridyl, 4-pyrimidinyl or 5-pyrimidinyl, and $Q^a$ bears 1 or 2 substituents comprising a first substituent selected from hydroxy, methoxy, hydroxymethyl and 1-hydroxyethyl, and an optional second substituent selected from fluoro, chloro, trifluoromethyl, cyano, hydroxy, methyl and methoxy;
$G^1$ is CH and $G^2$ is N, or $G^1$ is N and $G^2$ is CH;
q is 0;
r is 0;
the $X^1$-$Q^b$ group is located at the 3-position;
$X^1$ is NHCO; and
$Q^b$ is methyl, aminomethyl, 2-aminocyclopent-1-yl, 4-aminocyclohex-1-yl, 3-aminocyclohex-1-ylmethyl, 4-aminomethylcyclohex-1-yl, imidazol-1-ylmethyl, 5-amino-1,2,4-thiadiazol-3-ylmethyl, pyrrolidin-3-yl, N-methylpyrrolidin-2-yl, piperidin-2-yl, piperidin-3-yl, piperidin-4-yl, N-methylpiperidin-4-yl, pyrrolidin-2-ylmethyl, piperidin-4-ylmethyl, 2-(piperidin-4-yl)ethyl, piperidin-4-yloxymethyl or 4-methylpiperazin-1-ylmethyl, or a pharmaceutically-acceptable salt thereof.

7. The pyrimidine derivative of the Formula I according to claim 1 wherein:—

$Q^a$ is 2-furyl, 3-furyl, 2-thienyl, 3-thienyl, 3-pyridyl, 4-pyridyl, 4-pyrimidinyl, 5-pyrimidinyl, 4-benzimidazolyl or 5-benzimidazolyl, and $Q^a$ bears 1 or 2 substituents comprising a first substituent selected from hydroxy, methoxy, hydroxymethyl and 1-hydroxyethyl, and an optional second substituent selected from fluoro, chloro, trifluoromethyl, cyano, hydroxy, methyl and methoxy;
$G^1$ is CH and $G^2$ is N, or $G^1$ is N and $G^2$ is CH;
q is 0;
r is 0;
the $X^1$-$Q^b$ group is located at the 3- or 4-position;
$X^1$ is NHCO or N(Me)CO; and
$Q^b$ is aminomethyl, methylaminomethyl, ethylaminomethyl, dimethylaminomethyl, acetamidomethyl, 3-aminomethylphenyl, 4-aminomethylphenyl, 5-methylisoxazol-3-yl, 1-methylpyrazol-3-yl, 1H-1,2,3-triazol-5-yl, pyridin-4-yl, pyrazin-2-yl, 2-imidazol-1-ylethyl, 2-imidazol-2-ylethyl, 3,5-dimethyl-1H-pyrazol-1-ylmethyl, 1H-tetrazol-5-ylmethyl, 2-pyridin-3-ylethyl, 2-pyridazin-4-ylethyl, azetidin-2-yl, 3-pyrrolin-2-yl, N-methylpyrrolidin-2-yl, 4-hydroxypyrrolidin-2-yl, piperidin-3-yl, piperidin-4-yl, N-methylpiperidin-4-yl, piperazin-1-yl, piperidin-3-ylmethyl, piperidin-4-yloxymethyl or piperazin-1-ylmethyl;

or a pharmaceutically-acceptable salt thereof.

8. The pyrimidine derivative of the Formula I according to claim 1 wherein:—

$Q^a$ is 5-hydroxymethylfuran-2-yl, 5-hydroxymethylthien-2-yl or benzimidazol-4-yl;
$G^1$ is CH and $G^2$ is N, or $G^1$ is N and $G^2$ is CH;
q is 0;
r is 0;
the $X^1$-$Q^b$ group is located at the 3-position;
$X^1$ is NHCO; and
$Q^b$ is piperidin-3-yl or piperidin-4-yl;

or a pharmaceutically-acceptable salt thereof.

9. A process for the preparation of a pyrimidine derivative of the Formula I, or a pharmaceutically-acceptable salt thereof, according to claim 1 which comprises:—

(a) the reaction of a pyrimidine of the Formula II

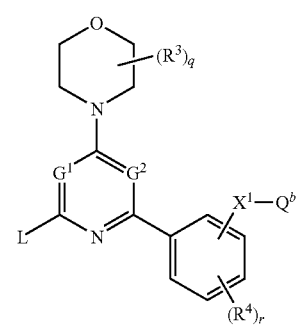

wherein L is a displaceable group and $G^1$, $G^2$, q, $R^3$, r, $R^4$, $X^1$ and $Q^b$ have any of the meanings defined in claim 1 except that any functional group is optionally protected, with an organoboron reagent of the Formula III

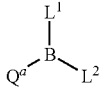

III wherein each of $L^1$ and $L^2$, which may be the same or different, is a suitable ligand and $Q^a$ has any of the meanings defined in claim 1 except that any functional group is optionally protected, whereafter any protecting group that is present is removed;

(b) for the production of those compounds of the Formula I wherein $X^1$ is $N(R^{13})CO$, the acylation of an amine of the Formula IV

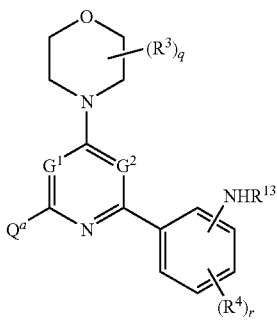

IV wherein $Q^a$, $G^1$, $G^2$, q, $R^3$, r, $R^4$ and $R^{13}$ have any of the meanings defined in claim 1 except that any functional group is optionally protected, with a carboxylic acid of the Formula V

$HO_2C-Q^b$

V or a reactive derivative thereof, wherein $Q^b$ has any of the meanings defined in claim 1 except that any functional group is optionally protected, whereafter any protecting group that is present is removed;

(c) the reaction of a pyrimidine of the Formula VI

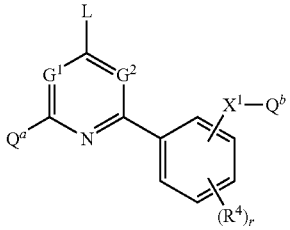

VI wherein L is a displaceable group and $Q^a$, $G^1$, $G^2$, r, $R^4$, $X^1$ and $Q^b$ have any of the meanings defined in claim 1 except that any functional group is optionally protected, with a morpholine of the Formula VII

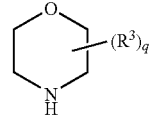

VII wherein q and $R^3$ have any of the meanings defined hereinbefore except that any functional group is optionally protected, whereafter any protecting group that is present is removed;

(d) for the production of those compounds of the Formula I wherein $X^1$ is $N(R^{13})CON(R^{13})$, the coupling of phosgene, or a chemical equivalent thereof, with an amine of the Formula IV

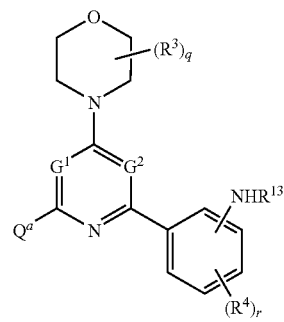

IV and an amine of the Formula VIII $R^{13}NH-Q^b$

VIII wherein $Q^a$, $G^1$, $G^2$, q, $R^3$, r, $R^4$, $R^{13}$ and $Q^b$ have any of the meanings defined in claim 1 except that any functional group is optionally protected, whereafter any protecting group that is present is removed;

(e) the reaction of a pyrimidine of the Formula XIV

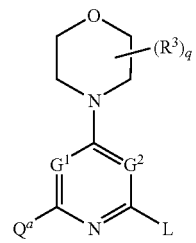

XIV wherein L is a displaceable group and $Q^a$, $G^1$, $G^2$, q and $R^3$ have any of the meanings defined in claim 1 except that any functional group is optionally protected, with an organoboron reagent of the Formula XV

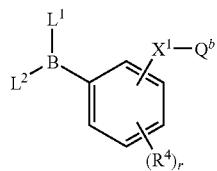

XV wherein each of $L^1$ and $L^2$, which may be the same or different, is a suitable ligand for the boron atom and r, $R^4$, $X^1$ and $Q^b$ have any of the meanings defined in claim 1 except that any functional group is protected if necessary, whereafter any protecting group that is present is removed;

(f) for the production of those compounds of the Formula I wherein $X^1$ is $CON(R^{13})$, the acylation of an amine of the Formula VIII $$R^{13}NH-Q^b \qquad \text{VIII}$$

wherein $R^{13}$ and $Q^b$ have any of the meanings defined in claim 1 except that any functional group is optionally protected, with a carboxylic acid, or a reactive derivative thereof, of the Formula XVI

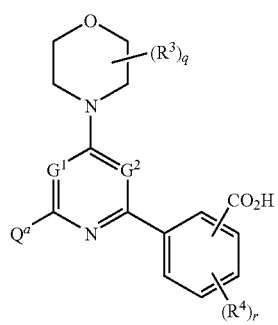

XVI wherein $Q^a$, $G^1$, $G^2$, q, $R^3$, r and $R^4$ have any of the meanings defined in claim 1 except that any functional group is optionally protected, whereafter any protecting group that is present is removed; or (g) for the production of those compounds of the Formula I wherein $X^1$ is CO and $Q^b$ is a N-linked heterocyclyl group, the acylation of a N-containing heterocyclic compound wherein any functional group is optionally protected, with a carboxylic acid, or a reactive derivative thereof, of the Formula XVI

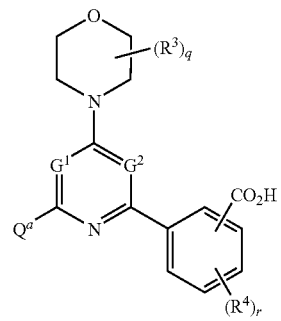

XVI wherein $Q^a$, $G^1$, $G^2$, q, $R^3$, r and $R^4$ have any of the meanings defined in claim 1 except that any functional group is optionally protected, whereafter any protecting group that is present is removed;

and optionally forming a pharmaceutically-acceptable salt of a pyrimidine derivative of the Formula I by reaction of said pyrimidine derivative with a suitable acid.

10. A pharmaceutical composition which comprises a pyrimidine derivative of the Formula I, or a pharmaceutically-acceptable salt thereof according to claim 1 in association with a pharmaceutically-acceptable diluent or carrier.

* * * * *